United States Patent
Weissman et al.

(10) Patent No.: US 8,758,750 B2
(45) Date of Patent: *Jun. 24, 2014

(54) SYNERGISTIC ANTI-CD47 THERAPY FOR HEMATOLOGIC CANCERS

(75) Inventors: Irving L. Weissman, Stanford, CA (US); Ravindra Majeti, Stanford, CA (US); Arash Ash Alizadeh, San Mateo, CA (US); Mark P. Chao, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/394,060

(22) PCT Filed: Sep. 15, 2010

(86) PCT No.: PCT/US2010/048992
§ 371 (c)(1),
(2), (4) Date: Jul. 13, 2012

(87) PCT Pub. No.: WO2011/034969
PCT Pub. Date: Mar. 24, 2011

(65) Prior Publication Data
US 2012/0282174 A1    Nov. 8, 2012

Related U.S. Application Data

(60) Provisional application No. 61/276,726, filed on Sep. 15, 2009.

(51) Int. Cl.
*A61K 39/395* (2006.01)
*A61K 39/00* (2006.01)

(52) U.S. Cl.
USPC .................. 424/130.1; 424/136.1; 424/138.1; 424/144.1; 424/155.1; 424/178.1

(58) Field of Classification Search
None
See application file for complete search history.

(56) References Cited

U.S. PATENT DOCUMENTS

| 2005/0180972 A1* | 8/2005 | Wahl et al. .................. 424/144.1 |
| 2007/0041981 A1 | 2/2007 | Howard et al. |
| 2008/0107654 A1 | 5/2008 | Kikuchi et al. |
| 2009/0191202 A1 | 7/2009 | Jamieson et al. |
| 2011/0014119 A1 | 1/2011 | Jaiswal et al. |
| 2011/0038870 A1* | 2/2011 | van den Berg ............. 424/135.1 |

FOREIGN PATENT DOCUMENTS

| WO | WO 9940940 A1 * | 8/1999 |
| WO | 2008121821 | 10/2008 |
| WO | 2009091547 | 7/2009 |
| WO | 2009091601 | 7/2009 |

OTHER PUBLICATIONS

Sehn et al., J. Clin. Oncol., 2005, 23: 5027-5033.*
Jaiswal; et al. "CD47 is Upregulated on Circulating Hematopoietic Stem Cells and Leukemia Cells to Avoid Phagocytosis", Cell (Jul. 2009), 138(2):271-285.
Majeti; et al. "CD47 is an Adverse Prognostic Factor and Therapeutic Antibody Target on Human Acute Myeloid Leukemia Stem Cells", Cell (Jul. 2009), 138(2):286-299.
Chao; et al. "CD4 is an adverse prognostic factor in non-hodgkin lymphoma and a therapeutic antibody target that synergizes with rituximab", Exp Hematol (Sep. 2009), 37(Suppl 1):S8-S9.
Chao; et al. "Therapeutic antibody targeting of CD47 synergizes with rituximab to completely eradicate human B-cell lymphoma xenografts", Blood (Nov. 2009), 114(22):1063-1064, abstract only.

* cited by examiner

*Primary Examiner* — Hong Sang
(74) *Attorney, Agent, or Firm* — Bozicevic, Field & Francis LLP; Pamela J. Sherwood; Kyle A. Gurley

(57) ABSTRACT

Methods are provided for treatment of hematologic cancers, particularly lymphomas and leukemias, including without limitation myelogenous and lymphocytic leukemias. A combination of antibodies specific for CD47; and specific for a cancer associated cell surface marker are administered to the patient, and provide for a synergistic decrease in cancer cell burden. The combination of antibodies may comprise a plurality of monospecific antibodies, or a bispecific or multispecific antibody. Markers of interest include without limitation, CD20, CD22, CD52, CD33; CD96; CD44; CD123; CD97; CD99; PTHR2; and HAVCR2.

8 Claims, 37 Drawing Sheets

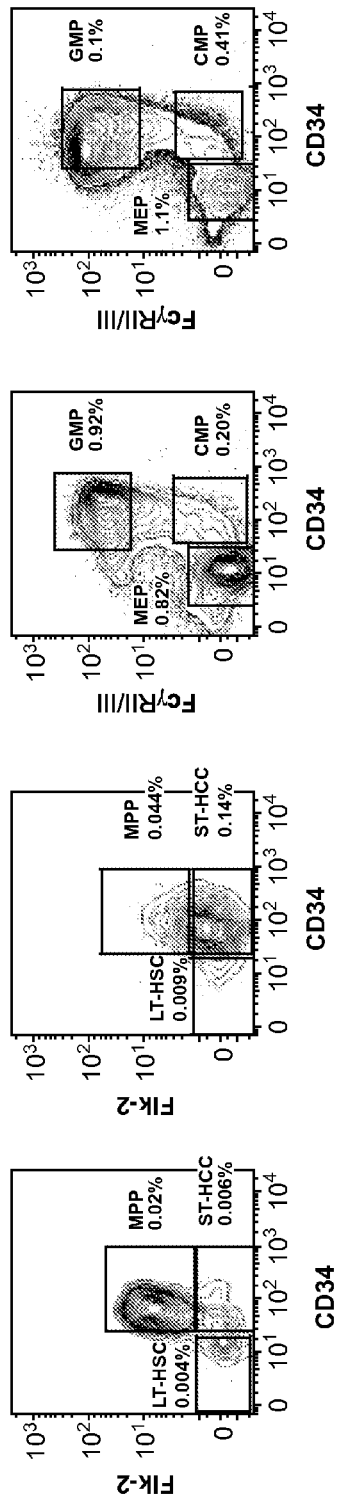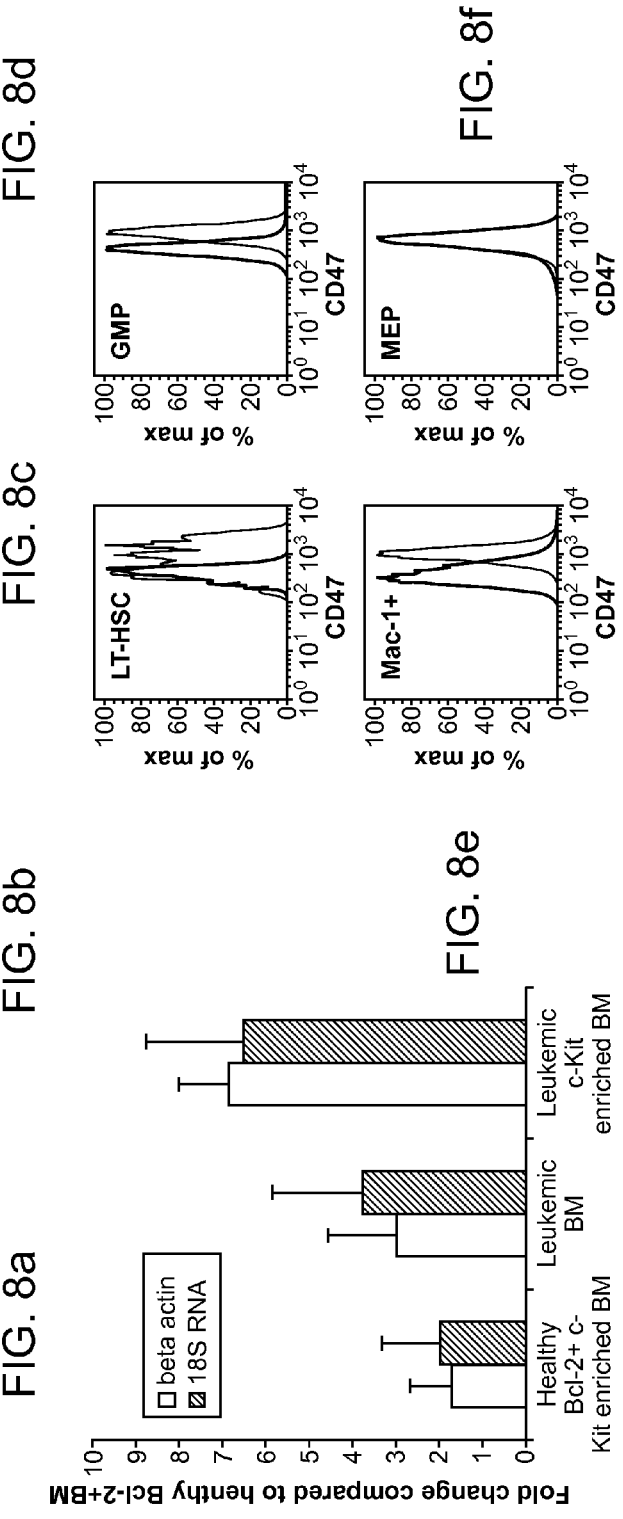

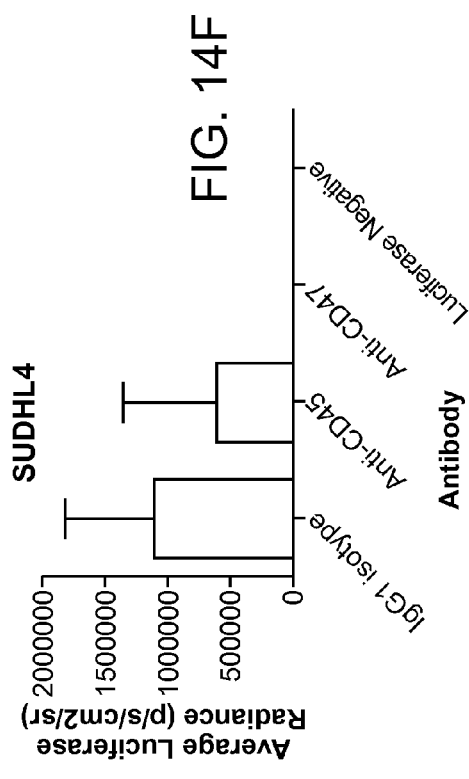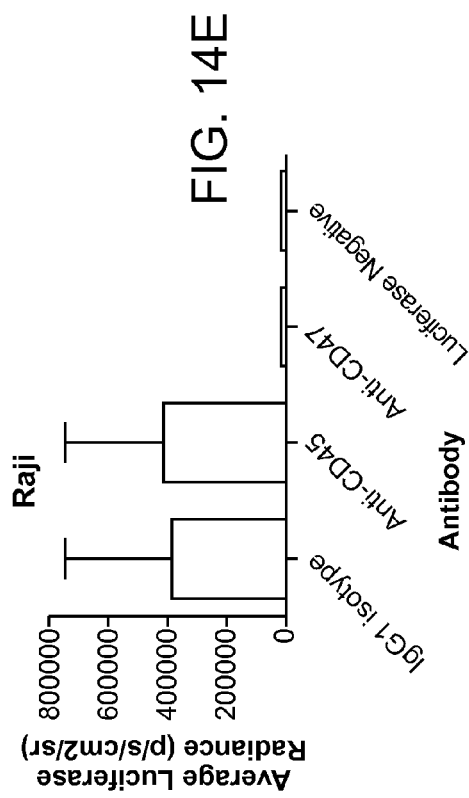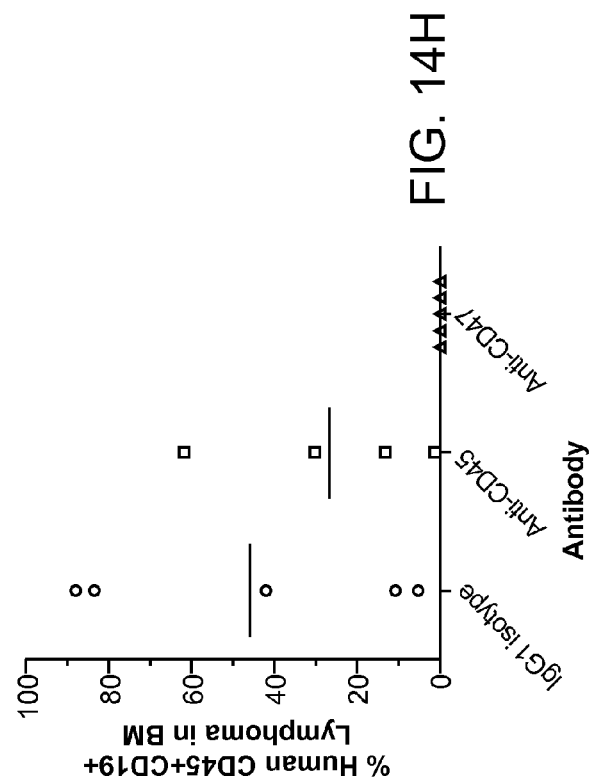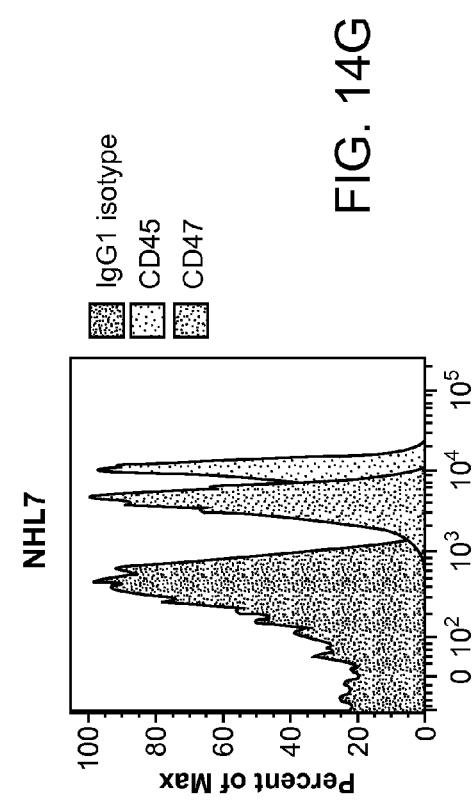

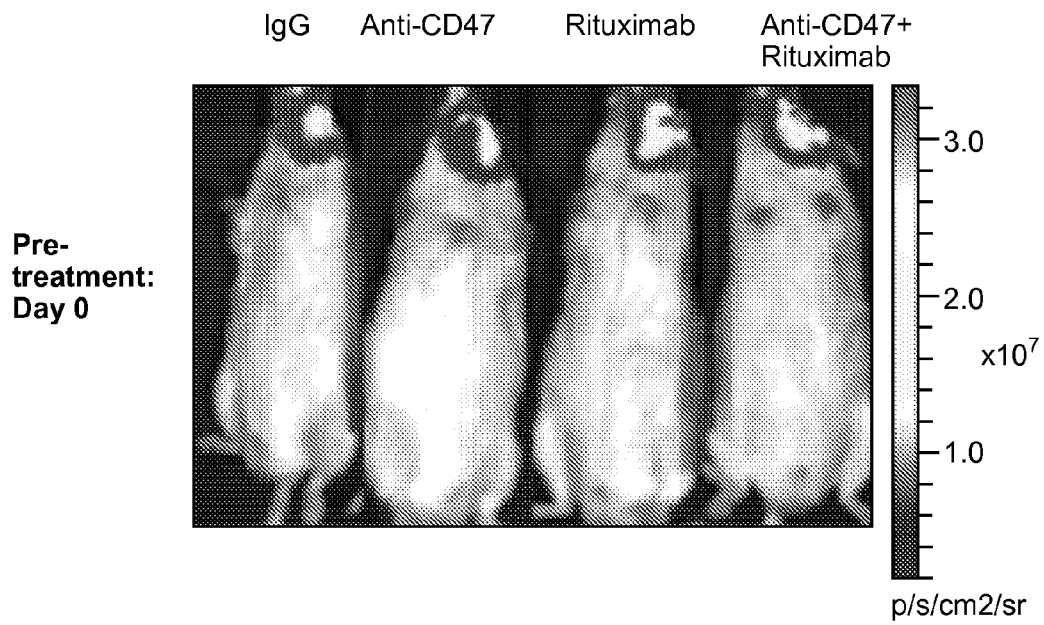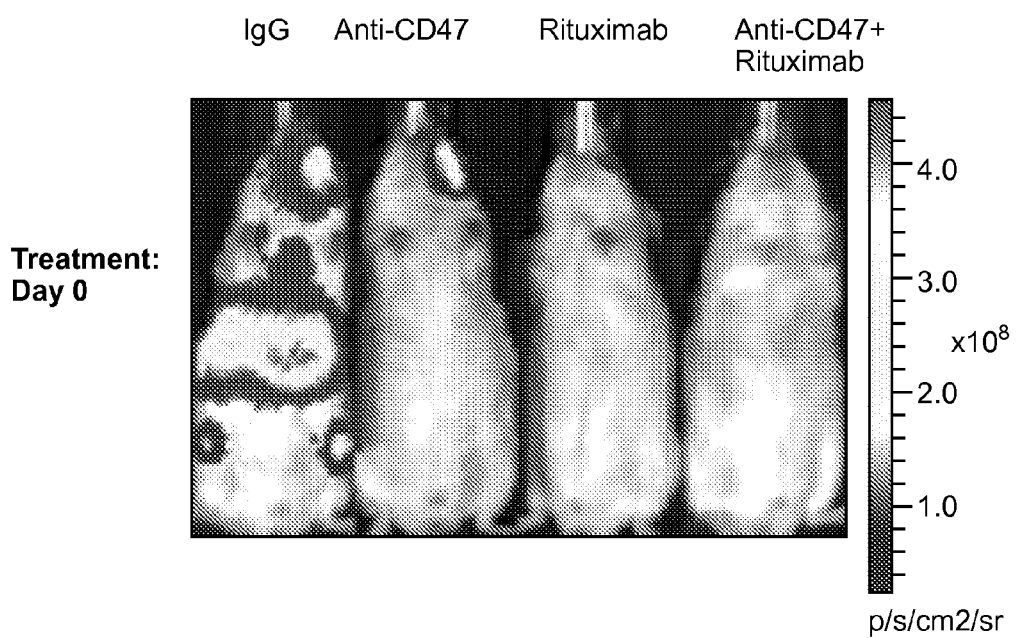
FIG. 15A

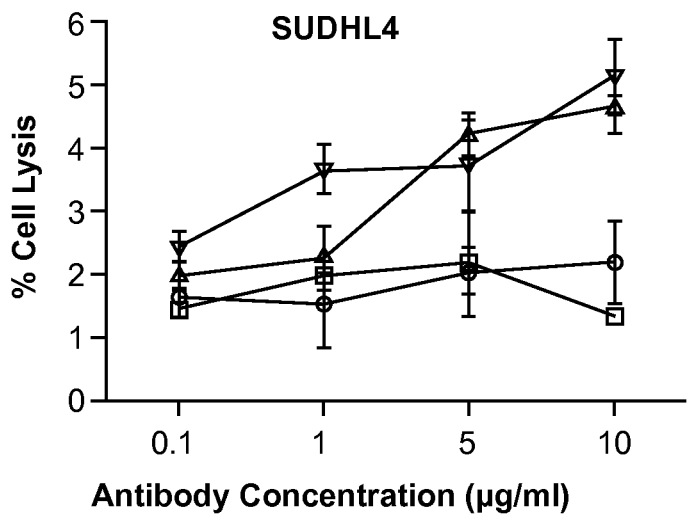
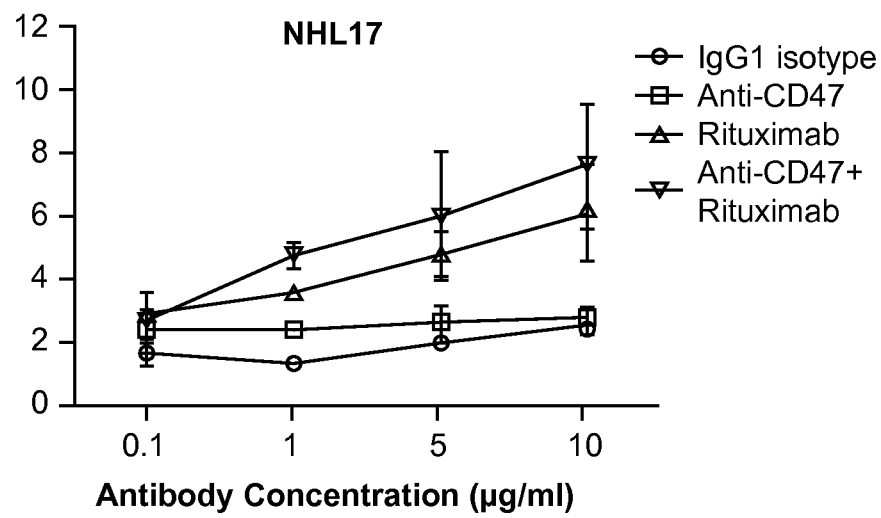
FIG. 17F

SEQUENCE LISTING

<160> NUMBER OF SEQ ID NOS: 9

<210> SEQ ID NO 1
<211> LENGTH: 305
<212> TYPE: PRT

-continued

<213> ORGANISM: H. sapiens

<400> SEQUENCE: 1

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Asn
    290                 295                 300

Asn
305

<210> SEQ ID NO 2
<211> LENGTH: 21
<212> TYPE: DNA
<213> ORGANISM: H. sapiens

<400> SEQUENCE: 2
ttgacggaag ggcaccacca g                                    21

<210> SEQ ID NO 3
<211> LENGTH: 21
<212> TYPE: DNA
<213> ORGANISM: H. sapiens

```
<400> SEQUENCE: 3
gcaccaccac ccacggaatc g                                              21

<210> SEQ ID NO 4
<211> LENGTH: 20
<212> TYPE: DNA
<213> ORGANISM: H. sapiens

<400> SEQUENCE: 4
ttccttcttg ggtatggaat                                                20

<210> SEQ ID NO 5
<211> LENGTH: 20
<212> TYPE: DNA
<213> ORGANISM: H. sapiens

<400> SEQUENCE: 5
gagcaatgat cttgatcctc                                                20

<210> SEQ ID NO 6
<211> LENGTH: 21
<212> TYPE: DNA
<213> ORGANISM: H. sapiens

<400> SEQUENCE: 6
aggccaagtc cagaagcatt c                                              21

<210> SEQ ID NO 7
<211> LENGTH: 21
<212> TYPE: DNA
<213> ORGANISM: H. sapiens

<400> SEQUENCE: 7
aatcattctg ctgctcgttg c                                              21

<210> SEQ ID NO 8
<211> LENGTH: 23
<212> TYPE: DNA
<213> ORGANISM: H. sapiens

<400> SEQUENCE: 8
gcaatttagg tatgaaagcc agc                                            23

<210> SEQ ID NO 9
<211> LENGTH: 23
<212> TYPE: DNA
<213> ORGANISM: H. sapiens

<400> SEQUENCE: 9
ctttcagcat tttgacggca acc                                            23
```

SYNERGISTIC ANTI-CD47 THERAPY FOR HEMATOLOGIC CANCERS

FEDERALLY SPONSORED RESEARCH AND DEVELOPMENT

This invention was made with Government support under grant R01CA86017 awarded by the National Institutes of Health. The government has certain rights in this invention.

BACKGROUND

The idea of a "magic bullet" was first proposed by Paul Ehrlich who at the beginning of the 20th century postulated that if a compound could be made that selectively targeted a disease-causing organism or cell, then a toxin for that organism or cell could be delivered along with the agent of selectivity. The discovery of antibodies as specific targeting agents has allowed the actual working of this concept, although the implementation in clinical therapy has required significant modifications.

Therapeutic antibodies have proven effective at fighting cancer, especially in cases where conventional therapy fails: Out of the 21 marketed therapeutic antibodies, 9 are for the treatment of cancer. Even more encouraging is that antibodies for cancer generally operate in a distinct mechanism from traditional chemotherapy or radiotherapy, so they can often be combined with traditional therapies to generate a synergistic effect. However, there is still a lot of room for improvement, in that even the most effective cancer antibodies rarely cure the disease, especially in its more advanced stages.

The first patient treated in the United States with monoclonal antibody therapy was a patient with non-Hodgkin's lymphoma, using a murine monoclonal antibody designated AB 89. Although treatment was not successful in inducing a significant clinical response, it did represent the first proof of principle in humans that a monoclonal antibody could induce transient decreases in the number of circulating tumor cells, induce circulating dead cells, and form complexes with circulating antigen, all with minimal toxicity to the patient. Although there was much excitement about this new treatment modality there were also problems and limitations, including the modulation of antigens off the cell surface and into circulation or internalization.

Monoclonal antibodies achieve their therapeutic effect through various mechanisms. They can have direct effects in producing apoptosis or programmed cell death. They can block growth factor receptors, effectively arresting proliferation of tumor cells. In cells that express monoclonal antibodies, they can bring about anti-idiotype antibody formation. Indirect effects include recruiting cells that have cytotoxicity, such as monocytes and macrophages. This type of antibody-mediated cell kill is called antibody-dependent cell mediated cytotoxicity (ADCC). Monoclonal antibodies also bind complement, leading to direct cell toxicity, known as complement dependent cytotoxicity (CDC).

Rituximab became the first monoclonal antibody approved specifically for cancer therapy, and a number of other naked or immunoconjugated antibodies have followed, including a humanized monoclonal antibody to CD33 conjugated to calicheamicin, and radiolabeled antibodies specific for CD20 (ytrrium-90 ibritumomab tiuxetan and iodine-131 tositumomab).

Rituximab has become the largest-selling biologic drug in clinical oncology, and is active in a variety of human lymphomas and chronic lymphocytic leukemia. This is a chimeric monoclonal antibody targeting the CD20 antigen found on both normal B cells and on most low-grade and some higher grade B-cell lymphomas. It can be effective as a single agent in induction and maintenance therapy. It is primarily used, however, in combination with standard chemotherapies in the treatment of patients with non-Hodgkin's B-cell lymphomas and chronic lymphocytic leukemia.

Alemtuzumab is a humanized monoclonal antibody targeting the CD52 antigen found on B lymphocytes and is used primarily for chronic lymphocytic leukemia, and is effective as induction and maintenance therapy. Alemtuzumab is also reactive with T lymphocytes, and is typically not combined with chemotherapy because of the increased risk of infection. The CD22 antigen is also targeted by a number of antibodies, and has recently demonstrated efficacy combined with toxin in chemotherapy-resistant hairy cell leukemia.

While monoclonal antibodies are now clinically important in the treatment of cancer, particularly leukemias, there remains considerable room for improvement in therapeutic methods. The present invention addresses this need.

SUMMARY OF THE INVENTION

Methods and compositions are provided for the treatment of hematologic tumors with a synergistic combination of agents. One of the agents targets the tumor cells for phagocytosis by blocking CD47 on the cell surface. It is shown that leukemia or lymphoma cells evade macrophage surveillance by upregulation of CD47 expression. Administration of agents that mask the CD47 protein, e.g. antibodies or small molecules that bind to CD47 and prevent interaction between CD47 and SIRPα, are administered to a patient, which increases the clearance of cancer cells via phagocytosis. The agent that masks CD47 is combined with monoclonal antibodies directed against one or more additional cancer cell markers, e.g. CD96, CD20, CD22, CD33, CD52, CD123, CD44, etc., which compositions can be synergistic in enhancing phagocytosis and elimination of cancer cells as compared to the use of single agents.

In some embodiments, the therapy provides for a combination of an agent that blocks CD47, and a second agent that is directed to a second cancer cell marker. Specific combinations of interest include anti-CD47 and anti-CD20, e.g. rituximab, tiuxetan, tositumomab, etc., which combination finds particular use in the treatment of non-Hodgkin's B cell lymphomas and chronic lymphocytic leukemia (CLL). A combination of anti-CD47 and anti-CD22, e.g. Epratuzumab, etc. finds particular use in the treatment of B cell leukemias and hairy cell leukemias. A combination of anti-CD47 and anti-CD52, e.g. alemtuzumab, etc., finds particular use in the treatment of B cell and T cell leukemias, including without limitation chronic lymphocytic leukemia.

A combination of anti-CD47 and anti-CD33, e.g. gemtuzumab ozogomicin, etc., finds particular use in the treatment of myeloid leukemias such as acute myelogenous leukemias. Other combination of interest for treatment of myelogenous leukemias include, without limitation, anti-CD47 and anti-CD96; anti-CD47 and anti-CD44; anti-CD47 and anti-CD123.

In other embodiments, the therapy provides for a multispecific antibody that targets CD47 and a second cancer cell marker, including multispecific antibodies that target CD47 and CD20; CD47 and CD22; CD47 and CD52; CD47 and CD33; CD47 and CD96; CD47 and CD44; Cd47 and CD123; and the like. Compositions of such multispecific antibodies are also provided, where the multispecific antibody is desir-

BRIEF DESCRIPTION OF THE DRAWINGS

FIG. 8A-F. CD47 is upregulated in murine acute myeloid leukemia. Typical stem and progenitor plots are shown for leukemic hMRP8bcrabl×hMRP8bcl2 cells compared to control non-leukemic animals. Lin−c-Kit+Sca-1+ gated cells from control bone marrow (a) and leukemic spleen (b) and Lin−c-Kit+Sca-1− gated cells from control bone marrow (c) and leukemic spleen (d) demonstrate perturberances in normal hematopoiesis in leukemic mice. Frequency is shown as a percentage of entire marrow or spleen mononuclear fraction. (e) Quantitative RT-PCR shows that CD47 is upregulated in leukemic BM cells. Data are shown from 3 sets of mice transplanted with either leukemic or control hRMP8bcrabl×hMRP8bcl2 BM cells and then sacrificed 2-6 weeks later. Results were normalized to beta-actin and 18S rRNA expression. Fold change relative to control transplanted whole Bcl-2+ BM cells was determined. Error bars represent 1 s.d. (f) Histograms show expression of CD47 on gated populations for leukemic (gray) and control (black) mice.

FIG. 12. CD47 Expression Is Increased on NHL Cells Compared to Normal B Cells, Confers a Worse Clinical Prognosis, and Correlates with Adverse Molecular Features in Multiple NHL Subtypes (A) CD47 expression on normal peripheral blood (PB) B cells (CD19$^+$), normal germinal center (GC) B cells (CD3$^-$CD5$^-$CD20$^+$CD10$^+$CD38$^+$), and NHL B cells (CD19$^+$) was determined by flow cytometry, and mean fluorescence intensity was normalized for cell size. Each point represents a different patient sample: DLBCL=2, CLL=15, MCL=4, FL=6, MZL=2, and pre-B ALL=1 (****p<0.0001). Normalized mean expression (and range) for each population were: normal PB B cells 420.9 (267.3-654.0), normal GC B cells 482.5 (441.1-519.9), and NHL 888.5 (270.1-1553). (B) CD47 expression across NHL subtypes including DLBCL (DL, n=15), MCL (n=34), FL (n=28), and B-CLL (n=14) was determined as in (A). Normalized mean expression (and range) for each population were: DL 725.7 (261.2-1344), MCL 1055 (444.2-2196), FL 825.1 (283.6-1546), CLL 713.6 (432.8-1086) (*p<0.05). (C-E) Prognostic influence of CD47 mRNA expression is shown on overall (C and E) and event-free (D) survival of patients with DLBCL, B-CLL, and MCL. For DLBCL and CLL, stratification into low and high CD47 expression groups was based on an optimal threshold determined by microarray analysis; this cutpoint was internally validated for both DLBCL and CLL and also externally validated in an independent DLBCL cohort. For MCL, stratification relative to the median was employed as an optimal cutpoint could not be defined. Significance measures are based on log-likelihood estimates of the p value, when treating CD47 expression as a continuous variable (F-H) CD47 mRNA expression is shown in relation to cell-of-origin classification for DLBCL (F), immunoglobulin heavy chain mutation status (IgVH) for CLL (G), and proliferation index for MCL (H). Error bars represent upper and lower quartiles (F and G). Analyses for (C)-(H) employed publicly available datasets for NHL patients. NGC=normal germinal center, ABC=activated B cell-like, GCB=germinal center B cell-like.

FIG. 2B p values represent comparison against IgG1 isotype control antibody.

DETAILED DESCRIPTION OF THE EMBODIMENTS

Figure 1:
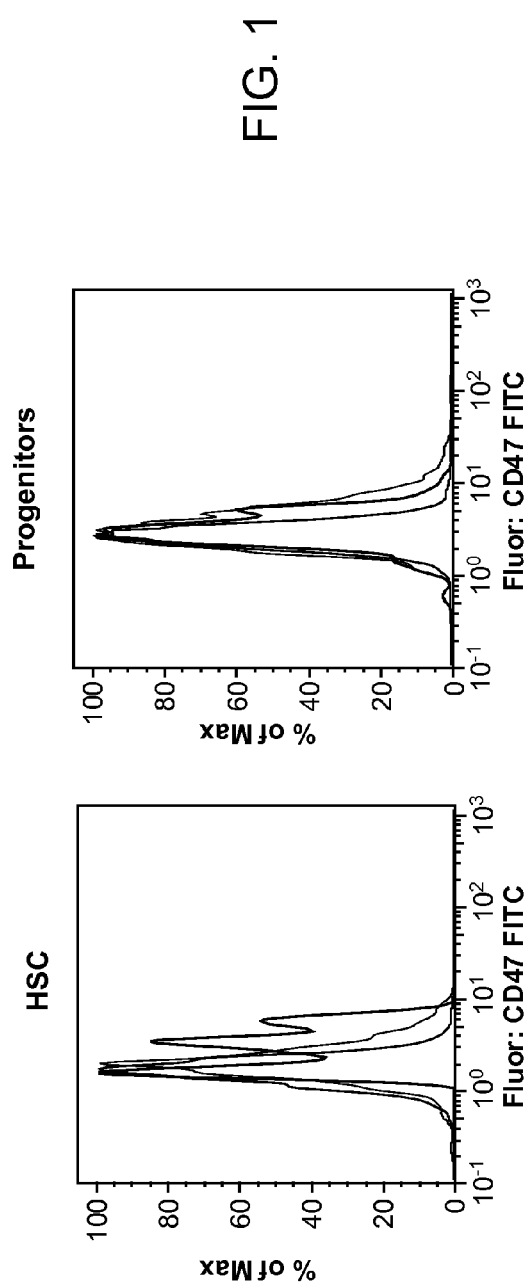
FIG. 1. FACS analysis of human HSC and progenitor CD47 expression from Myelodysplastic syndrome (MDS, blue), Chronic Myelogenous Leukemia, Accelerated Phase (CML AP, green) and normal bone marrow (red).
Figure 2:
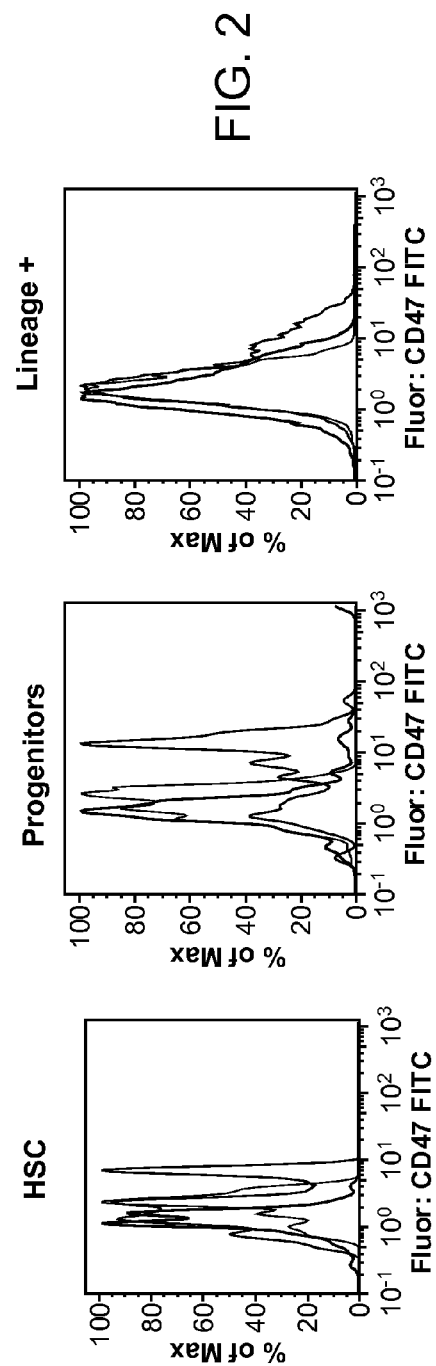
FIG. 2. ET vs. PV. FACS analysis of CD47 expression by human myeloproliferative disorders such as essential thrombocythemia (ET, blue) and polycythemia vera (PV, green) HSC, progenitor and lineage positive cells compared with human normal bone marrow (red).
Figure 3A:
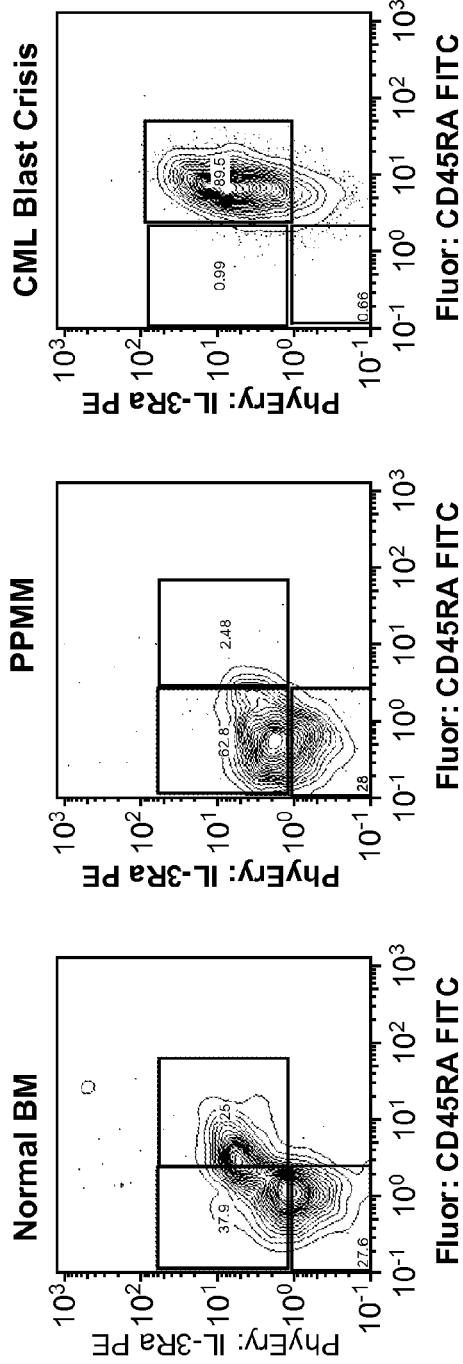
FIG. 3A. Progenitor Profiles of Normal Bone Marrow (left), post-polycythemic myelofibrosis with myeloid metaplasia (PPMM) and CML Blast Crisis.
Figure 3B:
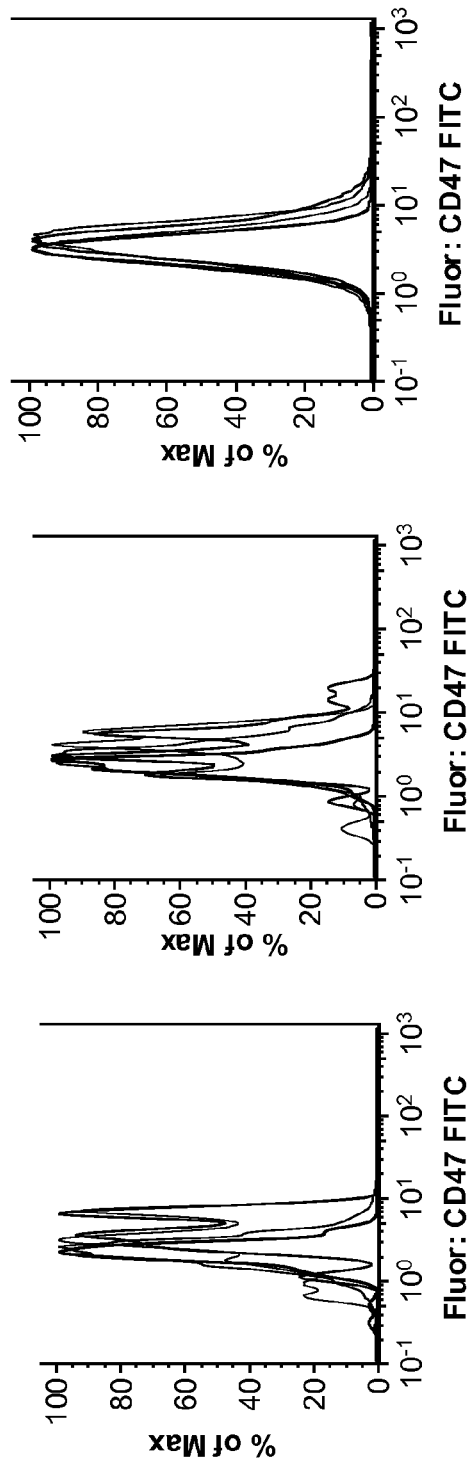
FIG. 3B. FACS analysis of human normal bone marrow (red) versus UMPD (green) versus PV (blue=ML) versus atypical CML (orange), HSC, progenitor and lineage positive cell CD47 expression.
Figure 4:
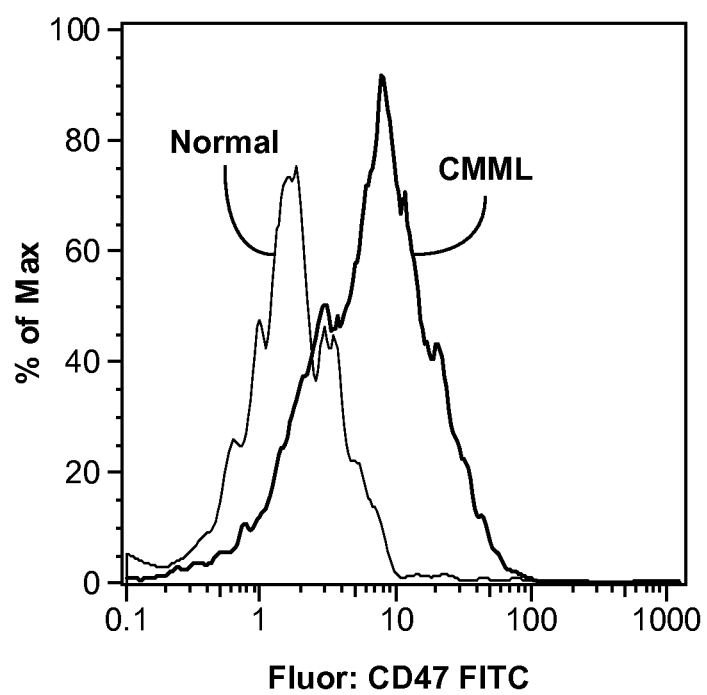
FIG. 4. Increased CD47 Expression by CMML Progenitors (blue) compared with normal bone marrow (red) with disease progression.

Methods and compositions are provided for the treatment of hematologic tumors with a synergistic combination of agents targeting CD47 and a second cancer cell marker, e.g. CD96, CD20, CD22, CD33, CD52, CD123, CD44, etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Synergistic combination. Synergistic combinations may provide for a therapeutic effect that is comparable to the effectiveness of a monotherapy, while reducing adverse side effects, e.g. damage to non-targeted tissues, immune status, and other clinical indicia. Alternatively synergistic combinations may provide for an improved effectiveness, which effect may be measured by total tumor cell number; length of time to relapse; and other indicia of patient health.

Synergistic combinations of the present invention combine an agent that is targeted to inhibit or block CD47 function; and an agent that is targeted to inhibit or block a second cancer cell marker, usually a cell surface marker. The combination may be provided with a combination of agents, e.g. two distinct antibodies, each of which is specific for a different marker; or may be provided as a multispecific agent, e.g. antibody, that combines specificity for two or more different markers.

CD47 polypeptides. The three transcript variants of human CD 47 (variant 1, NM 001777; variant 2, NM 198793; and variant 3, NM 001025079) encode three isoforms of CD47 polypeptide. CD47 isoform 1 (NP 001768), the longest of the three isoforms, is 323 amino acids long. CD47 isoform 2 (NP 942088) is 305 amino acid long. CD47 isoform 3 is 312 amino acids long. The three isoforms are identical in sequence in the first 303 amino acids. Amino acids 1-8 comprise the signal sequence, amino acids 9-142 comprise the CD47 immunoglobulin like domain, which is the soluble fragment, and amino acids 143-300 is the transmembrane domain.

A "fusion" polypeptide is a polypeptide comprising a polypeptide or portion (e.g., one or more domains) thereof fused or bonded to heterologous polypeptide. A fusion soluble CD47 protein, for example, will share at least one biological property in common with a native sequence soluble CD47 polypeptide. Examples of fusion polypeptides include immunoadhesins, as described above, which combine a portion of the CD47 polypeptide with an immunoglobulin sequence, and epitope tagged polypeptides, which comprise a soluble CD47 polypeptide or portion thereof fused to a "tag polypeptide". The tag polypeptide has enough residues to provide an epitope against which an antibody can be made, yet is short enough such that it does not interfere with biological activity of the CD47 polypeptide. Suitable tag polypeptides generally have at least six amino acid residues and usually between about 6-60 amino acid residues.

A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. The term "derivative" encompasses both amino acid sequence variants of polypeptide and covalent modifications thereof. Derivatives and fusion of soluble CD47 find use as CD47 mimetic molecules.

The first 142 amino acids of CD47 polypeptide comprise the extracellular region of CD47 (SEQ ID NO: 1). The three isoforms have identical amino acid sequence in the extracellular region, and thus any of the isoforms are can be used to generate soluble CD47. "Soluble CD47" is a CD47 protein that lacks the transmembrane domain. Soluble CD47 is secreted out of the cell expressing it instead of being localized at the cell surface.

In vitro assays for CD47 biological activity include, e.g. inhibition of phagocytosis of porcine cells by human macrophages, binding to SIRP α receptor, SIRP α tyrosine phosphorylation, etc. An exemplary assay for CD47 biological activity contacts a human macrophage composition in the presence of a candidate agent. The cells are incubated with the candidate agent for about 30 minutes and lysed. The cell lysate is mixed with anti-human SIRP α antibodies to immunoprecipitate SIRP α. Precipitated proteins are resolved by SDS PAGE, then transferred to nitrocellulose and probed with antibodies specific for phosphotyrosine. A candidate agent useful as a CD47 mimetic increases SIRP α tyrosine phosphorylation by at least 10%, or up to 20%, or 50%, or 70% or 80% or up to about 90% compared to the level of phosphorylation observed in the absence of candidate agent. Another exemplary assay for CD47 biological activity measures phagocytosis of hematopoietic cells by human macrophages. A candidate agent useful as a CD47 mimetic results in the down regulation of phagocytosis by at least about 10%, at least about 20%, at least about 50%, at least about 70%, at least about 80%, or up to about 90% compared to level of phagocytosis observed in absence of candidate agent.

By "manipulating phagocytosis" is meant an up-regulation or a down-regulation in phagocytosis by at least about 10%, or up to 20%, or 50%, or 70% or 80% or up to about 90% compared to level of phagocytosis observed in absence of intervention. Thus in the context of decreasing phagocytosis of circulating hematopoietic cells, particularly in a transplantation context, manipulating phagocytosis means a down-regulation in phagocytosis by at least about 10%, or up to 20%, or 50%, or 70% or 80% or up to about 90% compared to level of phagocytosis observed in absence of intervention.

CD47 inhibitors. Agents of interest as CD47 inhibitors include specific binding members that prevent the binding of CD47 with SIRPα receptor. The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). CD47 inhibitors useful in the methods of the invention include analogs, derivatives and fragments of the original specific binding member.

In a preferred embodiment, the specific binding member is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies utilized in the present invention may be polyclonal antibodies, although monoclonal antibodies are preferred because they may be reproduced by cell culture or recombinantly, and can be modified to reduce their antigenicity.

Polyclonal antibodies can be raised by a standard protocol by injecting a production animal with an antigenic composition. See, e.g., Harlow and Lane, Antibodies: A Laboratory Manual, Cold Spring Harbor Laboratory, 1988. When utilizing an entire protein, or a larger section of the protein, antibodies may be raised by immunizing the production animal with the protein and a suitable adjuvant (e.g., Freund's, Freund's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the protein target, a superior immune response may be elicited if the polypeptide is joined to a carrier protein, such as ovalbumin, BSA or KLH. Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. In addition, the antibodies or antigen binding fragments may be produced by genetic engineering. Humanized, chimeric, or xenogeneic human antibodies, which produce less of an immune response when administered to humans, are preferred for use in the present invention.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ricin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Antibodies include free antibodies and antigen binding fragments derived therefrom, and conjugates, e.g. pegylated antibodies, drug, radioisotope, or toxin conjugates, and the like. Monoclonal antibodies directed against a specific epitope, or combination of epitopes, will allow for the targeting and/or depletion of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al. Cell, 96:737-49 (1999)). These techniques allow for the screening of particular populations of cells; in immunohistochemistry of biopsy samples; in detecting the presence of markers shed by cancer cells into the blood and other biologic fluids, and the like.

Humanized versions of such antibodies are also within the scope of this invention. Humanized antibodies are especially useful for in vivo applications in humans due to their low antigenicity.

The phrase "multispecific or bispecific antibody" refers to a synthetic or recombinant antibody that recognizes more than one protein. Examples include bispecific antibodies 2B1, 520C9×H22, mDX-H210, and MDX447. Bispecific antibodies directed against a combination of epitopes, will allow for the targeting and/or depletion of cellular populations expressing the combination of epitopes. Exemplary bispecific antibodies include those targeting a combination of CD47 and a cancer cell marker, such as, CD20, CD22, CD96, CD97, CD99, PTHR2, HAVCR2 etc. Generation of bi-specific antibodies are described in the literature, for example, in U.S. Pat. No. 5,989,830, U.S. Pat. No. 5,798,229, which are incorporated herein by reference. Higher order specificities, e.g. trispecific antibodies, are described by Holliger and Hudson (2005) Nature Biotechnology 23:1126-1136.

The efficacy of a CD47 inhibitor is assessed by assaying CD47 activity. The above-mentioned assays or modified versions thereof are used. In an exemplary assay, AML SCs are incubated with bone marrow derived macrophages, in the presence or absence of the candidate agent. An inhibitor of the cell surface CD47 will up-regulate phagocytosis by at least about 10%, or up to 20%, or 50%, or 70% or 80% or up to about 90% compared to the phagocytosis in absence of the candidate agent. Similarly, an in vitro assay for levels of tyrosine phosphorylation of SIRPα will show a decrease in phosphorylation by at least about 10%, or up to 20%, or 50%, or 70% or 80% or up to about 90% compared to phosphorylation observed in absence of the candidate agent.

In one embodiment of the invention, the agent, or a pharmaceutical composition comprising the agent, is provided in an amount effective to detectably inhibit the binding of CD47 to SIRPα receptor present on the surface of phagocytic cells. The effective amount is determined via empirical testing routine in the art. The effective amount may vary depending on the number of cells being transplanted, site of transplantation and factors specific to the transplant recipient.

The terms "phagocytic cells" and "phagocytes" are used interchangeably herein to refer to a cell that is capable of phagocytosis. There are four main categories of phagocytes: macrophages, mononuclear cells (histiocytes and monocytes); polymorphonuclear leukocytes (neutrophils) and dendritic cells.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, e.g. mouse, rat, rabbit, pig, primate, including humans and other apes, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "recipient", "individual", "subject", "host", and "patient", used interchangeably herein and refer to any mammalian subject for whom diagnosis, treatment, or therapy is desired, particularly humans.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include pre-cancerous (e.g., benign), malignant, pre-metastatic, metastatic, and non-metastatic cells. Detection of cancerous cells is of particular interest. The term "normal" as used in the context of "normal cell," is meant to refer to a cell of an untransformed phenotype or exhibiting a morphology of a non-transformed cell of the tissue type being examined. "Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

"Therapeutic target" refers to a gene or gene product that, upon modulation of its activity (e.g., by modulation of expression, biological activity, and the like), can provide for modulation of the cancerous phenotype. As used throughout, "modulation" is meant to refer to an increase or a decrease in the indicated phenomenon (e.g., modulation of a biological activity refers to an increase in a biological activity or a decrease in a biological activity).

Hematologic Cancers

Acute leukemias are rapidly progressing leukemia characterized by replacement of normal bone marrow by blast cells of a clone arising from malignant transformation of a hematopoietic cell. The acute leukemias include acute lymphoblastic leukemia (ALL) and acute myelogenous leukemia (AML). ALL often involves the CNS, whereas acute monoblastic leukemia involves the gums, and AML involves localized collections in any site (granulocytic sarcomas or chloromas).

The presenting symptoms are usually nonspecific (e.g., fatigue, fever, malaise, weight loss) and reflect the failure of normal hematopoiesis. Anemia and thrombocytopenia are very common (75 to 90%). The WBC count may be decreased, normal, or increased. Blast cells are usually found in the blood smear unless the WBC count is markedly decreased. The blasts of ALL can be distinguished from those of AML by histochemical studies, cytogenetics, immunophenotyping, and molecular biology studies. In addition to smears with the usual stains, terminal transferase, myeloperoxidase, Sudan black B, and specific and nonspecific esterase.

ALL is the most common malignancy in children, with a peak incidence from ages 3 to 5 yr. It also occurs in adolescents and has a second, lower peak in adults. Typical treatment emphasizes early introduction of an intensive multidrug regimen, which may include prednisone, vincristine, anthracycline or asparaginase. Other drugs and combinations are cytarabine and etoposide, and cyclophosphamide. Relapse usually occurs in the bone marrow but may also occur in the CNS or testes, alone or concurrent with bone marrow. Although second remissions can be induced in many children, subsequent remissions tend to be brief.

The incidence of AML increases with age; it is the more common acute leukemia in adults. AML may be associated with chemotherapy or irradiation (secondary AML). Remission induction rates are lower than with ALL, and long-term disease-free survival reportedly occurs in only 20 to 40% of patients. Treatment differs most from ALL in that AML responds to fewer drugs. The basic induction regimen includes cytarabine; along with daunorubicin or idarubicin. Some regimens include 6-thioguanine, etoposide, vincristine, and prednisone.

Polycythemia vera (PV) is an idiopathic chronic myeloproliferative disorder characterized by an increase in Hb concentration and RBC mass (erythrocytosis). PV occurs in about 2.3/100,000 people per year; more often in males (about 1.4:1). The mean age at diagnosis is 60 yr (range, 15 to 90 yr; rarely in childhood); 5% of patients are <40 yr at onset. The bone marrow sometimes appears normal but usually is hypercellular; hyperplasia involves all marrow elements and replaces marrow fat. There is increased production and turnover of RBCs, neutrophils, and platelets. Increased megakaryocytes may be present in clumps. Marrow iron is absent in >90% of patients, even when phlebotomy has not been performed.

Myelodysplastic syndrome (MDS) is a group of syndromes (preleukemia, refractory anemias, Ph-negative chronic myelocytic leukemia, chronic myelomonocytic leukemia, myeloid metaplasia) commonly seen in older patients. Exposure to carcinogens may by be implicated. MDS is characterized by clonal proliferation of hematopoietic cells, including erythroid, myeloid, and megakaryocytic forms. The bone marrow is normal or hypercellular, and ineffective hematopoiesis causes variable cytopenias, the most frequent being anemia. The disordered cell production is also associated with morphologic cellular abnormalities in marrow and blood. Extramedullary hematopoiesis may occur, leading to hepatomegaly and splenomegaly. Myelofibrosis is occasionally present at diagnosis or may develop during the course of MDS. The MDS clone is unstable and tends to progress to AML.

Non-Hodgkin lymphomas are a heterogeneous group of disorders involving malignant monoclonal proliferation of lymphoid cells in lymphoreticular sites, including lymph nodes, bone marrow, the spleen, the liver, and the GI tract. It is the 6th most common cancer in the US; about 65,000 new cases are diagnosed annually in all age groups. Presenting symptoms usually include peripheral lymphadenopathy. However, some patients present without adenopathy but with abnormal lymphocytes in circulation. Compared with Hodgkin lymphoma, there is a greater likelihood of disseminated disease at the time of diagnosis. Diagnosis is usually based on lymph node or bone marrow biopsy or both. Treatment involves radiation therapy, chemotherapy, or both. Stem cell transplantation is usually reserved for salvage therapy after incomplete remission or relapse.

Most (80 to 85%) NHLs arise from B cells; the remainder arise from T cells or natural killer cells. Either precursor or mature cells may be involved. Overlap exists between leukemia and NHL because both involve proliferation of lymphocytes or their precursors. A leukemia-like picture with peripheral lymphocytosis and bone marrow involvement may be present in up to 50% of children and in about 20% of adults with some types of NHL.

Among the lymphomas within this group are: precursor B-lymphoblastic leukemia/lymphoma; B-cell chronic lymphocytic leukemia/small lymphocytic lymphoma; B-cell prolymphocytic leukemia; Lymphoplasmacytic lymphoma; Splenic marginal zone B-cell lymphoma (±villous lymphocytes); Hairy cell leukemia; Plasma cell myeloma/plasmacytoma; Extranodal marginal zone B-cell lymphoma of the MALT type; Nodal marginal zone B-cell lymphoma (±monocytoid B cells); Follicular lymphoma; Mantle cell lymphoma; Diffuse large B-cell lymphomas; Burkitt's lymphoma; Precursor T-lymphoblastic lymphoma/leukemia; T-cell prolymphocytic leukemia; T-cell granular lymphocytic leukemia; Aggressive NK cell leukemia; Adult T-cell lymphoma/leukemia (HTLV 1-positive); Extranodal NK/T-cell lymphoma, nasal type; Enteropathy-type T-cell lymphoma; Hepatosplenic γ-δ T-cell lymphoma; Subcutaneous panniculitis-like T-cell lymphoma; Mycosis fungoides/Sézary syndrome; Anaplastic large cell lymphoma, T/null cell, primary cutaneous type; Anaplastic large cell lymphoma, T-/null-cell, primary systemic type; Peripheral T-cell lymphoma, not otherwise characterized; Angioimmunoblastic T-cell lymphoma.

B cell hematologic cancers within the NHL group include, without limitation, diffuse large B cell lymphoma, chronic lymphocytic leukemia, mantle cell lymphoma, B lymphoblastic leukemia/lymphoma, and Burkitt's lymphoma. Diffuse large B cell lymphomas are of particular interest in this group.

Lymphomas are commonly also categorized as indolent or aggressive. Indolent lymphomas are slowly progressive and responsive to therapy but are often not curable with conventional approaches. Aggressive lymphomas are rapidly progressive but responsive to therapy and often curable.

In children, NHL is almost always aggressive. The treatment of these aggressive lymphomas (Burkitt's, diffuse large B cell, and lymphoblastic lymphoma) presents special concerns, including GI tract involvement (particularly in the terminal ileum); meningeal spread (requiring CSF prophylaxis or treatment); and other sanctuary sites of involvement (such as testis or brain). In addition, with these potentially curable lymphomas, treatment adverse effects as well as outcome must be considered, including late risks of secondary cancer.

Rituximab is included in the standard chemotherapeutic regimen. Patients in the highest risk groups (patients with 4 or 5 risk factors) now have a 50% 5-yr survival. In patients with the aggressive B-cell lymphomas (eg, diffuse large B cell), the standard drug combination is rituximab plus cyclophosphamide, hydroxydaunorubicin, vincristine, prednisone (R-CHOP). Complete disease regression is expected in ≥70% of patients, depending on the IPI category.

Chronic leukemia usually manifests as abnormal leukocytosis with or without cytopenia in an otherwise asymptomatic person. Findings and management differ significantly between chronic lymphocytic leukemia (CLL) and chronic myelocytic leukemia (CML).

The most common type of leukemia in the Western world, CLL involves mature-appearing defective neoplastic lymphocytes (almost always B cells) with an abnormally long life span. The peripheral blood, bone marrow, spleen, and lymph nodes undergo leukemic infiltration. Symptoms may be absent or may include lymphadenopathy, splenomegaly, hepatomegaly, and nonspecific symptoms attributable to anemia (fatigue, malaise). Diagnosis is by examination of peripheral smear and bone marrow aspirate. Treatment, delayed until symptoms develop, is aimed at lengthening life and decreasing symptoms and may involve chlorambucil or fludarabine, prednisone, and cyclophosphamide or doxorubicin or both. Monoclonal antibodies, such as alemtuzumab and rituximab, are increasingly being used. Palliative radiation therapy is reserved for patients whose lymphadenopathy or splenomegaly interferes with other organs.

In about 98% of cases, CD5+ B cells undergo malignant transformation, with lymphocytes initially accumulating in the bone marrow and then spreading to lymph nodes and other lymphoid tissues, eventually inducing splenomegaly and hepatomegaly. As CLL progresses, abnormal hematopoiesis results in anemia, neutropenia, thrombocytopenia, and decreased immunoglobulin production. Many patients develop hypogammaglobulinemia and impaired antibody response, perhaps related to increased T-suppressor cell activity. Patients have increased susceptibility to autoimmune disease characterized by immunohemolytic anemias (usually Coombs' test-positive) or thrombocytopenia and a modest increase in risk of developing other cancers.

Monoclonal antibody therapy: Rituximab is the first monoclonal antibody used in the successful treatment of lymphoid cancers. The partial response rate with conventional doses in CLL is 10 to 15%. In previously untreated patients, the response rate is 75%, with 20% of patients achieving complete remission. Alemtuzumab has a 33% response rate in previously treated patients refractory to fludarabine and a 75 to 80% response rate in previously untreated patients.

Multiple myeloma is a cancer of plasma cells that produce monoclonal immunoglobulin and invade and destroy adjacent bone tissue. Common manifestations include bone pain, renal insufficiency, hypercalcemia, anemia, and recurrent infections. Diagnosis requires demonstration of M-protein (sometimes present in urine and not serum) and either lytic bone lesions, light-chain proteinuria, or excessive marrow plasma cells. A bone marrow biopsy is usually needed. Specific treatment includes conventional chemotherapy with the addition of bortezomib, lenalidomide, thalidomide, corticosteroids, and high-dose melphalan followed by autologous peripheral blood stem cell transplantation.

The M-protein produced by the malignant plasma cells is IgG in about 55% of myeloma patients and IgA in about 20%; of patients producing either IgG or IgA, 40% also have Bence Jones proteinuria, which is free monoclonal K or A light chains in the urine. In 15 to 20% of patients, plasma cells secrete only Bence Jones protein. IgD myeloma accounts for about 1% of cases.

Treatment of Cancer

The invention provides methods for reducing growth of hematologic cancer cells through the introduction of a CD47 blocking agent, e.g. an anti-CD47 antibody, small molecule, etc., in combination with a second agent that block a second cancer cell marker. In certain embodiments the cancer is AML, where the second cancer associated marker may be CD33, CD44, CD123, CD96, CD97, CD99, PTHR2, HAVCR2, etc. In other embodiments the cancer is diffuse large B cell lymphoma, where the second cancer associated marker may be CD20, CD22, etc. In other embodiments the cancer is CLL, where the second marker may be CD20, CD22, CD52, etc. By blocking the activity of CD47, the downregulation of phagocytosis that is found with certain tumor cells, e.g. AML cells, is prevented.

"Reducing growth of cancer cells" includes, but is not limited to, reducing proliferation of cancer cells, and reducing the incidence of a non-cancerous cell becoming a cancerous cell. Whether a reduction in cancer cell growth has been achieved can be readily determined using any known assay, including, but not limited to, [$^3$H]-thymidine incorporation; counting cell number over a period of time; detecting and/or measuring a marker associated with AML, etc.

Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood of the individual. The substance can be administered systemically or locally, usually systemically.

As an alternative embodiment, an agent, e.g. a chemotherapeutic drug that reduces cancer cell growth, can be targeted to a cancer cell by conjugation to a CD47 specific antibody. Thus, in some embodiments, the invention provides a method of delivering a drug to a cancer cell, comprising administering a drug-antibody complex to a subject, wherein the antibody is specific for a cancer-associated polypeptide, and the drug is one that reduces cancer cell growth, a variety of which are known in the art. Targeting can be accomplished by coupling (e.g., linking, directly or via a linker molecule, either covalently or non-covalently, so as to form a drug-antibody complex) a drug to an antibody specific for a cancer-associated polypeptide. Methods of coupling a drug to an antibody are well known in the art and need not be elaborated upon herein.

In certain embodiments, a bi-specific antibody may be used. For example a bi-specific antibody in which one antigen binding domain is directed against CD47 and the other antigen binding domain is directed against a cancer cell marker, such as, CD20, CD22, CD33, CD44, CD52, CD123, CD96, CD97, CD99, PTHR2, HAVCR2 etc. may be used.

Generally, as the term is utilized in the specification, "antibody" or "antibody moiety" is intended to include any polypeptide chain-containing molecular structure that has a specific shape which fits to and recognizes an epitope, where one or more non-covalent binding interactions stabilize the complex between the molecular structure and the epitope. For monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

Antibodies which have a reduced propensity to induce a violent or detrimental immune response in humans (such as anaphylactic shock), and which also exhibit a reduced propensity for priming an immune response which would prevent repeated dosage with the antibody therapeutic or imaging agent (e.g., the human-anti-murine-antibody "HAMA" response), are preferred for use in the invention. These antibodies are preferred for all administrative routes. Thus, humanized, chimeric, or xenogenic human antibodies, which produce less of an immune response when administered to humans, are preferred for use in the present invention.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference).

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

Alternatively, polyclonal or monoclonal antibodies may be produced from animals which have been genetically altered to produce human immunoglobulins. The transgenic animal may be produced by initially producing a "knock-out" animal which does not produce the animal's natural antibodies, and stably transforming the animal with a human antibody locus (e.g., by the use of a human artificial chromosome). Only human antibodies are then made by the animal. Techniques for generating such animals, and deriving antibodies therefrom, are described in U.S. Pat. Nos. 6,162,963 and 6,150,584, incorporated fully herein by reference. Such fully human xenogenic antibodies are a preferred antibody for use in the methods and compositions of the present invention. Alternatively, single chain antibodies can be produced from phage libraries containing human variable regions. See U.S. Pat. No. 6,174,708, incorporated fully herein by reference.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ficin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Fv fragments are heterodimers of the variable heavy chain domain ($V_H$) and the variable light chain domain ($V_L$). The heterodimers of heavy and light chain domains that occur in whole IgG, for example, are connected by a disulfide bond. Recombinant Fvs in which $V_H$ and $V_L$ are connected by a peptide linker are typically stable, see, for example, Huston et al., Proc. Natl. Acad, Sci. USA 85:5879 5883 (1988) and Bird et al., Science 242:423 426 (1988), both fully incorporated herein, by reference. These are single chain Fvs which have been found to retain specificity and affinity and have been shown to be useful for imaging tumors and to make recombinant immunotoxins for tumor therapy. However, researchers have found that some of the single chain Fvs have a reduced affinity for antigen and the peptide linker can interfere with binding. Improved Fv's have been also been made which comprise stabilizing disulfide bonds between the $V_H$ and $V_L$ regions, as described in U.S. Pat. No. 6,147,203, incorporated fully herein by reference. Any of these minimal antibodies may be utilized in the present invention, and those which are humanized to avoid HAMA reactions are preferred for use in embodiments of the invention.

In addition, derivatized immunoglobulins with added chemical linkers, detectable moieties such as fluorescent dyes, enzymes, substrates, chemiluminescent moieties, specific binding moieties such as streptavidin, avidin, or biotin, or drug conjugates may be utilized in the methods and compositions of the present invention.

In some embodiments of the invention, the antibodies are coupled or conjugated to one or more therapeutic cytotoxic or imaging moieties. As used herein, "cytotoxic moiety" (C) simply means a moiety which inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof. Agents may be conjugated to the antibody by any suitable technique, with appropriate consideration of the need for pharmokinetic stability and reduced overall toxicity to the patient. A therapeutic agent may be coupled to a suitable antibody moiety either directly or indirectly (e.g. via a linker group). A direct reaction between an agent and an antibody is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance an antibody from an agent in order to avoid interference with binding capabilities. A linker group can also serve to increase the chemical reactivity of a substituent on a moiety or an antibody, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups may be designed into recombinant immunoglobulin molecules. It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958. As an alternative coupling method, cytotoxic moieties may be coupled to the antibody through a an oxidized carbohydrate group at a glycosylation site, as described in U.S. Pat. Nos. 5,057,313 and 5,156,840. Yet another alternative method of coupling the antibody moiety to the cytotoxic moiety is by the use of a non-covalent binding pair, such as streptavidin/biotin, or avidin/biotin. In these embodiments, one member of the pair is covalently coupled to the antibody moiety and the other member of the binding pair is covalently coupled to the cytotoxic or imaging moiety.

Where a cytotoxic moiety is more potent when free from the antibody portion of the immunoconjugates of the present invention, it may be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

It may be desirable to couple more than one cytotoxic imaging moiety to an antibody. By poly-derivatizing the antibody, several cytotoxic strategies may be simultaneously implemented, or a therapeutic antibody may be labeled for tracking by a visualization technique. Regardless of the particular embodiment, immunoconjugates with more than one moiety may be prepared in a variety of ways. For example, more than one moiety may be coupled directly to an antibody molecule, or linkers which provide multiple sites for attachment (e.g., dendrimers) can be used. Alternatively, a carrier with the capacity to hold more than one cytotoxic or imaging moiety can be used.

A carrier may bear the agents in a variety of ways, including covalent bonding either directly or via a linker group, and non-covalent associations. Suitable covalent-bond carriers include proteins such as albumins (e.g., U.S. Pat. No. 4,507,234), peptides, and polysaccharides such as aminodextran (e.g., U.S. Pat. No. 4,699,784), each of which have multiple sites for the attachment of moieties. A carrier may also bear an agent by non-covalent associations, such as non-covalent bonding or by encapsulation, such as within a liposome vesicle (e.g., U.S. Pat. Nos. 4,429,008 and 4,873,088). Encapsulation carriers are especially useful for imaging moiety conjugation to antibody moieties for use in the invention, as a sufficient amount of the imaging moiety (dye, magnetic resonance contrast reagent, etc.) for detection may be more easily associated with the antibody moiety. In addition, encapsulation carriers are also useful in chemotoxic therapeutic embodiments, as they can allow the therapeutic compositions to gradually release a chemotoxic moiety over time while concentrating it in the vicinity of the tumor cells.

Preferred radionuclides for use as cytotoxic moieties are radionuclides which are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use.

Preferred chemotoxic agents include small-molecule drugs such as carboplatin, cisplatin, vincristine, taxanes such as paclitaxel and doceltaxel, hydroxyurea, gemcitabine, vinorelbine, irinotecan, tirapazamine, matrilysin, methotrexate, pyrimidine and purine analogs, and other suitable small toxins known in the art. Preferred chemotoxin differentiation inducers include phorbol esters and butyric acid. Chemotoxic moieties may be directly conjugated to the antibody moiety via a chemical linker, or may be encapsulated in a carrier, which is in turn coupled to the antibody. Preferred toxin proteins for use as cytotoxic moieties include ricins A and B, abrin, diphtheria toxin, bryodin 1 and 2, momordin, trichokirin, cholera toxin, gelonin, *Pseudomonas* exotoxin, *Shigella* toxin, pokeweed antiviral protein, and other toxin proteins known in the medicinal biochemistry arts. As these toxin agents may elicit undesirable immune responses in the patient, especially if injected intravascularly, it is preferred that they be encapsulated in a carrier for coupling to the antibody.

For administration, the anti-CD47 and the second agent may be administered separately or together; and will generally be administered within the same general time frame, e.g. within a week, within 3-4 days, within 1 day or simultaneously with each other.

The agent or agents are mixed, prior to administration, with a non-toxic, pharmaceutically acceptable carrier substance.

Usually, this will be an aqueous solution, such as normal saline or phosphate-buffered saline (PBS), Ringer's solution, lactate-Ringer's solution, or any isotonic physiologically acceptable solution for administration by the chosen means. Preferably, the solution is sterile and pyrogen-free, and is manufactured and packaged under current Good Manufacturing Processes (GMPs), as approved by the FDA. The clinician of ordinary skill is familiar with appropriate ranges for pH, tonicity, and additives or preservatives when formulating pharmaceutical compositions for administration by intravascular injection, direct injection into the lymph nodes, intraperitoneal, or by other routes. In addition to additives for adjusting pH or tonicity, the agents may be stabilized against aggregation and polymerization with amino acids and non-ionic detergents, polysorbate, and polyethylene glycol. Optionally, additional stabilizers may include various physiologically-acceptable carbohydrates and salts. Also, polyvinylpyrrolidone may be added in addition to the amino acid. Suitable therapeutic immunoglobulin solutions which are stabilized for storage and administration to humans are described in U.S. Pat. No. 5,945,098, incorporated fully herein by reference. Other agents, such as human serum albumin (HSA), may be added to the therapeutic or imaging composition to stabilize the antibody conjugates.

The compositions of the invention may be administered using any medically appropriate procedure, e.g., intravascular (intravenous, intraarterial, intracapillary) administration, injection into the lymph nodes, etc. Intravascular injection may be by intravenous or intraarterial injection. The effective amount of the therapeutic compositions to be given to a particular patient will depend on a variety of factors, several of which will be different from patient to patient. A competent clinician will be able to determine an effective amount of a therapeutic composition to administer to a patient to retard the growth and promote the death of tumor cells. Dosage of the agents will depend on the treatment of the tumor, route of administration, the nature of the therapeutics, sensitivity of the tumor to the therapeutics, etc. Utilizing $LD_{50}$ animal data, and other information available for the conjugated cytotoxic or imaging moiety, a clinician can determine the maximum safe dose for an individual, depending on the route of administration. For instance, an intravenously administered dose may be more than an locally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic or imaging composition in the course of routine clinical trials.

Typically the dosage will be 0.001 to 100 milligrams of antibody per kilogram subject body weight. The ratio of anti-CD47 to the second agent may range from 1:100; 1:50; 1:10; 1:5; 1:2; 1:1; 2:1; 5:1; 10:1; 50:1; 100:1. The agents can be administered to the subject in a series of more than one administration. For therapeutic compositions, regular periodic administration (e.g., every 2-3 days) will sometimes be required, or may be desirable to reduce toxicity. For therapeutic compositions which will be utilized in repeated-dose regimens, antibody moieties which do not provoke HAMA or other immune responses are preferred.

In addition to these therapeutic methods, depletion of cancer stem cells is useful in the treatment of cancer. Depletion can be achieved by several methods. Depletion is defined as a reduction in the target population by up to about 30%, or up to about 40%, or up to about 50%, or up to about 75% or more.

An effective depletion is usually determined by the sensitivity of the particular disease condition to the levels of the target population. Thus in the treatment of certain conditions a depletion of even about 20% could be beneficial.

A CD47 specific agent that specifically depletes the targeted cancer stem cells is used to contact the patient blood in vitro or in vivo, wherein after the contacting step, there is a reduction in the number of viable cancer stem cells in the targeted population. An effective dose of antibodies for such a purpose is sufficient to decrease the targeted population to the desired level, for example as described above. Antibodies for such purposes may have low antigenicity in humans or may be humanized antibodies.

In one embodiment of the invention, antibodies for depleting target population are added to patient blood in vivo. In another embodiment, the antibodies are added to the patient blood ex vivo. Beads coated with the antibody of interest can be added to the blood, target cells bound to these beads can then be removed from the blood using procedures common in the art. In one embodiment the beads are magnetic and are removed using a magnet. Alternatively, when the antibody is biotinylated, it is also possible to indirectly immobilize the antibody onto a solid phase which has adsorbed avidin, streptavidin, or the like. The solid phase, usually agarose or sepharose beads are separated from the blood by brief centrifugation. Multiple methods for tagging antibodies and removing such antibodies and any cells bound to the antibodies are routine in the art. Once the desired degree of depletion has been achieved, the blood is returned to the patient. Depletion of target cells ex vivo decreases the side effects such as infusion reactions associated with the intravenous administration. An additional advantage is that the repertoire of available antibodies is expanded significantly as this procedure does not have to be limited to antibodies with low antigenicity in humans or humanized antibodies.

Example 1

CD47 is a Marker of Myeloid Leukemias

Materials and Methods
Immunohistochemistry.
Cytospins of double sorted myeloid progenitor populations (CMP, GMP), IL-3Rα high CD45 RA+ cells and CD14+c-kit+lin– cells were performed using a Shandon cytospin apparatus. Cytospins were stained with Giemsa diluted 1/5 with H2O for 10 min followed by staining with May-Grunwald for 20 minutes. Cytospins were analyzed with the aid of a Zeiss microscope.

Human Bone Marrow and Peripheral Blood Samples.
Normal bone marrow samples were obtained with informed consent from 20-25 year old paid donors who were hepatitis A, B, C and HIV negative by serology (All Cells). CMML bone marrow samples were obtained with informed consent, from previously untreated patients, at Stanford University Medical Center.

Human Bone Marrow HSC and Myeloid Progenitor Flow-Cytometric Analysis and Cell Sorting.
Mononuclear fractions were extracted following Ficoll density centrifugation according to standard methods and analyzed fresh or subsequent to rapid thawing of samples previously frozen in 90% FCS and 10% DMSO in liquid nitrogen. In some cases, CD34+ cells were enriched from mononuclear fractions with the aid of immunomagnetic beads (CD34+ Progenitor Isolation Kit, Miltenyi Biotec, Bergisch-Gladbach, Germany). Prior to FACS analysis and sorting, myeloid progenitors were stained with lineage marker specific phycoerythrin (PE)-Cy5-conjugated antibodies including CD2 RPA-2.10; CD11b, ICRF44; CD20, 2H7; CD56, B159; GPA, GA-R2 (Becton Dickinson-PharMingen, San Diego), CD3, S4.1; CD4, S3.5; CD7, CD7-6B7; CD8, 3B5; CD10, 5-1B4, CD14, TUK4; CD19, SJ25-C1 (Caltag, South San Francisco, Calif.) and APC-conjugated anti-CD34, HPCA-2 (Becton Dickinson-PharMingen), biotinylated anti-CD38, HIT2 (Caltag) in addition to PE-conjugated anti-IL-3Rα, 9F5 (Becton Dickinson-PharMingen) and FITC-conjugated anti-CD45RA, MEM56 (Caltag) followed by staining with Streptavidin-Texas Red to visualize CD38-BIO stained cells and resuspension in propidium iodide to exclude dead cells. Unstained samples and isotype controls were included to assess background fluorescence.

Following staining, cells were analyzed and sorted using a modified FACS Vantage (Becton Dickinson Immunocytometry Systems, Mountain View, Calif.) equipped with a 599 nm dye laser and a 488 nm argon laser. Double sorted progenitor cells (HSC) were identified as CD34+CD38+ and lineage negative. Common myeloid progenitors (CMP) were identified based on CD34+CD38+IL-3Rα+CD45RA–lin– staining and their progeny including granulocyte/macrophage progenitors (GMP) were CD34+CD38+IL-3Rα+CD45RA+ while megakaryocyte/erythrocyte progenitors (MEP) were identified based on CD34+CD38+IL-3Rα–CD45RA–lin– staining.

CD47 Expression by Normal versus Myeloproliferative and AML Progenitors

Peripheral blood and bone marrow samples were obtained with informed consent from patients with myeloproliferative disorders and acute myelogenous leukemia at Stanford University Medical Center according to Stanford IRB and HIPAA regulations. Peripheral blood or bone marrow mononuclear cells (1-5×10$^6$ cells) were stained with lineage cocktail as above but excluding CD7, CD11b and CD14. Subsequently, samples were stained with CD14 PE (1/25), CD47 FITC (1/25), CD38 Bio (Bio) and c-kit APC (1/25) or CD34 APC or FITC (1/50) for 45 min followed by washing and staining with Streptavidin Texas Red (1/25) for 45 min and finally resuspension in propidium iodide.

Discussion

Here we show that CD47 overexpression is characteristic of progression of human myeloproliferative disorders to AML (see FIGS. 1-5B). CD47 controls integrin function but also the ability of macrophages to phagocytose cells, depending on the level of CD47 expression. Thus, aberrant CD47 expression may allow LSC to evade both innate and adaptive host immunity.

Human CD47 expression analysis was performed via FACS on human normal, pre-leukemic myeloproliferative disorder (MPD) or AML HSC, progenitors and lineage positive cells derived from marrow or peripheral blood. MPD samples (n=63) included polycythemia vera (PV; n=15), post-polycythemic myeloid metaplasia/myelofibrosis (PPMM/MF; n=5), essential thrombocythemia (ET; n=8), atypical chronic myelogenous leukemia (aCML; n=2), CML (n=7), chronic eosinophilic leukemia (CEL; n=1), chronic myelomonocytic leukemia (CMML; n=13) and acute myelogenous leukemia (AML; n=12). As we have observed with the transgenic leukemic mouse models, progression of human myeloproliferative disorders to AML (n=12) was associated with an expansion of the GMP pool (70.6%+/–S.D. 2.15) compared with normal bone marrow (14.7%+/–S.D. 2.3). Furthermore, FACS analysis revealed that CD47 expression first increased 1.7 fold in AML compared with normal HSC and then increased to 2.2 fold greater than normal with commitment of AML progenitors to the myeloid lineage. CD47 was over-expressed by AML primitive progenitors and their progeny but not by the majority of MPD (MFI 2.3+/–S.D. 0.43) compared with normal bone marrow (MFI 1.9+/–S.D. 0.07). Thus, increased CD47 expression is a useful diagnostic marker for progression to AML and in addition represents a novel therapeutic target.

Example 2

Human and Mouse Leukemias Upregulate CD47 to Evade Macrophage Killing

CD47 Facilitates Engraftment, Inhibits Phagocytosis, and is More Highly Expressed on AML LSC.

We determined expression of CD47 on human AML LSC and normal HSC by flow cytometry. HSC (Lin–CD34+CD38–CD90+) from three samples of normal human mobilized peripheral blood and AML LSC (Lin–CD34+CD38–CD90–) from seven samples of human AML were analyzed for surface expression of CD47. CD47 was expressed at low levels on the surface of normal HSC; however, on average, it was approximately 5-fold more highly expressed on AML LSC, as well as bulk leukemic blasts.

Anti-Human CD47 Monoclonal Antibody Stimulates Phagocytosis and Inhibits Engraftment of AML LSC.

Figure 6A:
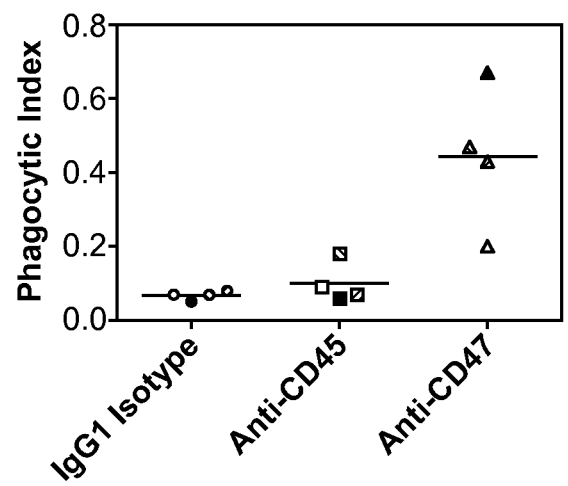
FIG. 6. Anti-CD47 Antibody stimulates in vitro macrophage phagocytosis of primary human AML LSC. AML LSC were purified by FACS from four primary human AML samples, labeled with the fluorescent dye CFSE, and incubated with human peripheral blood macrophages either in the presence of an isotype control, isotype matched anti-CD45, or anti-CD47 antibody. (A) These cells were assessed by immunofluorescence microscopy for the presence of fluorescently-labeled LSC within the macrophages. The phagocytic index was determined for each condition by calculating the number of ingested cells per 100 macrophages. (B) The macrophages were harvested, stained with a fluorescently labeled anti-human macrophage antibody, and analyzed by flow cytometry. hMac+CFSE+ double positive events identify macrophages that have phagocytosed CFSE-labeled LSC. Each sample is represented by a different color.
Figure 6B:
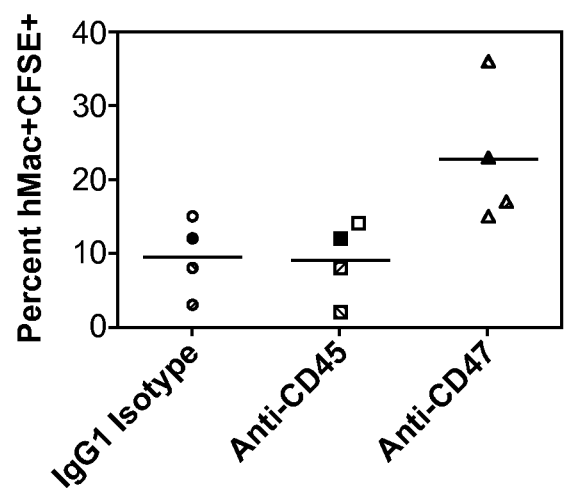

In order to test the model that CD47 overexpression on AML LSC prevents phagocytosis of these cells through its interaction with SIRPα on effector cells, we have utilized a monoclonal antibody directed against CD47 known to disrupt the CD47-SIRPα interaction. The hybridoma producing a mouse-anti-human CD47 monoclonal antibody, termed B6H12, was obtained from ATCC and used to produce purified antibody. First, we conducted in vitro phagocytosis assays. Primary human AML LSC were purified by FACS from two samples of human AML, and then loaded with the fluorescent dye CFSE. These cells were incubated with mouse bone marrow-derived macrophages and monitored using immunofluorescence microscopy and flow cytometry to identify phagocytosed cells. In both cases, no phagocytosis was observed in the presence of an isotype control antibody; however, significant phagocytosis was detected with the addition of the anti-CD47 antibody (FIG. 6). Thus, blockage of human CD47 with a monoclonal antibody is capable of stimulating the phagocytosis of these cells by mouse macrophages.

Figure 7A:
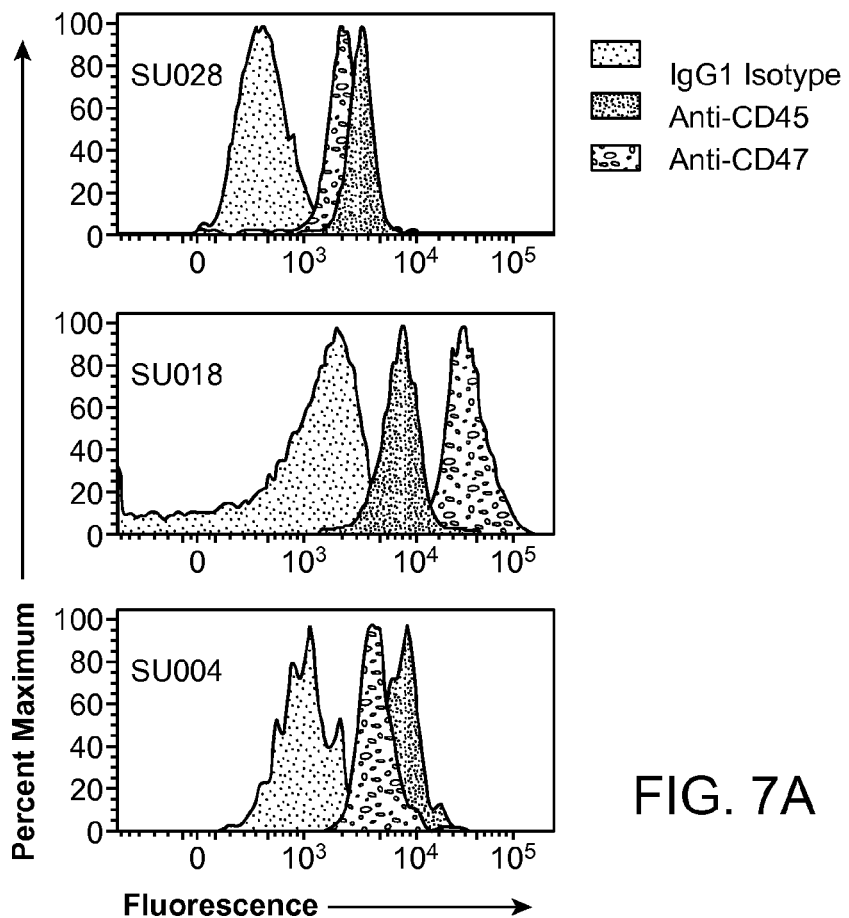
FIG. 7A-B: A Monoclonal Antibody Directed Against Human CD47 Inhibits AML LSC Engraftment In Vivo. Three primary human AML samples were incubated with IgG1 isotype control, anti-CD45 IgG1, or anti-CD47 IgG1 antibody (B6H12.2) prior to transplantation into newborn NOG mice. A portion of the cells was analyzed for coating by staining with a secondary anti-mouse IgG antibody and analyzed by flow cytometry (A). 13 weeks later, mice were sacrificed and the bone marrow was analyzed for the percentage of human CD45+CD33+ myeloid leukemia cells by flow cytometry (B). The difference in mean engraftment between anti-CD47-coated cells and both isotype ($p<0.001$) and anti-CD45 ($p=0.003$) coated cells was statistically significant.
Figure 7B:
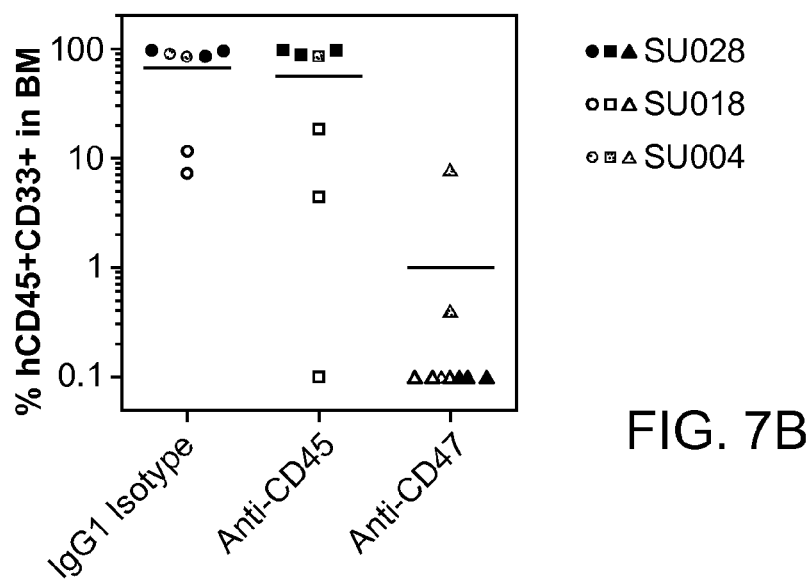

We next investigated the ability of the anti-CD47 antibody to inhibit AML LSC engraftment in vivo. Two primary human AML samples were either untreated or coated with the anti-CD47 antibody prior to transplantation into NOG newborn mice. 13 weeks later, the mice were sacrificed and analyzed for human leukemia bone marrow engraftment by flow cytometry (FIG. 7). The control mice demonstrated leukemic engraftment while mice transplanted with the anti-CD47-coated cells showed little to no engraftment. These data indicate that blockade of human CD47 with a monoclonal antibody is able to inhibit AML LSC engraftment.

Tumor progression is characterized by several hallmarks, including growth signal independence, inhibition of apoptosis, and evasion of the immune system, among others. We show here that expression of CD47, a ligand for the macrophage inhibitory signal regulatory protein alpha (SIRPα) receptor, is increased in human and mouse myeloid leukaemia and allows cells to evade phagocytosis and increase their tumorigenic potential. CD47, also known as integrin associated protein (IAP), is an immunoglobulin-like transmembrane pentaspanin that is broadly expressed in mammalian tissues.

We provide evidence that CD47 is upregulated in mouse and human myeloid leukaemia stem and progenitor cells, as well as leukemic blasts. Consistent with a biological role for CD47 in myeloid leukaemia development and maintenance, we demonstrate that ectopic over-expression of CD47 allows a myeloid leukaemia cell line to grow in mice that are T, B, and NK-cell deficient, whereas it is otherwise cleared rapidly when transplanted into these recipients. The leukemogenic potential of CD47 is also shown to be dose-dependent, as higher expressing clones have greater tumor forming potential than lower expressing clones. We also show that CD47 functions in promoting leukemogenesis by inhibiting phagocytosis of the leukemic cells by macrophages.

CD47 is significantly upregulated in leukemic $Fas^{lpr/lpr} \times$ hMRP8bcl2 transgenic bone marrow, and in leukemic hMRP8bcr/abl×hMRP8bcl2 mice. Transcripts for CD47 are increased in leukemic hMRP8bcr/abl×hMRP8bcl2 bone marrow 3-4 fold by quantitative RT-PCR and 6-7 fold in c-Kit enriched leukemic marrow relative to healthy hMRP8bcl2+ bone marrow (FIG. 8e). Leukemic spleen had an expansion of the granulocyte macrophage progenitor (GMP) population as well as c-Kit+Sca-1+Lin− stem and progenitor subsets relative to control mice, which were of the same genotype as leukemic mice but failed to develop disease (FIG. 8a-d). Expression levels for CD47 protein were found to begin increasing in leukemic mice relative to control mice at the stage of the Flk2−CD34−c-Kit+Sca-1+Lin− long-term hematopoietic stem cell (LT-HSC) (FIG. 8f). This increased level of expression was maintained in GMP and Mac-1+ blasts, but not megakaryocyte/erythroid restricted progenitors (MEP) (FIG. 8f). The increase in CD47 between leukemic and normal cells was between 3 to 20 fold. All mice that developed leukaemia that we have examined from hMRP8bcr/abl×hMRP8bcl2 primary (n=3) and secondary transplanted mice (n=3), $Fas^{lpr/lpr} \times$hMRP8bcl2 primary (n=14) and secondary (n=19) mice, and hMRP8bcl2× hMRP8bcl2 primary (n=3) and secondary (n=12) mice had increased CD47 expression. We have also found increased CD47 expression in mice that received p210bcr/abl retrovirally-transduced mouse bone marrow cells that developed leukemia.

Figure 9A:
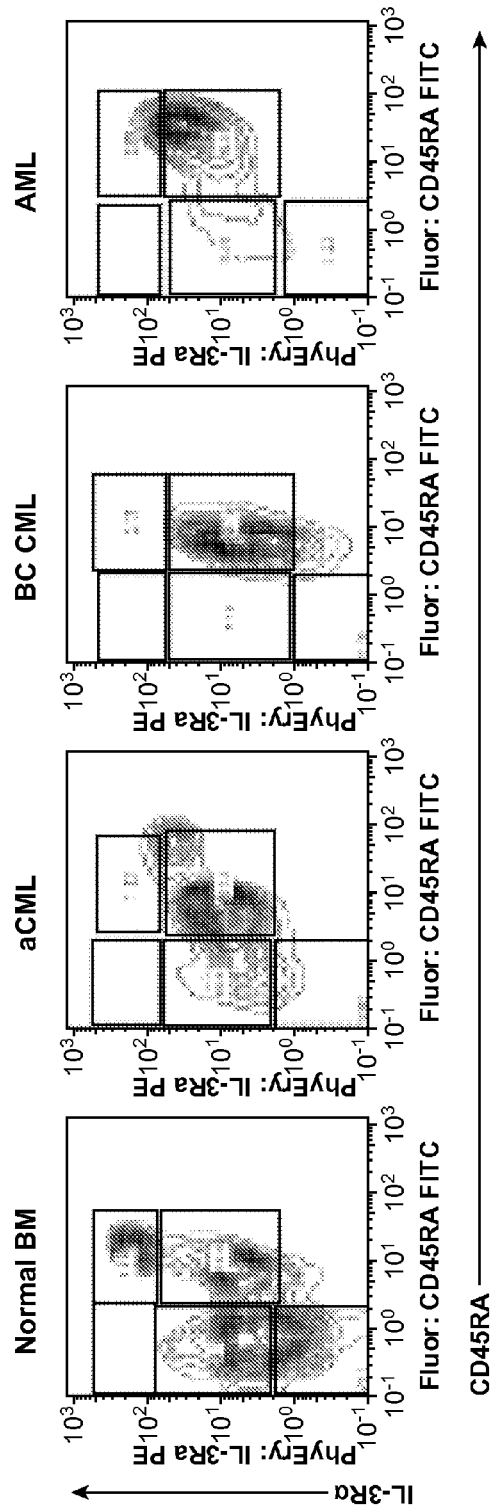
FIG. 9A-C. GMP expansion and CD47 upregulation in human myeloid leukemia. a) Representative FACS plots of myeloid progenitors (CD34+CD38+Lin−) including common myeloid progenitors (CMP), megakaryocyte-erythroid progenitors (MEP) and granulocyte-macrophage progenitors (GMP) in normal bone marrow (BM) versus aCML, BC CML and AML. b) Comparative FACS histograms of CD47 expression by normal (red; n=6) and acute myelogenous leukemic (AML, blue; n=6) hematopoietic stem cells (HSC; CD34+CD38−CD90+Lin−) and progenitors (CD34+CD38+Lin−). c) Comparative FACS histograms of CD47 expression by normal (red) and chronic myelogenous leukemia hematopoietic stem cells (HSC; CD34+CD38−CD90+Lin) and committed progenitors (CD34+CD38+Lin−). Upper panel: Normal (n=7) versus chronic phase CML (n=4) HSC, progenitors and lineage positive cells. Middle panel: Normal (n=7) versus accelerated phase CML (n=7) HSC, progenitors and lineage positive cells. Lower panel: Normal (n=7) versus blast crisis CML (n=4) HSC, progenitors and lineage positive cells.
Figure 9B:
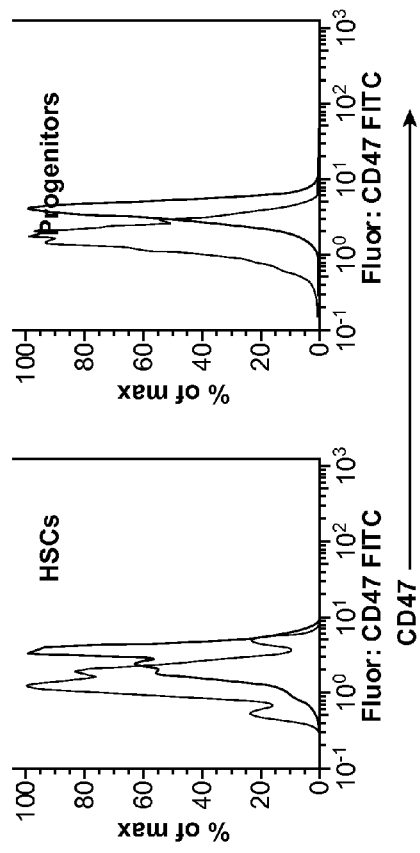
Figure 9C:
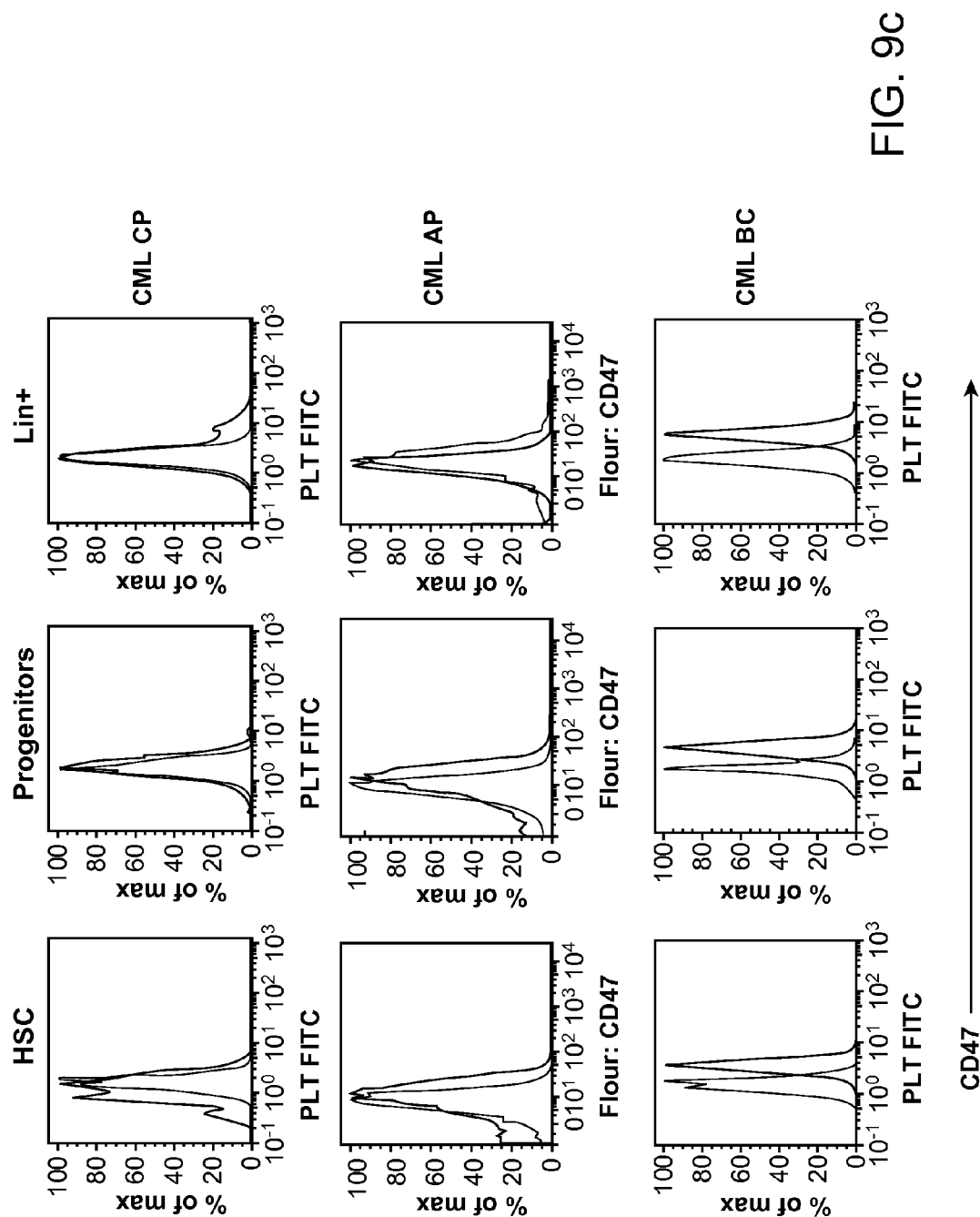

FACS-mediated analysis of human hematopoietic progenitor populations was performed on blood and marrow derived from normal cord blood and mobilized peripheral blood (n=16) and myeloproliferative disorders (MPDs) including polycythemia vera (PV; n=16), myelofibrosis (MF; n=5), essential thrombocythemia (ET; n=7), chronic myelomonocytic leukaemia (CMML; n=11) and atypical chronic myeloid leukaemia (aCML; n=1) as well as blast crisis phase chronic myeloid leukaemia (CML; n=19), chronic phase CML (n=7) and acute myelogenous leukaemia (AML; n=13). This analysis demonstrated that granulocyte-macrophage progenitors (GMP) expanded in MPDs with myeloid skewed differentiation potential including atypical CML, proliferative phase CMML and acute leukaemia including blast crisis CML and AML (FIG. 9a). AML HSC and progenitors uniformly exhibited higher levels of CD47 expression compared with normal controls (FIG. 9b); every sample from BC-CML and AML had elevated levels of CD47. Moreover, progression from chronic phase CML to blast crisis was associated with a significant increase in CD47 expression (FIG. 9c).

Using the methods described in this study, we have found that human CD47 protein expression in CML-BC increased 2.2 fold in CD90+CD34+CD38−Lin− cells relative to normal ($p=6.3\times10^{-5}$), 2.3 fold in CD90−CD34+CD38−Lin− cells relative to normal ($p=4.3\times10^{-5}$), and 2.4 fold in CD 34+CD38+Lin− cells ($p=7.6\times10^{-6}$) (FIGS. 9b-9c); however, using a newer optimized staining protocol we have observed that CD47 is increased approximately 10 fold in AML and BC-CML compared to normal human HSCs and progenitors.

It was then asked whether forced expression of mouse CD47 on human leukemic cells would confer a competitive advantage in forming tumors in mice. MOLM-13 cells, which are derived from a patient with AML 5a, were transduced with Tet-MCS-IRES-GFP (Tet) or Tet-CD47-MCS-IRES-GFP (Tet-CD47), and stable integrants were propagated on the basis of GFP expression. The cells were then transplanted intravenously in a competitive setting with untransduced MOLM-13 cells into T, B, and NK deficient recombination activating gene 2, common gamma chain deficient (RAG2−/−, Gc−/−) mice. Only cells transduced with Tet-CD47 were able to give rise to tumors in these mice, efficiently engrafting bone marrow, spleen and peripheral blood. The tumors were also characterized by large tumor burden in the liver, which is particularly significant because the liver is thought to have the highest number of macrophages of any organ, with estimates that Kupffer cells may comprise 80% of the total tissue macrophage population. These cells also make up 30% of the sinusoidal lining, thereby strategically placing them at sites of entry into the liver. Hence, significant engraftment there would have to disable a macrophage cytotoxic response. In addition to developing tumor nodules, the Tet-CD47 MOLM-13 cells exhibited patterns of hepatic involvement typically seen with human AML, with leukemic cells infiltrating the liver with a sinusoidal and perivenous pattern. Overall, Tet-CD47 MOLM-13 transplanted mice died more quickly than Tet MOLM-13 transplanted mice, which had virtually no engraftment of leukemic cells in hematopoietic tissues. Tet-MOLM-13 mice still had significant mortality, most likely due to localized growth at the site of injection (retro-orbital sinus) with extension into the brain.

Complete lack of CD47 has been shown to result in phagocytosis of transplanted murine erythrocytes and leukocytes, via lack of interaction with SIRPα on macrophages. Thus, we tested whether over-expression of CD47 could prevent phagocytosis of live, unopsonized MOLM-13 cells. We incubated Tet or Tet-CD47 MOLM-13 cells with bone marrow derived macrophages (BMDM) for 2-24 hours and assessed phagocytosis by counting the number of ingested GFP+ cells under a microscope or by evaluating the frequency of GFP+ macrophages using a flow cytometer. Expression of CD47 dramatically lowered macrophage clearance of these cells at all time points tested, whereas Tet-MOLM-13 were quickly phagocytosed in a manner that increased over time. We also injected MOLM-13 cells into mice and analyzed hematopoietic organs 2 hours later for evidence of macrophage phagocytosis. Macrophages in bone marrow, spleen, and liver all had higher GFP+ fraction when injected with Tet MOLM-13 cells as compared to CD47 expressing cells. This indicates that CD47 over-expression can compensate for pro-phagocytic signals already present on leukemic cells, allowing them to survive when they would otherwise be cleared by macrophages.

To model the tumorigenic effect of having high versus low CD47 expression, we sorted clones of murine CD47 expressing MOLM-13 cells into high and low expressers. When adjusted for cell size, CD47 density on the CD47$^{lo}$ MOLM-13 cells was approximately equal to mouse bone marrow cells, whereas CD47$^{hi}$ MOLM-13 cells had approximately 9 fold higher expression, an increase commensurate with the change seen in CD47 expression on primary leukemic cells compared to their normal counterparts. When high or low expressing cells were transplanted into recipients, only mice transplanted with high expressing cells succumbed to disease by 75 days of age. Furthermore, organomegaly was more pronounced in mice transplanted with high expressing cells. Mice receiving CD47$^{lo}$ MOLM-13 cells still had notable liver masses. However, the masses were invariably 1-2 large nodes that were well-encapsulated and physically segregated from the liver parenchyma, in marked contrast to tumor masses from CD47hi MOLM-13 cells which consisted of hundreds of small masses scattered throughout the parenchyma. Thus, these large tumor masses consist of cells which have found macrophage free-niches to grow in separate from the main organ body. As expected, the infiltration of MOLM-13 cells in bone marrow and spleen of recipient mice was much higher for mice transplanted with CD47$^{hi}$ MOLM-13 cells as well. We also examined the level of CD47 expression in two mice that received CD47$^{lo}$ MOLM-13 cells but had significant marrow engraftment. In both cases, the persisting cells after 75 days had much higher levels of CD47 than the original line, indicating that a strong selection pressure exists in vivo for high levels of CD47 expression on leukemic cells. In total, these data indicate that CD47 expression level is a significant factor in tumorigenic potential, and that in a heterogeneous population of leukemic cells, strong selection exists for those clones with high CD47 expression.

We then asked if higher CD47 expression level would provide added protection against macrophage phagocytosis. We performed an in vitro phagocytosis assay with CD47$^{hi}$ and CD47$^{lo}$ MOLM-13 red fluorescent protein (RFP) expressing cells. After incubation with macrophages, far greater numbers of CD47$^{lo}$ cells were phagocytosed as compared to CD47$^{hi}$ cells. If phagocytic indices are compared for control MOLM-13 cells, bulk (un-sorted) CD47 MOLM-13 cells, CD47$^{lo}$, and CD47$^{hi}$ MOLM-13 cells, then a direct correlation between CD47 expression level and ability to evade phagocytosis can be seen. Furthermore, when CD47$^{lo}$ RFP MOLM-13 cells and CD47$^{hi}$ GFP MOLM-13 cells were co-incubated with macrophages in the same wells, the low expressing cells were far more likely to be phagocytosed. Thus, in a mixed population of cells with varying levels of CD47 expression, the low expressing cells are more likely to be cleared by phagocytic clearance over time.

We also titrated CD47 expression using another method. Since CD47 is expressed in MOLM-13 cells using a Tet-OFF system, we utilized the Tet-inducible promoter element to control expression of CD47 in MOLM-13 cells. Beginning two weeks after transplantation with CD47$^{hi}$ MOLM-13 cells, a cohort of mice was given doxycycline and followed for up to 75 days post-transplant. During this time course, none of the mice given doxycycline succumbed to disease or had large infiltration of MOLM-13 cells in hematopoietic organs. At the doses of doxycycline used in this experiment, muCD47 expression in MOLM-13 cells was reduced to levels below that of normal mouse bone marrow, but notably not completely absent. Thus, a sustained high level of CD47 expression is required for robust MOLM-13 survival in hematopoietic organs.

Many examples of tumor clearance by T, B, and NK cells have been described in the literature, indicating that a healthy immune system is essential for regulating nascent tumor growth. However, to date, few examples have been produced indicating that macrophage-mediated phagocytosis can check tumor development. Collectively, our studies reveal that ectopic expression of CD47 can enable otherwise immunogenic tumor cells to grow rapidly in a T, B, and NK-cell deficient host. Furthermore, this is likely to reflect a mechanism used by human myeloid leukemias to evade the host immune system since CD47 is consistently upregulated in murine and human myeloid leukemias, including all forms of chronic and acute myeloid leukaemia tested thus far. Thus, it appears likely that tumor cells are capable of being recognized as a target by activated macrophages and cleared through phagocytosis. By upregulating CD47, cancers are able to escape this form of innate immune tumor surveillance.

This form of immune evasion is particularly important since these cancers often occupy sites of high macrophage infiltration. CD47 was first cloned as an ovarian tumor cell marker, indicating that it may play a role in preventing phagocytosis of other tissue cancers as well. Furthermore, solid tumors often metastasize to macrophage rich tissues such as liver, lung, bone marrow, and lymph nodes, indicating that they must be able to escape macrophage-mediated killing in those tissues. Finding methods to disrupt CD47-SIRPα interaction may thus prove broadly useful in developing novel therapies for cancer. Preventing CD47-SIRPα interaction is doubly effective since antigens from phagocytosed tumor cells may be presented by macrophages to activate an adaptive immune response, leading to further tumor destruction.

Methods

Mice.

hMRP8bcrabl, hMRP8bcl2, and Fas$^{lpr/lpr}$ transgenic mice were created as previously described and crossed to obtain double transgenics. hMRP8bcl2 homozygotes were obtained by crossing heterozygote mice to each other. C57Bl/6 Ka mice from our colony were used as a source of wild-type cells. For transplant experiments, cells were transplanted into C57Bl/6 RAG2$^{-/-}$ common gamma chain (Gc)$^{-/-}$ mice given a radiation dose of 4 Gy using gamma rays from a cesium irradiator (Phillips). Primary mouse leukemias were transplanted into CD45.2 C57Bl6/Ka mice given a radiation dose of 9.5 Gy. Mice were euthanized when moribund.

Mouse Tissues.

Long bones were flushed with PBS supplemented with 2% fetal calf serum staining media (SM) Spleens and livers were dissociated using frosted glass slides in SM, then passed through a nylon mesh. All samples were treated with ACK lysis buffer to lyse erythrocytes prior to further analysis.

Quantitative RT-PCR Analysis.

Bone marrow was obtained from leukemic hMRP8bcr/abl×hMRP8bcl2 mice or hMRP8bcl2 control mice. Cells were c-Kit enriched using c-Kit microbeads and an autoMACS column (Miltenyi), RNA was extracted using Trizol reagent (Invitrogen) and reverse transcription performed using SuperScriptII reverse polymerase (Invitrogen). cDNA corresponding to approximately 1000 cells was used per PCR reaction. Quantitative PCR was performed with a SYBR green kit on an ABI Prism 7000 PCR (Applied Biosystems) machine at 50° C. for 2 minutes, followed by 95° C. for 10 minutes and then 40 cycles of 95° C. for 15 minutes followed by 60° C. for 1 minute. Beta-actin and 18S RNA were used as controls for cDNA quantity and results of CD47 expression were normalized. Sequences for 18S RNA forward and reverse primers were (SEQ ID NO:2) TTGACGGAAGGGCACCACCAG and (SEQ ID NO:3) GCACCACCACCCACGGAATCG, respectively, for beta-actin were (SEQ ID NO:4) TTCCTTCTTGGGTATGGAAT and (SEQ ID NO:5) GAGCAATGATCTTGATCCTC, and for CD47 were (SEQ ID NO:6) AGGCCAAGTCCAGAAGCATTC and (SEQ ID NO:7) AATCATTCTGCTGCTCGTTGC.

Human Bone Marrow and Peripheral Blood Samples.

Normal bone marrow samples were obtained with informed consent from 20-25 year old paid donors who were hepatitis A, B, C and HIV negative by serology (All Cells). Blood and marrow cells were donated by patients with chronic myelomonocytic leukemia (CMML), chronic myeloid leukemia (CML), and acute myelogenous leukemia (AML) and were obtained with informed consent, from previously untreated patients.

Cell Lines.

MOLM-13 cells were obtained from DSMZ. HL-60 and Jurkat cells were obtained from ATCC. Cells were maintained in Iscove's modified Dulbecco's media (IMDM) plus 10% fetal bovine serum (FBS) (Hyclone). To fractionate MOLM-13 cells into those with high and low CD47 expression, Tet-CD47 MOLM-13 cells were stained with anti-mouse CD47 Alexa-680 antibody (mIAP301). The highest and lowest 5% of mouse CD47 expressing cells was sorted on a BD FACSAria and re-grown in IMDM+10% FCS for 2 weeks. The cells were sorted for three more rounds of selection following the same protocol to obtain the high and low expressing cells used in this study. To obtain red fluorescent protein (RFP) constructs, the mCherry RFP DNA was cloned into Lentilox 3.7 (pLL3.7) empty vector. Lentivirus obtained from this construct was then used to infect cell lines.

Cell Staining and Flow Cytometry.

Staining for mouse stem and progenitor cells was performed using the following monoclonal antibodies: Mac-1, Gr-1, CD3, CD4, CD8, B220, and Ter119 conjugated to Cy5-PE (eBioscience) were used in the lineage cocktail, c-Kit PE-Cy7 (eBioscience), Sca-1 Alexa680 (e13-161-7, produced in our lab), CD34 FITC (eBioscience), CD16/32 (Fc-GRII/III) APC (Pharmingen), and CD135 (Flk-2) PE (eBioscience) were used as previously described to stain mouse stem and progenitor subsets. Mouse CD47 antibody (clone mIAP301) was assessed using biotinylated antibody produced in our lab. Cells were then stained with streptavidin conjugated Quantum Dot 605 (Chemicon). Samples were analyzed using a FACSAria (Beckton Dickinson).

For human samples, mononuclear fractions were extracted following Ficoll density centrifugation according to standard methods and analyzed fresh or subsequent to rapid thawing of samples previously frozen in 90% FCS and 10% DMSO in liquid nitrogen. In some cases, CD34+ cells were enriched from mononuclear fractions with the aid of immunomagnetic beads (CD34+ Progenitor Isolation Kit, Miltenyi Biotec, Bergisch-Gladbach, Germany). Prior to FACS analysis and sorting, myeloid progenitors were stained with lineage marker specific phycoerythrin (PE)-Cy5-conjugated antibodies including CD2 RPA-2.10; CD11b, ICRF44; CD20, 2H7; CD56, B159; GPA, GA-R2 (Becton Dickinson-PharMingen, San Diego), CD3, S4.1; CD4, S3.5; CD7, CD7-6B7; CD8, 3B5; CD10, 5-1B4, CD14, TUK4; CD19, SJ25-C1 (Caltag, South San Francisco, Calif.) and APC-conjugated anti-CD34, HPCA-2 (Becton Dickinson-PharMingen), biotinylated anti-CD38, HIT2 (Caltag) in addition to PE-conjugated anti-IL-3Rα, 9F5 (Becton Dickinson-PharMingen) and FITC-conjugated anti-CD45RA, MEM56 (Caltag) followed by staining with Streptavidin-Texas Red to visualize CD38-BIO stained cells.

Following staining, cells were analyzed using a modified FACS Vantage (Becton Dickinson Immunocytometry Systems, Mountain View, Calif.) equipped with a 599 nm dye laser and a 488 nm argon laser or a FACSAria. Hematopoietic stem cells (HSC) were identified as CD34+CD38+CD90+ and lineage negative. Anti-human CD47 FITC (clone B6H12, Pharmingen) was used to assess CD47 expression in all human samples. Fold change for CD47 expression was determined by dividing the average mean fluorescence intensity of CD47 for all the samples of CML-BC, CML-CP, or AML by the average mean fluorescence intensity of normal cells for a given cell population. Common myeloid progenitors (CMP) were identified based on CD34+CD38+IL-3Rα+CD45RA− lin− staining and their progeny including granulocyte/macrophage progenitors (GMP) were CD34+CD38+IL-3Rα+CD45RA+Lin− while megakaryocyte/erythrocyte progenitors (MEP) were identified based on CD34+CD38+IL-3Rα−CD45RA−Lin− staining.

To determine the density of mouse or human CD47, cells were stained with saturating amounts of anti-CD47 antibody and analyzed on a FACSAria. Since forward scatter is directly proportional to cell diameter, and density is equal to expression level per unit of surface area we used FloJo software to calculate geometric mean fluorescent intensity of the CD47 channel and divided by the geometric mean of the forward scatter value squared ($FSC^2$) to obtain an approximation for density of CD47 expression on the membrane.

Engraftment of MOLM-13 cells was assessed by using anti-human CD45 PE-Cy7 (Pharmingen), anti-mouse CD45.2 APC (clone AL1-4A2), and anti-mouse CD47 Alexa-680 (mIAP301). All samples were resuspended in propidium iodide containing buffer before analysis to exclude dead cells. FACS data was analyzed using FloJo software (Treestar).

Lentiviral Preparation and Transduction.

pRRL.sin-18.PPT.Tet07.IRES.GFP.pre, CMV, VSV, and tet trans-activator (tTA) plasmids were obtained from Luigi Naldini. The full length murine cDNA for CD47 form 2 was provided by Eric Brown (UCSF). The CD47 cDNA construct was ligated into the BamHI/NheI site of Tet-MCS-IRES-GFP. Plasmid DNA was transfected into 293T cells using standard protocols. The supernatant was harvested and concentrated using a Beckman LM-8 centrifuge (Beckman). Cells were transduced with Tet or Tet-CD47-MCS-IRES-GFP and tTA lentivirus for 48 hours. GFP+ cells were sorted to purity and grown for several generations to ensure stability of the transgenes.

Injections.

Cells were injected intravenously into the retro-orbital sinuses of recipient mice or via the tail vein as noted. For intra-femoral injections, cells were injected into the femoral cavity of anesthetized mice in a volume of 20 µl using a 27-gauge needle. An isofluorane gas chamber was used to anesthetize mice when necessary.

MOLM-13 Cell Engraftment.

Animals were euthanized when moribund and bone marrow, spleen, and liver harvested. Peripheral blood was obtained by tail bleed of the animals 1 hour prior to euthanization. Engraftment of MOLM-13 cells in marrow, spleen, and peripheral blood was determined as described above. Tumor burden in the liver was determined by calculating the area of each visible tumor nodule using the formula ((length in mm+width in mm)/2)*π. Area of each nodule was then added together per liver.

Doxycycline Administration.

Doxycycline hydrochloride (Sigma) was added to drinking water at a final concentration of 1 mg/mL. Drinking water was replaced every 4 days and protected from light. In addition, mice received a 10 µg bolus of doxycycline by i.p. injection once a week.

Bone Marrow Derived Macrophages (BMDM).

Femurs and tibias were harvested from C57Bl/6 Ka mice and the marrow was flushed and placed into a sterile suspension of PBS. The bone marrow suspension was grown in IMDM plus 10% FBS with 10 ng/mL of recombinant murine macrophage colony stimulating factor (MCSF, Peprotech) for 7-10 days.

In Vitro Phagocytosis Assays.

BMDM were harvested by incubation in trypsin/EDTA (Gibco) for 5 minutes and gentle scraping. Macrophages were plated at $5 \times 10^4$ cells per well in a 24-well tissue culture plate (Falcon). After 24 hours, media was replaced with serum-free IMDM. After an additional 2 hours, $2.5 \times 10^5$ Tet or Tet-CD47 MOLM-13 cells were added to the macrophage containing wells and incubated at 37 C.° for the indicated times. After co-incubation, wells were washed thoroughly with IMDM 3 times and examined under an Eclipse T5100 (Nikon) using an enhanced green fluorescent protein (GFP) or Texas Red filter set (Nikon). The number of GFP+ or RFP+ cells within macrophages was counted and phagocytic index was calculated using the formula: phagocytic index=number of ingested cells/(number of macrophages/100). At least 200 macrophages were counted per well. For flow cytometry analysis of phagocytosis macrophages were harvested after incubation with MOLM-13 cells using trypsin/EDTA and gentle scraping. Cells were stained with anti-Mac-1 PE antibody and analyzed on a BD FACSAria. Fluorescent and brightfield images were taken separately using an Eclipse T5100 (Nikon), a super high pressure mercury lamp (Nikon), an endow green fluorescent protein (eGFP) bandpass filter (Nikon) a Texas Red bandpass filter (Nikon), and a RT Slider (Spot Diagnostics) camera. Images were merged with Photoshop software (Adobe).

For in vivo assays, marrow from leg long bones, spleen, and liver were harvested 2 hours after injecting target cells into $RAG2^{-/-}$, $Gc^{-/-}$ mice. They were prepared into single cell suspensions in PBS plus 2% FCS. Cells were labeled with anti-human CD45 Cy7-PE and anti-mouse F4/80 biotin (eBiosciences). Secondary stain was performed with Streptavidin-APC (eBiosciences). Cells that were human CD45−, F4/80+ were considered to be macrophages, and GFP+ cells in this fraction was assessed.

Example 3

CD47 is an Independent Prognostic Factor and Therapeutic Antibody Target on Human Acute Myeloid Leukemia Cells Acute myelogenous leukemia (AML) is organized as a cellular hierarchy initiated and maintained by a subset of self-renewing leukemia stem cells (LSC). We hypothesized that increased CD47 expression on AML LSC contributes to pathogenesis by inhibiting their phagocytosis through the interaction of CD47 with an inhibitory receptor on phagocytes. We found that CD47 was more highly expressed on AML LSC than their normal counterparts, and that increased CD47 expression predicted worse overall survival in 3 independent cohorts of adult AML patients. Furthermore, blocking monoclonal antibodies against CD47 preferentially enabled phagocytosis of AML LSC by macrophages in vitro, and inhibited their engraftment in vivo. Finally, treatment of human AML-engrafted mice with anti-CD47 antibody eliminated AML in vivo. In summary, increased CD47 expression is an independent poor prognostic factor that can be targeted on human AML stem cells with monoclonal antibodies capable of stimulating phagocytosis of LSC.

Results

CD47 is More Highly Expressed on AML LSC than their Normal Counterparts and is Associated with the FLT3-ITD Mutation.

Figure 5A:
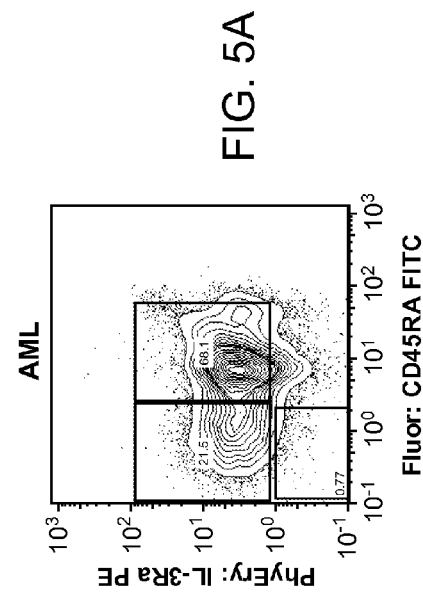
FIGS. 5A-5B. (A) Progenitor Profiles of Normal bone marrow (left) versus AML (right). (B) FACS analysis of human normal bone marrow (red) versus AML (blue) HSC, progenitor and lineage positive cell (blast) CD47 expression.
Figure 5B:
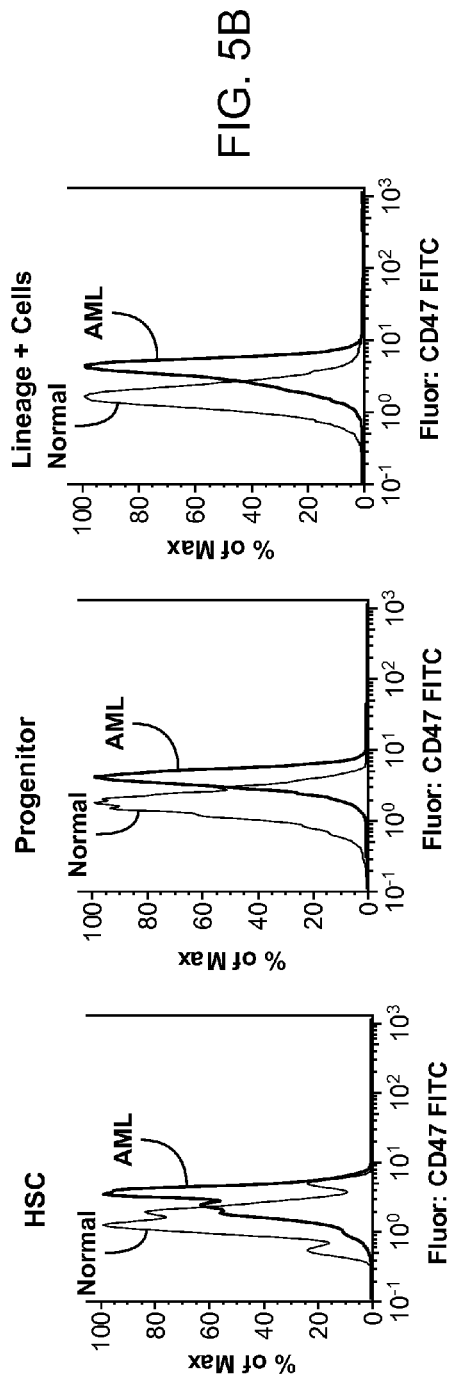

In our investigation of several mouse models of myeloid leukemia, we identified increased expression of CD47 on mouse leukemia cells compared to normal bone marrow. This prompted investigation of CD47 expression on human AML LSC and their normal counterparts. Using flow cytometry, CD47 was more highly expressed on multiple specimens of AML LSC than normal bone marrow HSC and MPP (FIG. 5). This increased expression extended to the bulk leukemia cells, which expressed CD47 similarly to the LSC-enriched fraction.

Examination of a subset of these samples indicated that CD47 surface expression correlated with CD47 mRNA expression. To investigate CD47 expression across morphologic, cytogenetic, and molecular subgroups of AML, gene expression data from a previously described cohort of 285 adult patients were analyzed (Valk et al., 2004 N Engl J Med 350, 1617-1628). No significant difference in CD47 expression among FAB (French-American-British) subtypes was found. In most cytogenetic subgroups, CD47 was expressed at similar levels, except for cases harboring t(8;21)(q22;q22), a favorable risk group which had a statistically significant lower CD47 expression. In molecularly characterized AML subgroups, no significant association was found between CD47 expression and mutations in the tyrosine kinase domain of FLT3 (FLT3-TKD), over-expression of EVI1, or mutations in CEBPA, NRAS, or KRAS. However, higher CD47 expression was strongly correlated with the presence of FLT3-ITD ($p<0.001$), which is observed in nearly one third of AML with normal karyotypes and is associated with worse overall survival. This finding was separately confirmed in two independent datasets of 214 and 137 AML patients (Table 1).

TABLE 1

Clinical and Molecular Characteristics of AML Samples from the Validation Cohort and Comparison Between Low CD47 and High CD47 Expression Groups

| Clinical Feature* | Overall n = 137 | Low CD47 n = 95 | High CD47 n = 37 | P† |
|---|---|---|---|---|
| Age, yrs. | | | | 0.26 |
| Median | 46 | 47 | 46 | |
| Range | 16-60 | 24-60 | 16-60 | |
| WBC, ×10⁹/L | | | | <0.01 |
| Median | 24 | 17 | 35 | |
| Range | 1-238 | 1-178 | 1-238 | |
| Centrally reviewed FAB Classification, no. (%) | | | | 0.29 |
| M0 | 11 (8) | 9 (9) | 2 (5) | |
| M1 | 28 (20) | 16 (17) | 2 (32) | |
| M2 | 36 (26) | 22 (23) | 11 (30) | |
| M4 | 33 (24) | 25 (26) | 8 (22) | |
| M5 | 19 (14) | 16 (17) | 3 (8) | |
| M6 | 2 (1) | 2 (2) | 0 (0) | |
| Unclassified | 6 (4) | 4 (4) | 0 (0) | |
| FLT3-ITD, no. (%) | | | | <0.05 |
| Negative | 84 (61) | 63 (66) | 17 (46) | |
| Positive | 53 (39) | 32 (34) | 20 (54) | |
| FLT3-TKD, no. (%) | | | | 0.24 |
| Negative | 109 (87) | 78 (89) | 27 (79) | |
| Positive | 17 (13) | 10 (11) | 7 (21) | |
| NPM1, no. (%) | | | | 0.10 |
| Wild-Type | 55 (45) | 41 (49) | 10 (30) | |
| Mutated | 66 (55) | 43 (51) | 23 (70) | |
| CEBPA, no. (%) | | | | 1 |
| Wild-Type | 100 (86) | 70 (86) | 27 (87) | |
| Mutated | 16 (14) | 11 (14) | 4 (13) | |
| MLL-PTD, no. (%) | | | | 1 |
| Negative | 121 (93) | 83 (92) | 34 (94) | |
| Positive | 9 (7) | 7 (8) | 2 (6) | |
| Event-free survival | | | | 0.004 |
| Median, mos. | 14 | 17.1 | 6.8 | |
| Diesease free at 3 yrs, % (95% CI) | 36 (27-44) | 41 (31-52) | 22 (8-36) | |

TABLE 1-continued

Clinical and Molecular Characteristics of AML Samples from the Validation Cohort and Comparison Between Low CD47 and High CD47 Expression Groups

| Clinical Feature* | Overall n = 137 | Low CD47 n = 95 | High CD47 n = 37 | P† |
|---|---|---|---|---|
| Overall survival | | | | 0.002 |
| Median, mos. | 18.5 | 22.1 | 9.1 | |
| Alive at 3 yrs, % (95% CI) | 39 (31-48) | 44 (33-55) | 26 (12-41) | |
| Complete remission rate, no. (%) | | | | |
| CR after 1st Induction, no. (%) | 60 (46%) | 46 (48%) | 14 (38%) | 0.33 |
| CR after 2nd Induction, no. (%) | 84 (74%) | 64 (75%) | 20 (69%) | 0.63 |
| Randomization to 2ndary consolidative therapy | | | | |
| Allogeneic-HSCT, no. (%) | 29 (22%) | 25 (26%) | 4 (11%) | 0.09 |
| Autologous-HSCT, no. (%) | 23 (17%) | 17 (18%) | 6 (16%) | 0.98 |

*Tabulated clinical and molecular characteristics at diagnosis. WBC indicates white blood cell count, FAB, French-American-British; FLT3-ITD, internal tandem duplication of the FLT3 gene (for 10 cases with missing FLT3-ITD status, the predicted FLT3-ITD status based on gene expression was substituted using method of Bullinger et al, 2008); FLT3-TKD, tyrosine kinase domain mutation of the FLT3 gene; NPM1, mutation of the NPM1 gene; MLL-PTD, partial tandem duplication of the MLL gene; and CEBPA, mutation of the CEBPA gene. CR, complete remission. CR was assessed both after first and second induction regimens, which comprised ICE (idarubicin, etoposide, cytarabine) or A-HAM (all-trans retinoic acid and high-dose cytarabine plus mitoxantrone). Autologous-HSCT; autologous transplantation; Allogeneic-HSCT, allogeneic transplantation.
†P value compares differences in molecular and clinical characteristics at diagnosis between patients with low and high CD47 mRNA expression values. CD47 expression was dichotomonized based on an optimal cut point for overall survival stratification that we identified on an independent microarray dataser published (Valk et al, 2004) as described in supplemental methods.

Identification and Separation of Normal and Leukemic Progenitors from the Same Patient Based on Differential CD47 Expression.

Figure 10A:
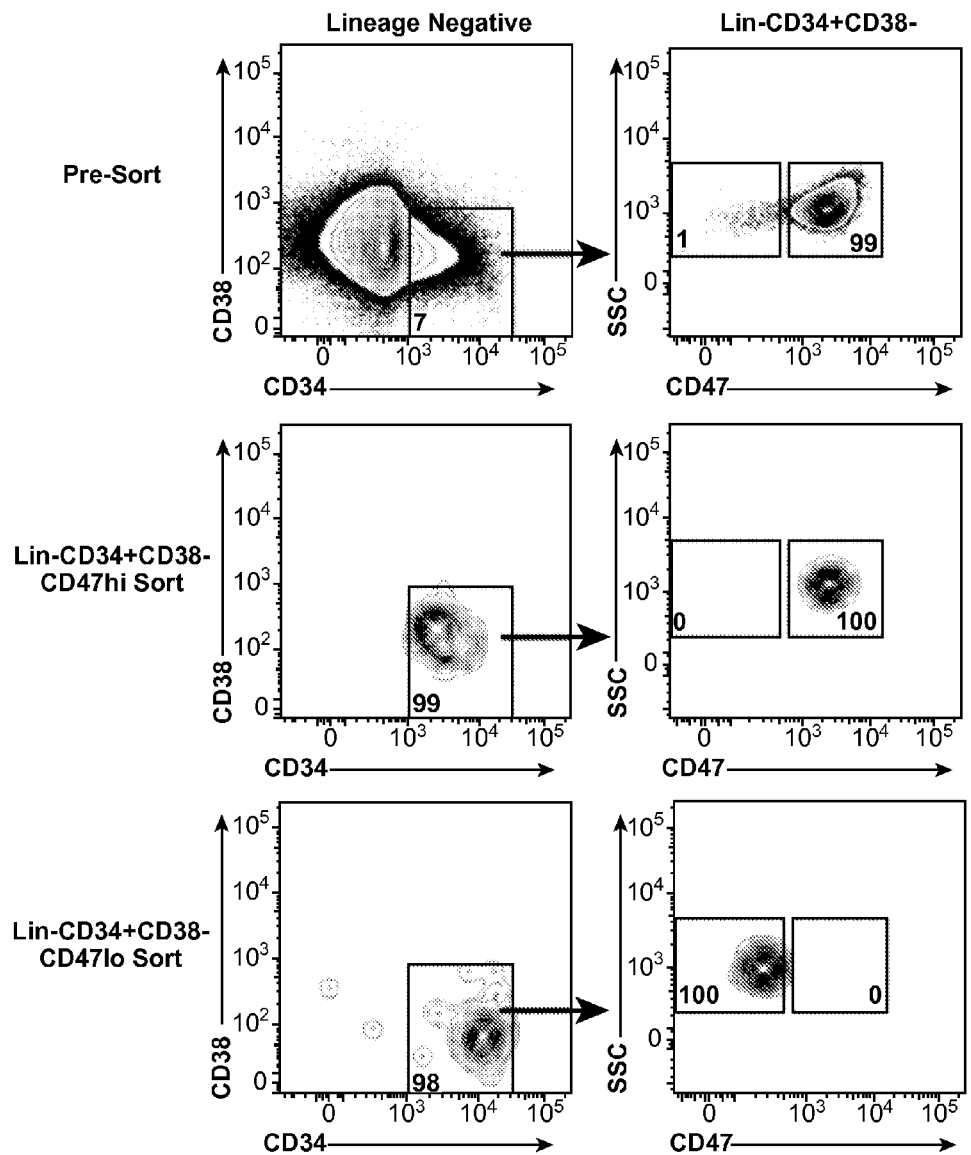
FIG. 10A-D: Identification and Separation of Normal and Leukemic Progenitors From the Same Patient Based On Differential CD47 Expression. A. CD47 expression on the Lin−CD34+CD38− LSC-enriched fraction of specimen SU008 was determined by flow cytometry. CD47hi- and CD47lo-expressing cells were identified and purified using FACS. The left panels are gated on lineage negative cells, while the right panels are gated on Lin−CD34+CD38− cells. B. Lin−CD34+CD38−CD47lo and Lin−CD34+CD38−CD47hi cells were plated into complete methylcellulose, capable of supporting the growth of all myeloid colonies. 14 days later, myeloid colony formation was determined by morphologic assessment. Representative CFU-G/M (left) and BFU-E (right) are presented. C. Lin−CD34+CD38−CD47lo cells were transplanted into 2 newborn NOG mice. 12 weeks later, the mice were sacrificed and the bone marrow was analyzed for the presence of human CD45+CD33+ myeloid cells and human CD45+CD19+ lymphoid cells by flow cytometry. D. Normal bone marrow HSC, bulk SU008 leukemia cells, Lin−CD34+CD38−CD47hi cells, Lin−CD34+CD38−CD47lo cells, or human CD45+ cells purified from the bone marrow of mice engrafted with Lin−CD34+CD38−CD47lo cells were assessed for the presence of the FLT3-ITD mutation by PCR. The wild type FLT3 and the FLT3-ITD products are indicated.

In the LSC-enriched Lin-CD34+CD38- fraction of specimen SU008, a rare population of CD47lo-expressing cells was detected, in addition to the majority CD47$^{hi}$-expressing cells (FIG. 10A). These populations were isolated by fluorescence-activated cell sorting (FACS) to >98% purity and either transplanted into newborn NOG mice or plated into complete methylcellulose. The CD47$^{hi}$ cells failed to engraft in vivo or form any colonies in vitro, as can be observed with some AML specimens.

Figure 10B:
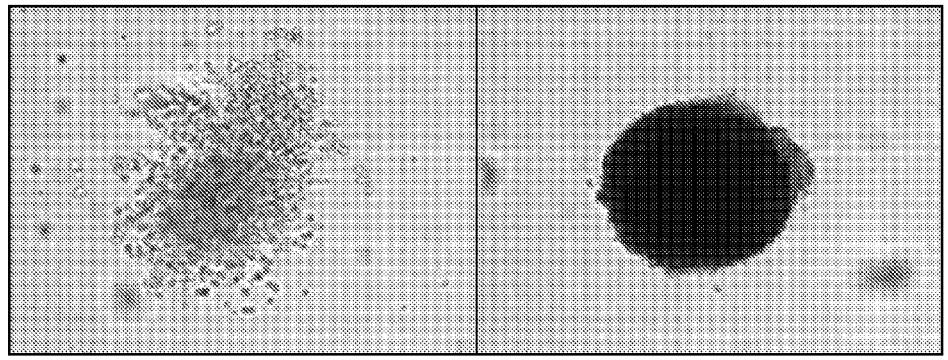
Figure 10C:
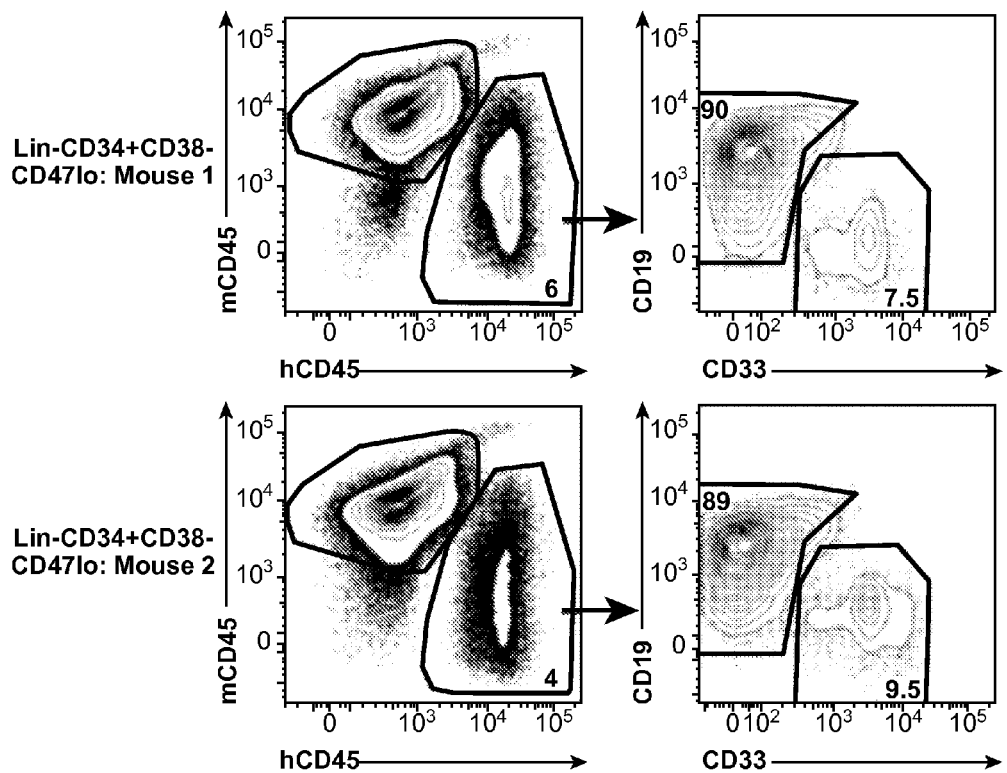
Figure 10D:
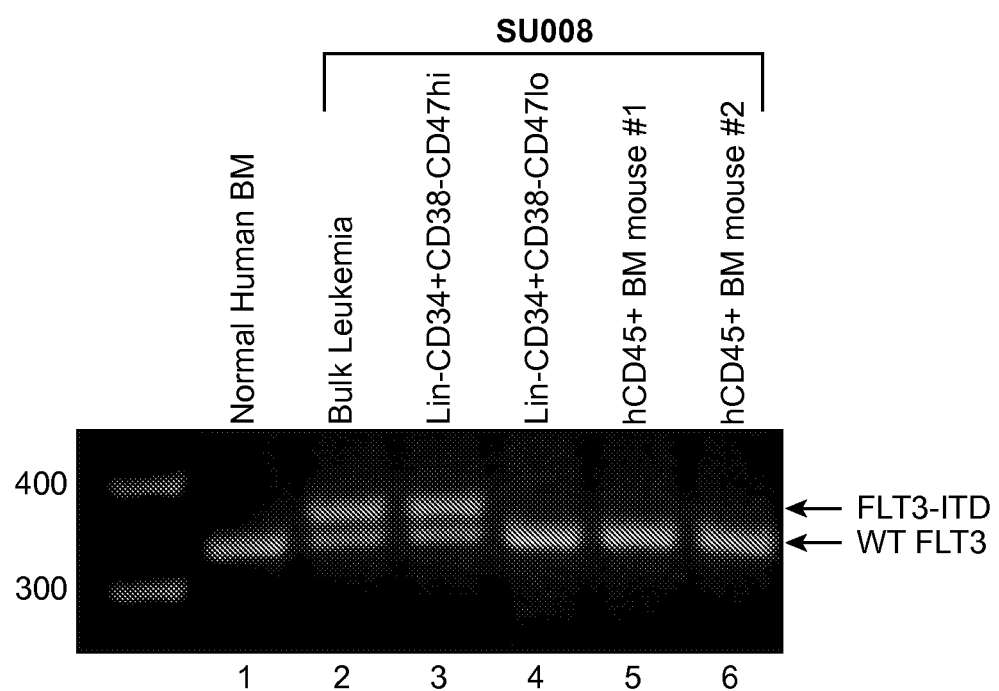

However, the CD47$^{lo}$ cells engrafted with normal myelo-lymphoid hematopoiesis in vivo and formed numerous morphologically normal myeloid colonies in vitro (FIG. 10B,C). This specimen harbored the FLT3-ITD mutation, which was detected in the bulk leukemia cells (FIG. 10D). The purified CD47$^{hi}$ cells contained the FLT3-ITD mutation, and therefore, were part of the leukemic clone, while the CD47$^{lo}$ cells did not. Human cells isolated from mice engrafted with the CD47$^{lo}$ cells contained only wild type FLT3, indicating that the CD47$^{lo}$ cells contained normal hematopoietic progenitors.

Increased CD47 Expression in Human AML is Associated with Poor Clinical Outcomes.

We hypothesized that increased CD47 expression on human AML contributes to pathogenesis. From this hypothesis, we predicted that AML with higher expression of CD47 would be associated with worse clinical outcomes. Consistent with this hypothesis, analysis of a previously described group of 285 adult AML patients with diverse cytogenetic and molecular abnormalities (Valk et al., 2004) revealed that a dichotomous stratification of patients into low CD47 and high CD47 expression groups was associated with a significantly increased risk of death in the high expressing group (p=0.03). The association of overall survival with this dichotomous stratification of CD47 expression was validated in a second test cohort of 242 adult patients (Metzeler et al., 2008 Blood) with normal karyotypes (NK-AML) (p=0.01).

Applying this stratification to a distinct validation cohort of 137 adult patients with normal karyotypes (Bullinger et al., 2008 Blood 111, 4490-4495), we confirmed the prognostic value of CD47 expression for both overall and event-free survival. Analysis of clinical characteristics of the low and high CD47 expression groups in this cross-validation cohort also identified statistically significant differences in white blood cell (WBC) count and FLT3-ITD status, and no differences in rates of complete remission and type of consolidative therapy including allogeneic transplantation (Table 1). Kaplan-Meier analysis demonstrated that high CD47 expression at diagnosis was significantly associated with worse event-free and overall survival. Patients in the low CD47 expression group had a median event-free survival of 17.1 months compared to 6.8 months in the high CD47 expression group, corresponding to a hazard ratio of 1.94 (95% confidence interval 1.30 to 3.77, p=0.004). For overall survival, patients in the low CD47 expression group had a median of 22.1 months compared to 9.1 months in the high CD47 expression group, corresponding to a hazard ratio of 2.02 (95% confidence interval 1.37 to 4.03, p=0.002). When CD47 expression was considered as a continuous variable, increased expression was also associated with a worse event-free (p=0.02) and overall survival (p=0.02).

Despite the association with FLT3-ITD, increased CD47 expression at diagnosis was significantly associated with worse event-free and overall survival in the subgroup of 74 patients without FLT3-ITD, when considered either as a binary classification or as a continuous variable (p=0.02 for both event-free and overall survival). In multivariable analysis considering age, FLT3-ITD status, and CD47 expression as a continuous variable, increased CD47 expression remained associated with worse event-free survival with a hazard ratio of 1.33 (95% confidence interval 1.03 to 1.73, p=0.03) and overall survival with a hazard ratio of 1.31 (95% confidence interval 1.00 to 1.71, p=0.05) (Table 2).

TABLE 2

| Outcome Measure/Variables Considered | HR | 95% CI | P |
|---|---|---|---|
| Event-free survival | | | |
| CD47 expression, continuous, per 2-fold increase | 1.33 | 1.03-1.73 | 0.05 |
| FLT3-ITD positive vs. negative | 2.21 | 1.39-3.55 | <0.001 |
| Age, per year | 1.03 | 1.00-1.06 | 0.03 |
| Overall survival | | | |
| CD47 expression, continous, per 2-fold increase | 1.31 | 1.00-1.71 | 0.05 |
| FLT3-ITD, positive vs. negative | 2.29 | 1.42-3.58 | <0.001 |
| Age, per year | 1.03 | 1.01-1.06 | 0.01 |

Monoclonal Antibodies Directed Against Human CD47 Preferentially Enable Phagocytosis of AML LSC by Human Macrophages.

We hypothesized that increased CD47 expression on human AML contributes to pathogenesis by inhibiting phagocytosis of leukemia cells, leading us to predict that disruption of the CD47-SIRPα interaction with a monoclonal antibody directed against CD47 will preferentially enable the phagocytosis of AML LSC. Several anti-human CD47 monoclonal antibodies have been generated including some capable of blocking the CD47-SIRPα interaction (B6H12.2 and BRIC126) and others unable to do so (2D3) (Subramanian et al., 2006 Blood 107, 2548-2556). The ability of these antibodies to enable phagocytosis of AML LSC, or normal human bone marrow CD34+ cells, by human macrophages in vitro was tested. Incubation of AML LSC with human macrophages in the presence of IgG1 isotype control antibody or mouse anti-human CD45 IgG1 monoclonal antibody did not result in significant phagocytosis as determined by either immunofluorescence microscopy or flow cytometry. However, addition of the blocking anti-CD47 antibodies B6H12.2 and BRIC126, but not the non-blocking 2D3, enabled phagocytosis of AML LSC. No phagocytosis of normal CD34+ cells was observed with any of the antibodies.

Monoclonal Antibodies Directed Against Human CD47 Enable Phagocytosis of AML LSC by Mouse Macrophages.

In order to directly assess the effect of inhibiting the interaction of human CD47 with mouse SIRPα, the in vitro phagocytosis assays described above were conducted with mouse macrophages. Incubation of AML LSC with mouse macrophages in the presence of IgG1 isotype control antibody or mouse anti-human CD45 IgG1 monoclonal antibody did not result in significant phagocytosis as determined by either immunofluorescence microscopy or flow cytometry. However, addition of the blocking anti-CD47 antibodies B6H12.2 and BRIC126, but not the non-blocking 2D3, enabled phagocytosis of AML LSC.

A Monoclonal Antibody Directed Against Human CD47 Inhibits AML LSC Engraftment and Eliminates AML In Vivo.

The ability of the blocking anti-CD47 antibody B6H12.2 to target AML LSC in vivo was tested. First, a pre-coating strategy was utilized in which AML LSC were purified by FACS and incubated with IgG1 isotype control, anti-human CD45, or anti-human CD47 antibody. An aliquot of the cells was analyzed for coating by staining with a secondary antibody demonstrating that both anti-CD45 and anti-CD47 antibody bound the cells. The remaining cells were transplanted into newborn NOG mice that were analyzed for leukemic engraftment 13 weeks later. In all but one mouse, the isotype control and anti-CD45 antibody coated cells exhibited long-term leukemic engraftment. However, most mice transplanted with cells coated with anti-CD47 antibody had no detectable leukemia engraftment.

Figure 11A:
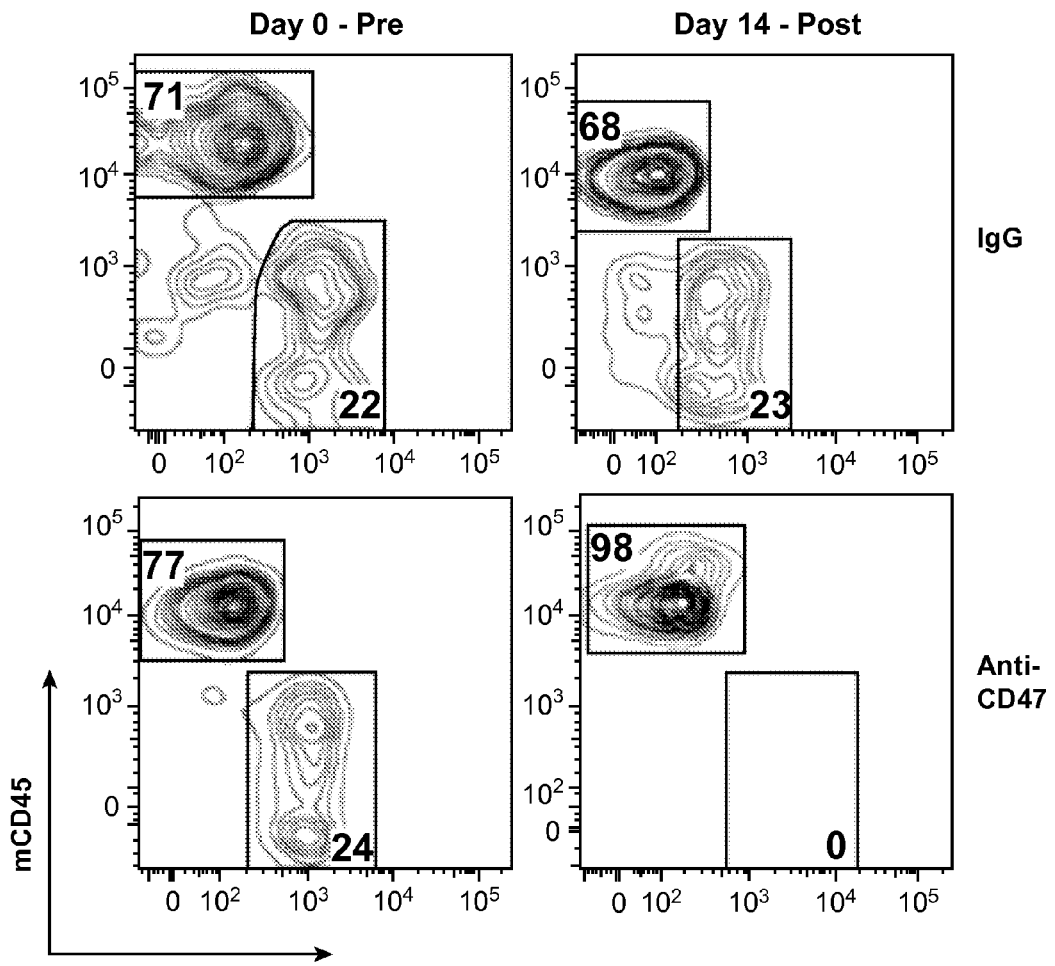
FIG. 11A-E: A Monoclonal Antibody Directed Against Human CD47 Eliminates AML In Vivo. Newborn NOG mice were transplanted with AML LSC, and 8-12 weeks later, peripheral blood (A,B) and bone marrow (C-E) were analyzed for baseline engraftment prior to treatment with anti-CD47 (B6H12.2) or control IgG antibody (Day 0). Mice were treated with daily 100 microgram intraperitoneal injections for 14 days, at the end of which, they were sacrificed and peripheral blood and bone marrow were analyzed for the percentage of human CD45+CD33+ leukemia. A. Pre- and post-treatment human leukemic chimerism in the peripheral blood from representative anti-CD47 antibody and control IgG-treated mice as determined by flow cytometry. B. Summary of human leukemic chimerism in the peripheral blood assessed on multiple days during the course of treatment demonstrated elimination of leukemia in anti-CD47 antibody treated mice compared to control IgG treatment (p=0.007). C. Pre- and post-treatment human leukemic chimerism in the bone marrow from representative anti-CD47 antibody or control IgG-treated mice as determined by flow cytometry. D. Summary of human leukemic chimerism in the bone marrow on day 14 relative to day 0 demonstrated a dramatic reduction in leukemic burden in anti-CD47 antibody treated mice compared to control IgG treatment (p<0.001). E. H&E sections of representative mouse bone marrow cavities from mice engrafted with SU004 post-treatment with either control IgG (panels 1,2) or anti-CD47 antibody (panels 4,5). IgG-treated marrows were packed with monomorphic leukemic blasts, while anti-CD47-treated marrows were hypocellular, demonstrating elimination of the human leukemia. In some anti-CD47 antibody-treated mice that contained residual leukemia, macrophages were detected containing phagocytosed pyknotic cells, capturing the elimination of human leukemia (panels 3,6 arrows).
Figure 11B:
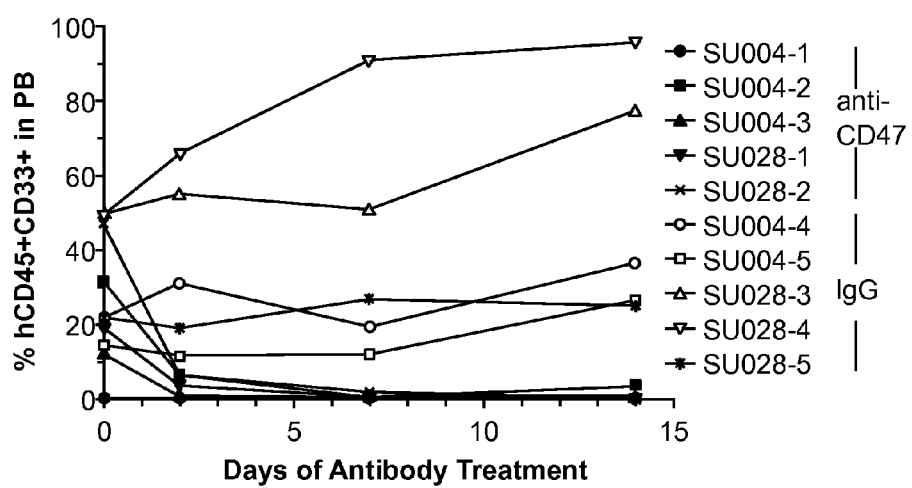
Figure 11C:
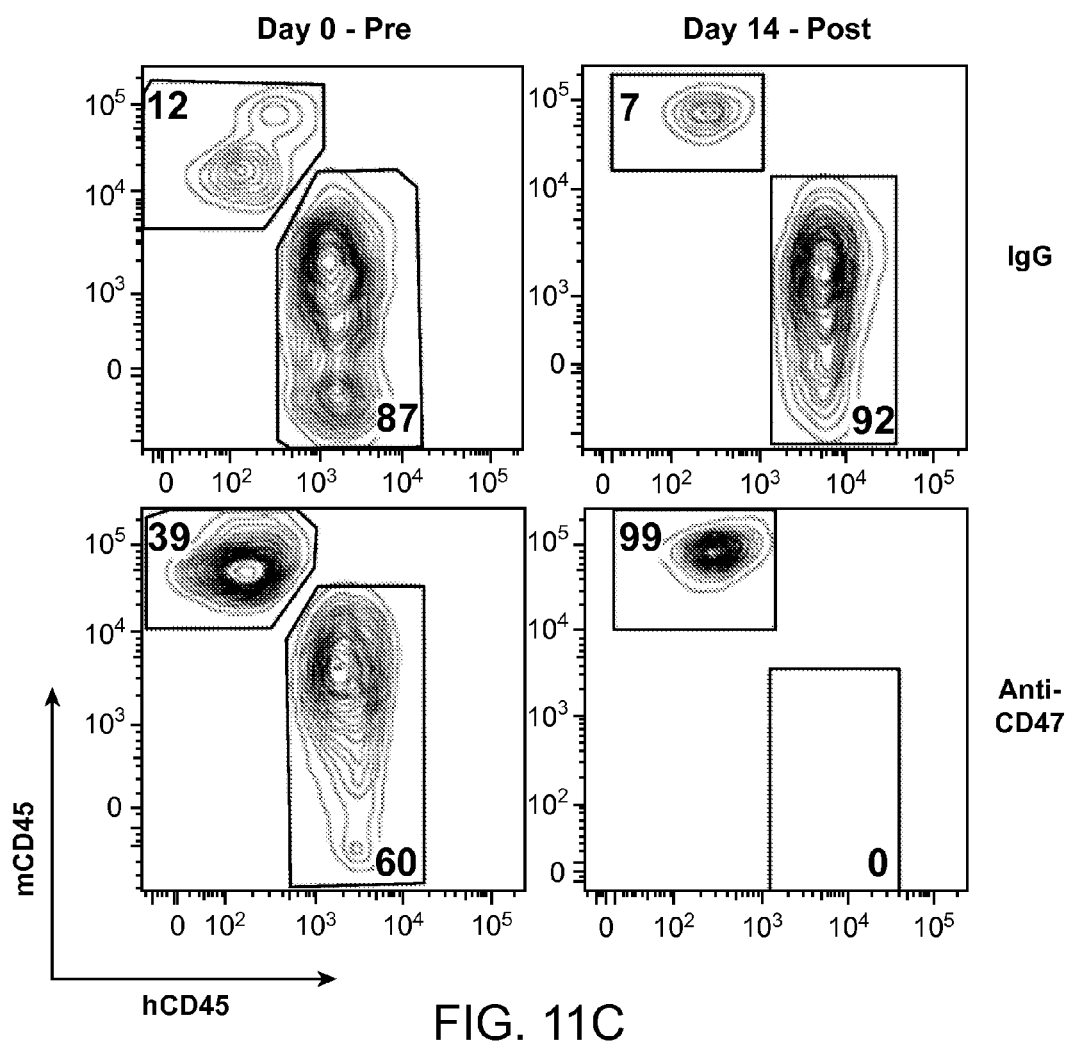
Figure 11D:
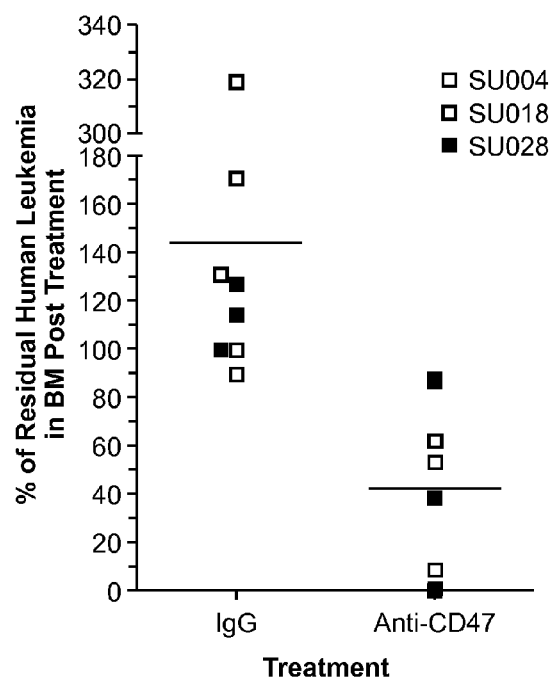
Figure 11E:
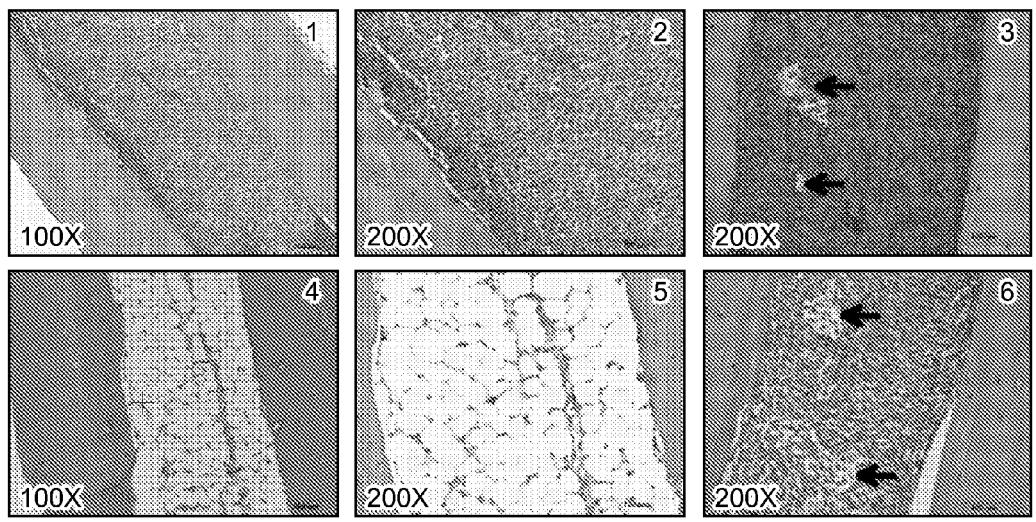

Next, a treatment strategy was utilized in which mice were first engrafted with human AML LSC and then administered daily intraperitoneal injections of 100 micrograms of either mouse IgG or anti-CD47 antibody for 14 days, with leukemic engraftment determined pre- and post-treatment. Analysis of the peripheral blood showed near complete elimination of circulating leukemia in mice treated with anti-CD47 antibody, often after a single dose, with no response in control mice (FIG. 11A,B). Similarly, there was a significant reduction in leukemic engraftment in the bone marrow of mice treated with anti-CD47 antibody, while leukemic involvement increased in control IgG-treated mice (FIG. 11C,D). Histologic analysis of the bone marrow identified monomorphic leukemic blasts in control IgG-treated mice (FIG. 11E, panels 1,2) and cleared hypocellular areas in anti-CD47 antibody-treated mice (FIG. 11E, panels 4,5). In the bone marrow of some anti-CD47 antibody-treated mice that contained residual leukemia, macrophages were detected containing phagocytosed pyknotic cells, capturing the elimination of human leukemia (FIG. 11E, panels 3,6).

We report here the identification of higher expression of CD47 on AML LSC compared to their normal counterparts and hypothesize that increased expression of CD47 on human AML contributes to pathogenesis by inhibiting phagocytosis of these cells through the interaction of CD47 with SIRPα. Consistent with this hypothesis, we demonstrate that increased expression of CD47 in human AML is associated with decreased overall survival. We also demonstrate that disruption of the CD47-SIRPα interaction with monoclonal antibodies directed against CD47 preferentially enables phagocytosis of AML LSC by macrophages in vitro, inhibits the engraftment of AML LSC, and eliminates AML in vivo. Together, these results establish the use of an anti-CD47 monoclonal antibody as a therapy for human leukemia.

As demonstrated here, CD47 contributes to pathogenesis via a distinct mechanism, conferring a survival advantage to LSC and progeny blasts through evasion of phagocytosis by the innate immune system. We believe that increased CD47 expression represents the first described immune evasion mechanism with prognostic and therapeutic implications for human AML.

Higher CD47 Expression is a Marker of Leukemia Stem Cells and Prognostic for Overall Survival in AML. AML LSC are enriched in the Lin-CD34+CD38- fraction, which in normal bone marrow contains HSC and MPP. The identification of cell surface molecules that can distinguish between leukemic and normal stem cells is essential for flow cytometry-based assessment of minimal residual disease (MRD) and for the development of prospective separation strategies for use in cellular therapies. Several candidate molecules have recently been identified, including CD123, CD96, CLL-1, and now CD47.

Increased CD47 expression is independently predictive of a worse clinical outcome in AML patients with a normal karyotype, including the subset without the FLT3-ITD mutation, which is the largest subgroup of AML patients. As this analysis was dependent on the relative expression of CD47 mRNA, a quantitative PCR assay for AML prognosis may be based on the level of CD47 expression. Such an assay could be utilized in risk adapted therapeutic decision making, particularly in the large subgroup of AML patients with normal karyotypes who lack the FLT3-ITD mutation.

Targeting of CD47 on AML LSC with Therapeutic Monoclonal Antibodies.

Cell surface molecules preferentially expressed on LSC compared to their normal counterparts are suitable for targeting with therapeutic monoclonal antibodies. Thus far, several molecules have been targeted on AML including CD33, CD44, CD123, and now CD47. CD33 is the target of the monoclonal antibody conjugate gemtuzumab ozogamicin (Mylotarg), which is approved for the treatment of relapsed AML in older patients. Targeting of CD44 with a monoclonal antibody was shown to markedly reduce AML engraftment in mice, with evidence that it acts specifically on LSC to induce differentiation. A monoclonal antibody directed against CD123 was recently reported to have efficacy in reducing AML LSC function in vivo. Here we report that a monoclonal antibody directed against CD47 is able to stimulate phagocytosis of AML LSC in vitro and inhibit engraftment in vivo. A combination of CD47 with CD33; with CD44 or with CD123 may provide for synergistic results.

Several lines of evidence suggest that targeting of CD47 with a monoclonal antibody likely acts by disrupting the CD47-SIRPα interaction, thereby preventing a phagocytic inhibitory signal. First, two blocking anti-CD47 antibodies enabled AML LSC phagocytosis. Second, the isotype-matched anti-CD45 antibody, which also binds LSC, failed to produce the same effects.

For human clinical therapies, blocking CD47 on AML LSC with humanized monoclonal antibodies promotes LSC phagocytosis through a similar mechanism, as indicated by the human macrophage-mediated in vitro phagocytosis (FIG. 8A,C). We identified a preferential effect of anti-CD47 antibodies in enabling the phagocytosis of AML LSC compared to normal bone marrow CD34+ cells by human macrophages in vitro. In fact, no increased phagocytosis of normal CD34+ cells compared to isotype control was detected, demonstrating that blocking CD47 with monoclonal antibodies is a viable therapeutic strategy for human leukemia.

The experimental evidence presented here provides for anti-CD47 monoclonal antibodies as monotherapy or a combination strategy for treatment of leukemia. The combination of an anti-CD47 antibody, able to block a strong inhibitory signal for phagocytosis, with a second antibody able to bind a LSC-specific molecule (for example CD96, CD33, CD123, etc.) and engage Fc receptors on phagocytes, thereby delivering a strong positive signal for phagocytosis, may result in a synergistic stimulus for phagocytosis and specific elimination of LSC. Furthermore, combinations of monoclonal antibodies to LSC that include blocking anti-CD47 and human IgG1 antibodies directed against two other cell surface antigens will be more likely to eliminate leukemia cells with pre-existing epitope variants or antigen loss that are likely to recur in patients treated with a single antibody.

Experimental Procedures

Human Samples.

Normal human bone marrow mononuclear cells were purchased from AllCells Inc. (Emeryville, Calif.). Human acute myeloid leukemia samples (FIG. 1A) were obtained from patients at the Stanford University Medical Center with informed consent, according to an IRB-approved protocol (Stanford IRB #76935 and 6453). Human CD34− positive cells were enriched with magnetic beads (Miltenyi Biotech).

Flow Cytometry Analysis and Cell Sorting.

A panel of antibodies was used for analysis and sorting of AML LSC (Lin−CD34+CD38−CD90−, where lineage included CD3, CD19, and CD20), HSC (Lin−CD34+CD38−CD90+), and MPP (Lin−CD34+CD38−CD90−CD45RA−) as previously described (Majeti et al., 2007). Analysis of CD47 expression was performed with an anti-human CD47 PE antibody (clone B6H12, BD Biosciences, San Jose Calif.).

Genomic DNA Preparation and Analysis of FLT3-ITD by PCR.

Genomic DNA was isolated from cell pellets using the Gentra Puregene Kit according to the manufacturer's protocol (Gentra Systems, Minneapolis, Minn.). FLT3-ITD status was screened by PCR using primers that generated a wild-type product of 329 bp and ITD products of variable larger sizes.

Anti-Human CD47 Antibodies.

Monoclonal mouse anti-human CD47 antibodies included: BRIC126, IgG2b (Abcam, Cambridge, Mass.), 2D3, IgG1 (Ebiosciences, San Diego, Calif.), and B6H12.2, IgG1. The B6H12.2 hybridoma was obtained from the American Type Culture Collection (Rockville, Md.). Antibody was either purified from hybridoma supernatant using protein G affinity chromatography according to standard procedures or obtained from BioXCell (Lebanon, N.H.).

Methylcellulose Colony Assay.

Methylcellulose colony formation was assayed by plating sorted cells into a 6-well plate, each well containing 1 ml of complete methylcellulose (Methocult GF+ H4435, Stem Cell Technologies). Plates were incubated for 14 days at 37° C., then scored based on morphology.

In Vitro Phagocytosis Assays.

Human AML LSC or normal bone marrow CD34+ cells were CFSE-labeled and incubated with either mouse or human macrophages in the presence of 7 μg/ml IgG1 isotype control, anti-CD45 IgG1, or anti-CD47 (clones B6H12.2, BRIC126, or 2D3) antibody for 2 hours. Cells were then analyzed by fluorescence microscopy to determine the phagocytic index (number of cells ingested per 100 macrophages). In some cases, cells were then harvested and stained with either a mouse or human macrophage marker and phagocytosed cells were identified by flow cytometry as macrophage+CFSE+. Statistical analysis using Student's t-test was performed with GraphPad Prism (San Diego, Calif.).

In Vivo Pre-Coating Engraftment Assay.

LSC isolated from AML specimens were incubated with 28 μg/mL of IgG1 isotype control, anti-CD45 IgG1, or anti-CD47 IgG1 (B6H12.2) antibody at 4° C. for 30 minutes. A small aliquot of cells was then stained with donkey anti-mouse PE secondary antibody (Ebioscience) and analyzed by flow cytometry to assess coating. Approximately $10^5$ coated LSC were then transplanted into each irradiated newborn NOD.Cg-PrkdcscidIl2rgtm1Wjl/SzJ (NOG) mouse. Mice were sacrificed 13 weeks post-transplantation and bone marrow was analyzed for human leukemia engraftment (hCD45+ hCD33+) by flow cytometry (Majeti et al., 2007 Cell Stem Cell 1, 635-645). The presence of human leukemia was confirmed by Wright-Giemsa staining of hCD45+ cells and FLT3-ITD PCR. Statistical analysis using Student's t-test was performed with GraphPad Prism (San Diego, Calif.).

In Vivo Antibody Treatment of AML Engrafted Mice.

$1-25\times10^5$ FACS-purified LSC were transplanted into NOG pups. Eight to twelve weeks later, human AML engraftment (hCD45+CD33+ cells) was assessed in the peripheral blood and bone marrow by tail bleed and aspiration of the femur, respectively. Engrafted mice were then treated with daily intraperitoneal injections of 100 micrograms of anti-CD47 antibody or IgG control for 14 days. On day 15 mice were sacrificed and the peripheral blood and bone marrow were analyzed for AML.

AML Patients, Microarray Gene Expression Data, and Statistical Analysis. Gene expression and clinical data were analyzed for three previously described cohorts of adult AML patients: (1) a training dataset of 285 patients with diverse cytogenetic and molecular abnormalities described by Valk et al., (2) a test dataset of 242 patients with normal karyotypes described by Metzeler et al., and (3) a validation dataset of 137 patients with normal karyotypes described by Bullinger et al. The clinical end points analyzed included overall and event-free survival, with events defined as the interval between study enrollment and removal from the study owing to a lack of complete remission, relapse, or death from any cause, with data censored for patients who did not have an event at the last follow-up visit.

FLT3-ITD PCR.

All reactions were performed in a volume of 50 μl containing 5 μl of 10× PCR buffer (50 mM KCL/10 nM Tris/2 mM MgCl2/0.01% gelatin), 1 of 10 mM dNTPs, 2 units of Taq polymerase (invitrogen), 1 ul of 10 μM forward primer 11F (SEQ ID NO:8) (5'-GCAATTTAGGTATGAAAGCCAGC-3') and reverse primer 12R (SEQ ID NO:9) (5'-CTTTCAG-CATTTTGACGGCAACC-3'), and 10-50 ng of genomic DNA. PCR conditions for amplification of the FLT3 gene were 40 cycles of denaturation (30 sec at 95° C.) annealing (30 sec at 62° C.), and extension (30 sec at 72° C.).

Preparation of Mouse and Human Macrophages.

BALB/c mouse bone marrow mononuclear cells were harvested and grown in IMDM containing 10% FBS supplemented with 10 ng/mL recombinant murine macrophage colony stimulating factor (M-CSF, Peprotech, Rocky Hill, N.J.) for 7-10 days to allow terminal differentiation of monocytes to macrophages. Human peripheral blood mononuclear cells were prepared from discarded normal blood from the Stanford University Medical Center. Monocytes were isolated by adhering mononuclear cells to culture plates for one hour at 37° C., after which non-adherent cells were removed by washing. The remaining cells were >95% CD14 and CD11b positive. Adherent cells were then incubated in IMDM plus 10% human serum (Valley Biomedical, Winchester, Va.) for 7-10 days to allow terminal differentiation of monocytes to macrophages.

In Vitro Phagocytosis Assay.

BMDM or peripheral blood macrophages were harvested by incubation in trypsin/EDTA (Gibco/Invitrogen) for 5 minutes followed by gentle scraping. $5 \times 10^4$ macrophages were plated in each well of a 24-well tissue culture plate in 10% IMDM containing 10% FBS. After 24 hours, media was replaced with serum-free IMDM and cells were cultured an additional 2 hours. LSC were fluorescently labeled with CFSE according to the manufacturer's protocol (Invitrogen). $2 \times 10^4$ CFSE-labeled LSC were added to the macrophage-containing wells along with 7 µg/mL of IgG1 isotype (Ebiosciences), anti-CD45 (clone H130, Ebiosciences), or anti-CD47 antibody, and incubated for 2 hours. Wells were then washed 3 times with IMDM and examined under an Eclipse T5100 immunofluorescent microscope (Nikon) using an enhanced green fluorescent protein filter able to detected CFSE fluorescence. The number of CFSE positive cells within macrophages was counted and the phagocytic index was determined as the number of ingested cells per 100 macrophages. At least 200 macrophages were counted per well. Flourescent and brightfield images were taken separately and merged with Image Pro Plus (Media Cybernetics, Bethesda, Md.). For flow cytometry analysis of phagocytosis, the cells were then harvested from each well using trypsin/EDTA. Cell suspensions were then stained with a mouse macrophage antibody anti-mouse F4/80-PECy7 (Ebiosciences) or anti-human CD14-PECy7 (Ebiosciences) and analyzed on a FACSAria. Phagocytosed LSC were defined as either CFSE+F4/80+ or CFSE+CD14+ cells when incubated with murine or human macrophages, respectively.

Microarray Gene Expression Data.

Training Set: Gene expression data, cytogenetics data, and molecular data for the 285 and 465 patients with AML profiled with Affymetrix HG-U133A and HG-U133 Plus 2.0 microarrays by Valk et al. and Jongen-Lavrencic et al. respectively, were obtained from the Gene Expression Omnibus using the corresponding accession numbers (GSE1159 and GSE6891). Outcome data were only available for the former dataset, and the corresponding clinical information were kindly provided by the authors. This cohort is presented as the "training" dataset. The latter dataset was used to confirm univariate associations with karyotype and molecular mutations described in the former. However, these two datasets overlapped in that 247 of the 285 patients in the first study were included in the second, and were accordingly excluded in validation of the association of FLT3-ITD with CD47 expression in the 2nd dataset. Using NetAffx4, RefSeq5, and the UCSC Genome Browser6, we identified 211075_s_at and 213857_s_at as Affymetrix probe sets on the U133 Plus 2.0 microarray mapping exclusively to constitutively transcribed exons of CD47. The geometric mean of the base-2 logarithms of these two probe sets was employed in estimating the mRNA expression level for CD47, and corresponding statistical measures for associations with FAB classification, karyotype, and molecular mutations. Because the data provided by Valk et al. as GSE1159 were Affymetrix intensity measurements, we converted these intensities to normalized base-2 logarithms of ratios to allow comparison to the corresponding measurements from cDNA microarrays using a conventional scheme. Specifically, we first (1) normalized raw data using CEL files from all 291 microarrays within this dataset using gcRMA8, then (2) generated ratios by dividing the intensity measurement for each gene on a given array by the average intensity of the gene across all arrays, (3) log-transformed (base 2) the resulting ratios, and (4) median centered the expression data across arrays then across genes. For the assessment of the prognostic value of CD47, we employed the probe set 213857_s_at from the Affymetrix HG-U133A and HG-U133 Plus 2.0 microarrays, given its similar expression distribution (Supplemental FIG. 3B), and considering its position within the mRNA transcript as compared with cDNA clones on the Stanford cDNA microarrays as annotated within the NetAffx resource.

Test Set:

Gene expression and clinical data for the 242 adult patients with NKAML profiled with Affymetrix HG-U133A and HG-U133 Plus 2.0 microarrays by Metzeler et al. were obtained from the Gene Expression Omnibus using the corresponding accession numbers (GSE12417). Since raw data were not available for this dataset, for purposes of assessing the prognostic value of CD47, we employed the normalized datasets provided by the authors (base 2 logarithms) and assessed expression of CD47 using the probe set 213857_s_at on the corresponding microarrays.

Validation Set:

Gene expression data for the 137 patients with normal karyotype AML profiled with cDNA microarrays by Bullinger et al. were obtained from the Stanford Microarray Database10. The corresponding clinical information including outcome data and FLT3 mutation status were kindly provided by the authors. Using the original annotations of microarray features as well as SOURCE11, RefSeq5, and the UCSC Genome Browser6, we identified IMAGE:811819 as a sequence verified cDNA clone mapping to the constitutively transcribed 3' terminal exon of CD47 on the corresponding cDNA microarrays.

Details of Treatment:

AML patients described by Valk et al. (training set), were treated according to several protocols of the Dutch-Belgian Hematology-Oncology Cooperative group. The majority (90%) of the NK-AML patients described by Metzeler et al. (test set) were treated per protocol AMLCG-1999 of the German AML Cooperative Group, with all patients receiving intensive double-induction and consolidation chemotherapy. All 137 NK-AML patients described by Bullinger et al. (validation set) received standard-of-care intensified treatment regimens (protocol AML HD98A), which included 2 courses of induction therapy with idarubicin, cytarabine, and etoposide, one consolidation cycle of high-dose cytarabine and mitoxantrone (HAM), followed by random assignment to a late consolidation cycle of HAM versus autologous hematopoietic cell transplantation in case no HLA identical family donor was available for allogeneic hematopoietic cell transplantation.

Statistical Analysis.

We used two tailed t-tests and analysis of variance for the estimation of significant differences in CD47 expression level across subgroups of AML based on morphologic, cytogenetic, and molecular categorizations. Associations between the high and low CD47 groups and baseline clinical, demographic, and molecular features were analyzed using Fisher's exact and Mann-Whitney rank sum tests for categorical and continuous variables, respectively. Two-sided p-values of less than 0.05 were considered to indicate statistical significance.

The prognostic value of CD47 expression was measured through comparison of the event-free and overall survival of patients with estimation of survival curves by the Kaplan-Meier product limit method and the log-rank test. Within this analysis, we first derived a binary classification of AML patients into High CD47 and Low CD47 expression groups by comparing the expression of CD47 (as measured by 213857_s_at within GSE1159) relative to an optimal threshold. This threshold was determined using X-Tile16, a method which we employed to maximize the chi-square statistic between the two groups for the expected versus observed number of deaths. This stratification segregates the 261 AML patients with available outcome data into two unequally sized groups, with 72% of patients with lowest expression considered CD47 low, and 28% with highest expression considered CD47 high. These two groups have different overall survival with a hazard ratio of 1.42 for the CD47 high group, and a corresponding uncorrected p-value of 0.033, which requires cross-validation to avoid the risk of overfitting.

Accordingly, we assessed the validity and robustness of risk stratification using CD47 expression by applying this optimal threshold to an independent test cohort of 242 NK-AML patients described by Metzeler et al. Notably, despite the presence of other variables potentially confounding associations with survival (including more advanced age, and differing therapies), derivation of an optimal cutpoint using the 242 NK-AML patients within the test dataset yielded a similar stratification, with 74% of patients with lowest expression considered CD47 low, and 26% with highest expression considered CD47 high.

Next, we assessed the validity of this stratification in a cross-validation cohort of 137 uniformly treated NK-AML patients described by Bullinger et al. Within this validation dataset, we could similarly define two groups of similar size (i.e., 72% and 28% with lowest and highest CD47 levels, respectively), and these two groups had significantly different outcomes when assessed for overall survival (FIG. 22B, p=0.002, hazard ratio 2.02, 95% CI 1.37 to 4.03), and event-free survival (FIG. 223A, p=0.004, hazard ratio 1.94, 95% CI 1.30 to 3.77). Of the 137 patients, 5 did not have reliable measurements for CD47 when using the data selection and normalization criteria described by the authors.

To determine the robustness of this association, we also examined the predictive value of CD47 expression when the validation cohort was divided into low and high CD47 expression groups based on expression relative to the median, or as a continuous variable. As above, higher CD47 expression was associated with worse event-free and overall survival. Of the 137 patients studied, a subset of 123 patients had available survival data, CD47 expression data, and FLT3-ITD status reported. Within this cohort, we assessed the relationship of CD47 expression level as a continuous variable with outcome using univariate Cox proportional-hazards analysis, with event-free survival or overall survival as the dependent variable. We used multivariate Cox-proportional hazards analysis with event-free survival or overall survival as the dependent variable and FLT3-ITD status, age, and continuous expression level of CD47 as directly assessed independent variables.

Associations of CD47 with other covariates (eg, NPM1, CEBPA) were limited by sample size and missing data for covariates. The Wald test was used to assess the significance of each covariate in multivariate analyses. Univariate and multivariate proportional-hazards analyses were done using the coxph function in the R statistical package.

Example 4

CD47 Expression is Increased on NHL Cells Compared to Normal B Cells

Figure 12A:
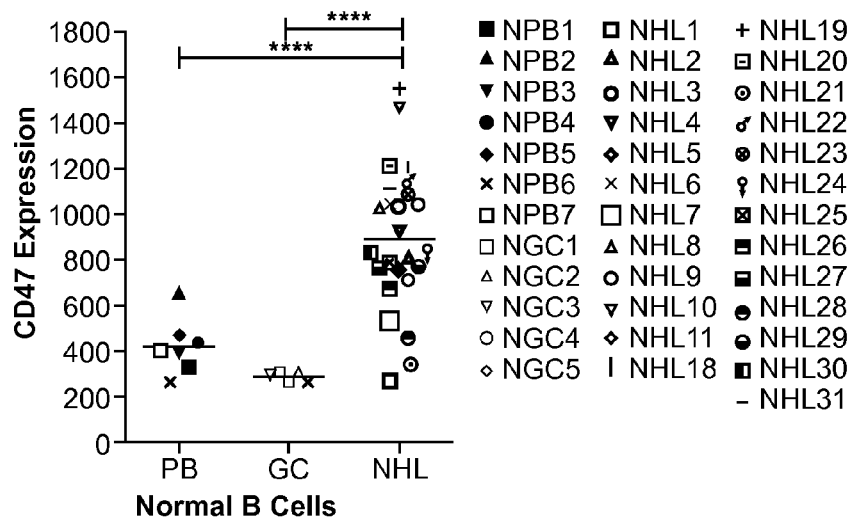
Figure 12B:
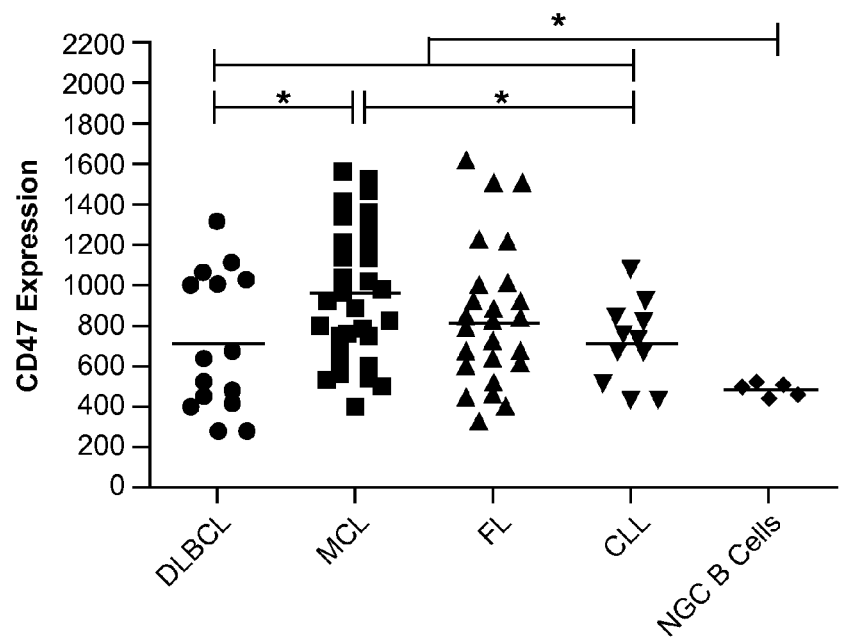

We examined CD47 protein expression on primary human NHL samples and normal B cells by flow cytometry. Compared to both normal peripheral blood and germinal center B cells, CD47 was more highly expressed on a large subset of primary patient samples from multiple B cell NHL subtypes (FIG. 12A), including diffuse large B cell lymphoma (DLBCL), B cell chronic lymphocytic leukemia (B-CLL), mantle cell lymphoma (MCL), follicular lymphoma (FL), marginal zone lymphoma (MZL), and pre-B acute lymphoblastic leukemia (pre-B ALL). Across NHL subtypes, we found differing levels of CD47 expression that also varied within each NHL subtype (FIG. 12B).

Increased CD47 Expression Correlates with a Worse Clinical Prognosis and Adverse Molecular Features in Multiple NHL Subtypes.

Figure 12C:
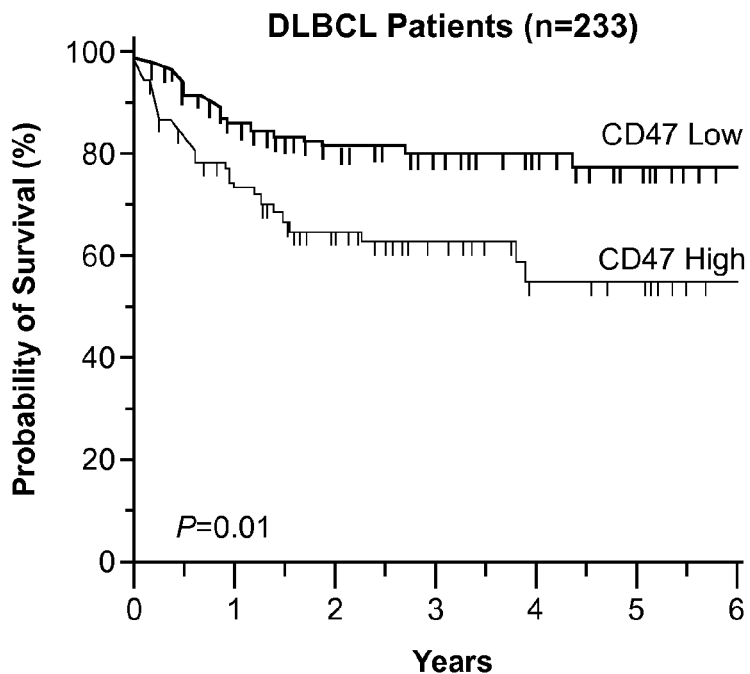
Figure 12D:
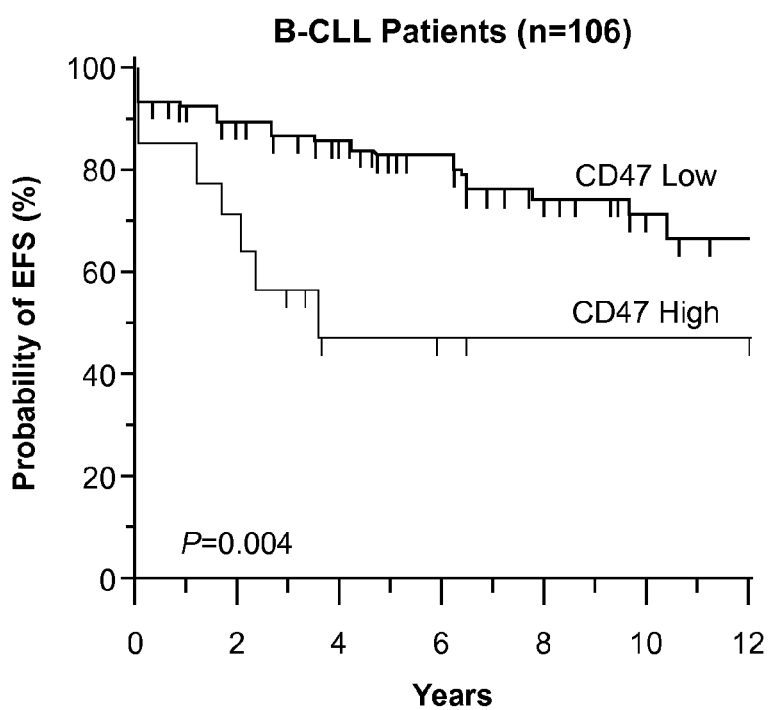
Figure 12E:
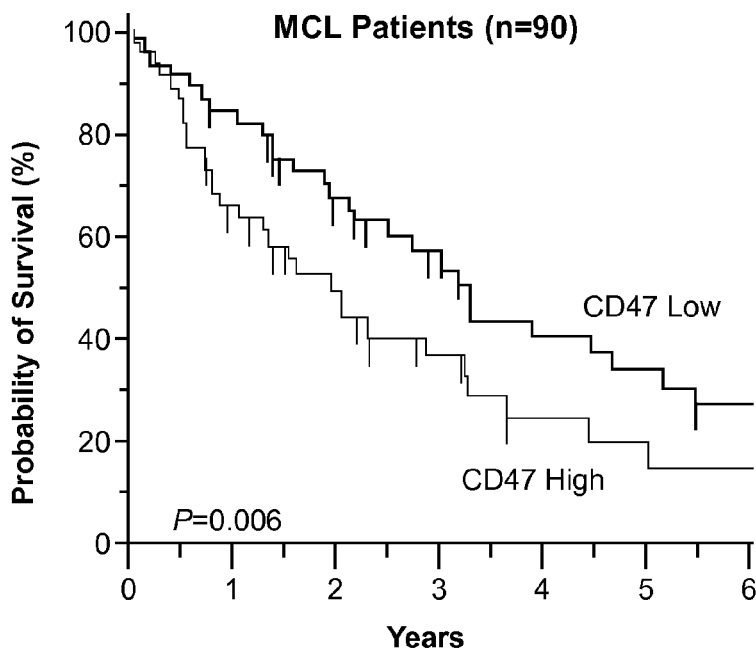

Having previously shown a correlation between CD47 mRNA and protein expression, we assessed CD47 mRNA expression across NHL subtypes for associations with morphologic and molecular subgroups using gene expression data from previously described patient cohorts and investigated the prognostic implications of increased CD47 expression in disease outcome. Higher CD47 expression was associated with adverse prognosis in DLBCL, B-CLL, and MCL (FIGS. 12C-12E). In patients with DLBCL, whether treated with or without rituximab-based combination chemotherapy (FIG. 12C), higher CD47 expression was significantly associated with risk of death. This increased risk was largely due to disease progression, a finding validated in an independent cohort of patients using quantitative RT-PCR on fixed archival specimens.

Figure 12F:
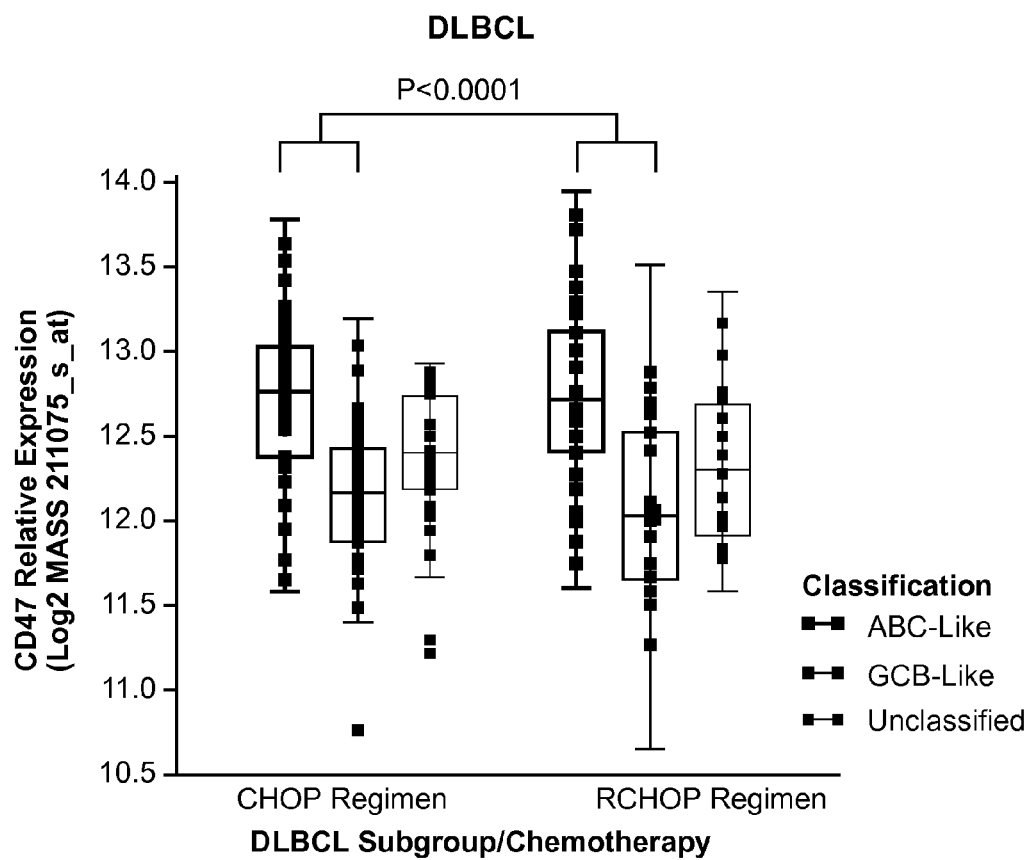
Figure 12G:
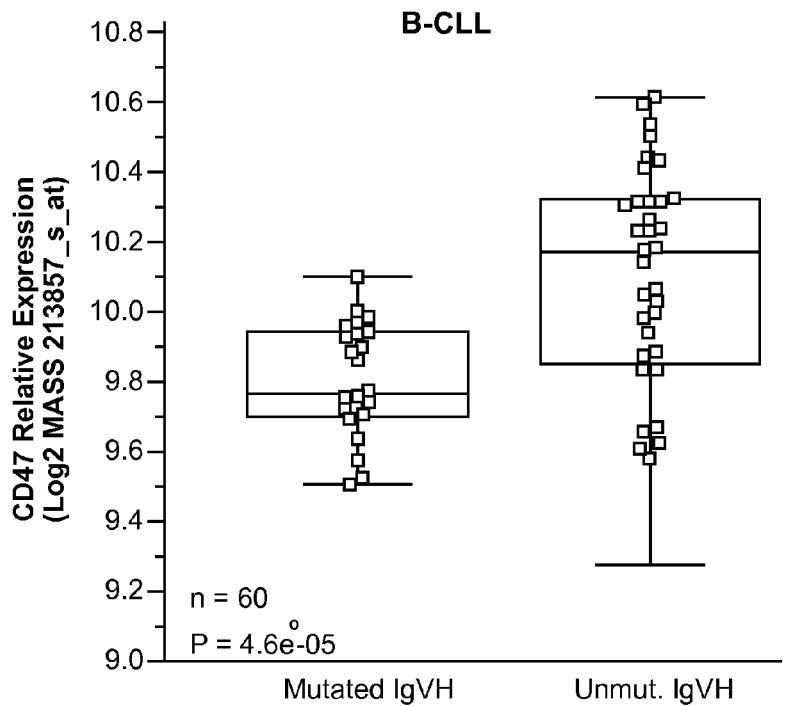
Figure 12H:
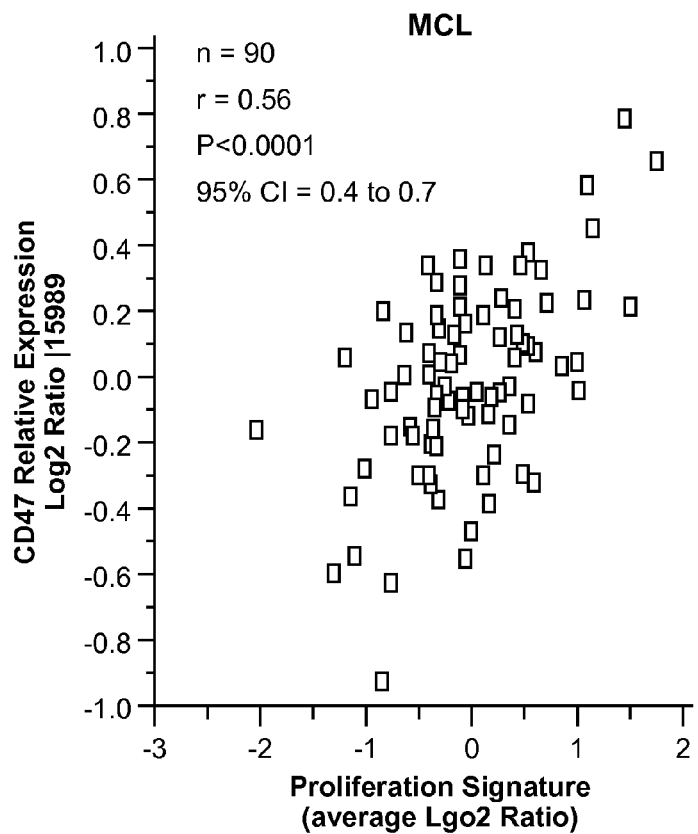

We next investigated whether increased CD47 expression was associated with known adverse molecular features in NHL. In DLBCL, prior studies have identified two distinct subgroups based on the presumed cell of origin of tumors: normal germinal center B cells (GCB-like), which are associated with a favorable clinical outcome, or activated blood memory B cells (ABC-like), which are associated with a poor clinical outcome. CD47 expression was significantly higher in ABC-like DLBCL (FIG. 12F). CD47 expression was not found to have independent prognostic value within GCB and ABC subtypes, suggesting a strong association with the cell-of-origin classification of DLBCL. Higher CD47 expression was also associated with unmutated immunoglobulin heavy chain variable regions (IgVH) in CLL (FIG. 12G) and significantly correlated with the proliferative index in MCL (FIG. 12H), both known adverse prognostic factors. In multivariate analyses, CD47 expression remained prognostic of disease progression independent from the international prognostic index in DLBCL and two major prognostic factors in CLL: IgVH mutation status and ZAP-70 status. Within the small MCL cohort, a multivariate model did not find independent prognostic value for CD47 when considering the proliferation index.

Blocking Anti-CD47 Antibodies Enable Phagocytosis of NHL Cells by Macrophages and Synergize with Rituximab In Vitro.

Figure 13A:
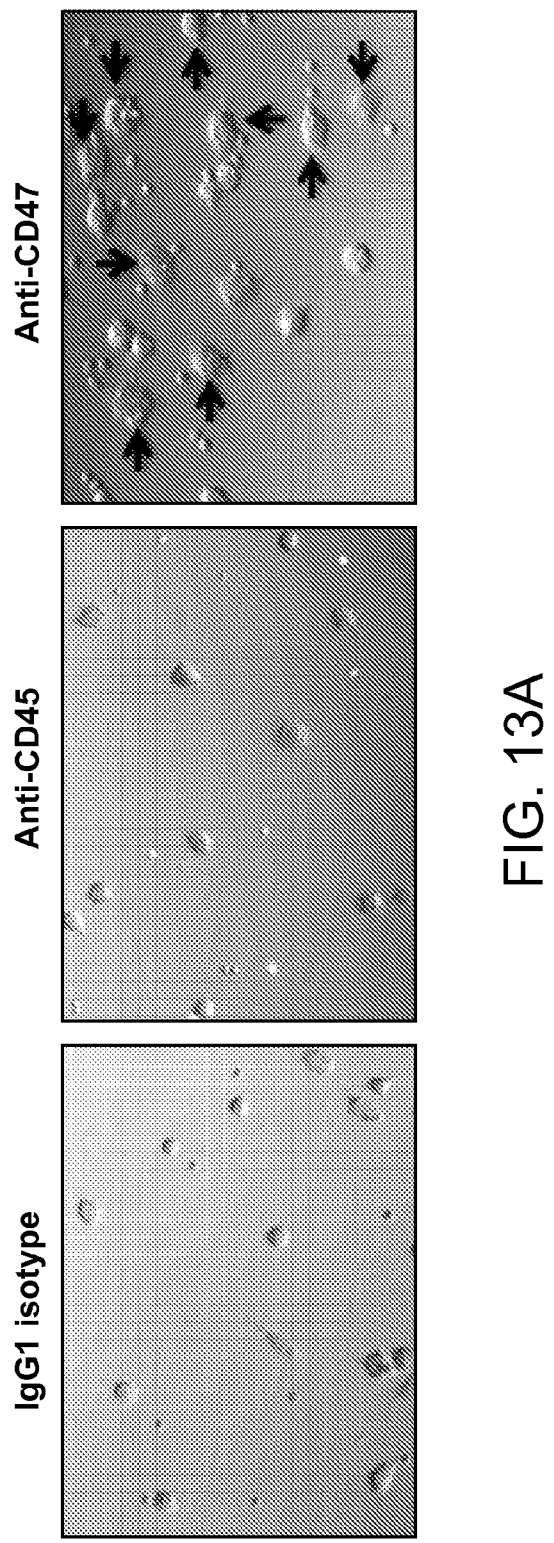
FIG. 13. Blocking Antibodies against CD47 Enable Phagocytosis of NHL Cells by Macrophages and Synergize with Rituximab In Vitro (A) CFSE-labeled NHL cells were incubated with human macrophages and the indicated antibodies and examined by immunofluorescence microscopy to detect phagocytosis (arrows). Photomicrographs from a representative NHL sample are shown. (B) Phagocytic indices of primary human NHL cells (blue), normal peripheral blood (NPB) cells (red), and NHL cell lines (purple, orange, and green) were determined using human (left) and mouse (middle) macrophages. Antibody-induced apoptosis (right panel) was tested by incubating NHL cells with the indicated antibodies or staurosporine without macrophages and assessing the percentage of apoptotic and dead cells (% annexin V and/or PI positive). (C) Synergistic phagocytosis by anti-CD47 antibody (B6H12.2) and anti-CD20 mAbs was examined by isobologram analysis and determination of combination indices (CI). CI$_{obs}$ indicates observed results, and the dashed line indicates the expected results if antibodies were additive. (D and E) Synergy between anti-CD47 antibody and rituximab in the phagocytosis of NHL and NPB cells was assessed by determining the phagocytic index when incubated with a combination of both antibodies compared to either antibody alone at twice the dose, with either mouse (D) or human (E) macrophages. NHL17*: cell line derived from primary sample NHL17. *p<0.001, p<0.0001, ***p<0.00001.
Figure 13B:
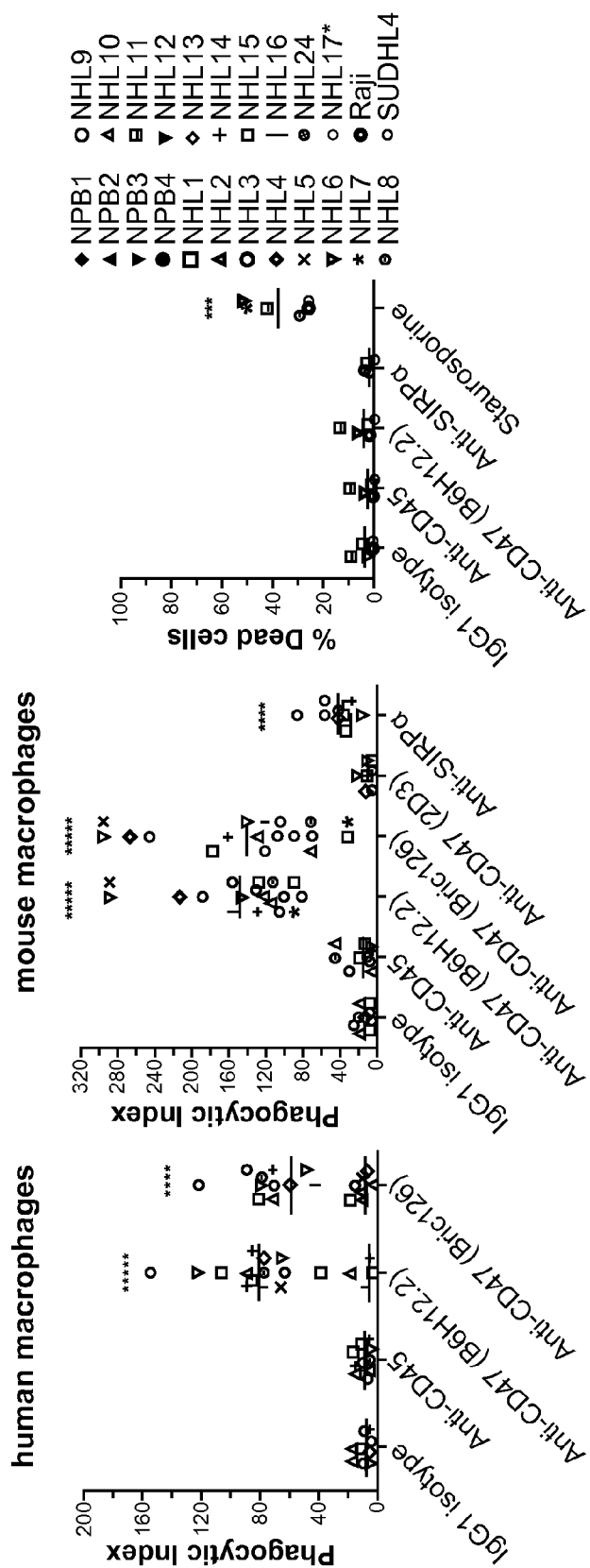

We first tested the ability of anti-human CD47 antibodies to enable phagocytosis of human NHL cell lines, primary NHL cells, and normal peripheral blood (NPB) cells by human macrophages in vitro. Incubation of NHL cells in the presence of IgG1 isotype control or anti-CD45 IgG1 antibody did not result in significant phagocytosis; however, two different blocking anti-CD47 antibodies (B6H12.2 and BRIC126) enabled phagocytosis of NHL cells but not NPB cells (FIGS. 13A and 13B).

Next, we repeated the in vitro phagocytosis assays with mouse macrophages. Incubation of NHL cells in the presence of IgG1 isotype control or anti-CD45 IgG1 antibody did not result in significant phagocytosis; however, phagocytosis of NHL cells was observed with blocking antibodies to CD47 (B6H12.2 and BRIC126), whereas no phagocytosis was observed with a nonblocking antibody (2D3) (FIG. 13B). Disruption of the CD47-SIRPα interaction with an anti-mouse SIRPα antibody also resulted in significant phagocytosis (FIG. 13B).

Given variable expression of CD47 on primary NHL, we investigated by two independent methods whether CD47 expression levels correlated with the degree of anti-CD47 antibody-mediated phagocytosis. First, lentiviral shRNA vectors were used to knock down expression of CD47 in Raji cells. Several clones were generated with a range of CD47 knockdown. Those clones with a greater than 50% reduction in CD47 expression (shCD47-1 and shCD47-2) demonstrated a significant reduction in anti-CD47 antibody-mediated phagocytosis. In the second approach, a statistical analysis demonstrated a positive correlation between CD47 expression and degree of anti-CD47 antibody-mediated phagocytosis with both mouse and human macrophage effector cells.

It has been reported that immobilized or crosslinked antibodies against CD47 induce apoptosis of primary human B-CLL cells, as well as several malignant lymphoid cell lines. Therefore, anti-CD47 antibodies might be predicted to directly induce apoptosis of NHL cells that are then recognized by macrophages and phagocytosed. Contrary to this prediction, when NHL cells were incubated with anti-CD47 antibody in the absence of macrophages, no induction of apoptosis was observed when cells were incubated in suspension for either 2 hr (FIG. 13B, right) or 8 hr. Incubation of NHL cells with immobilized anti-CD47 antibody resulted in increased apoptosis compared to controls, consistent with prior reports. Given that phagocytosis of NHL cells occurs in the presence of soluble anti-CD47 mAbs, it is unlikely that these mAbs induce apoptosis of NHL cells that are then secondarily phagocytosed.

Figure 13C:
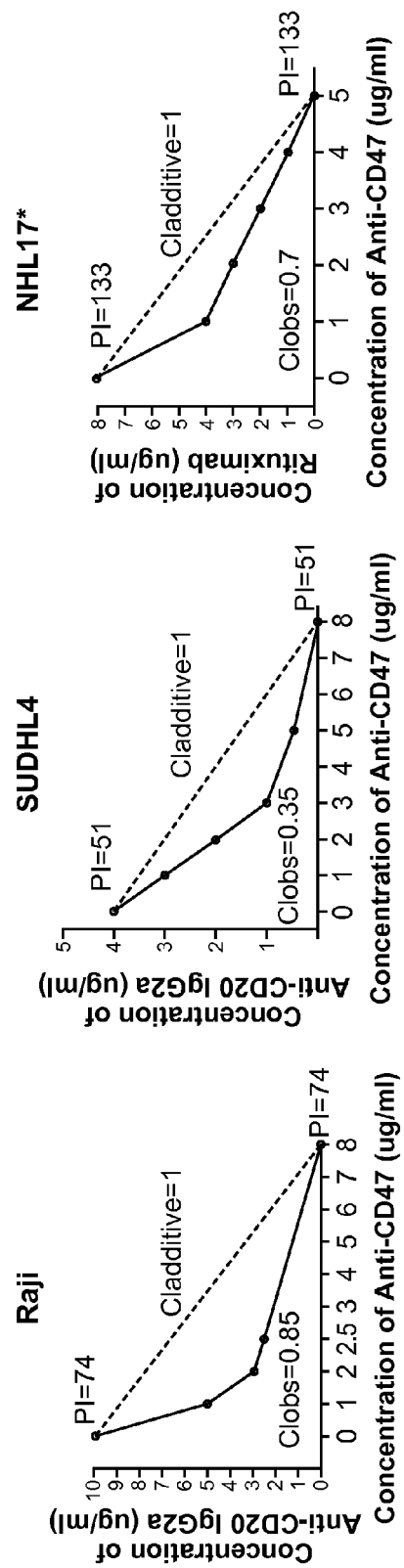
Figure 13E:
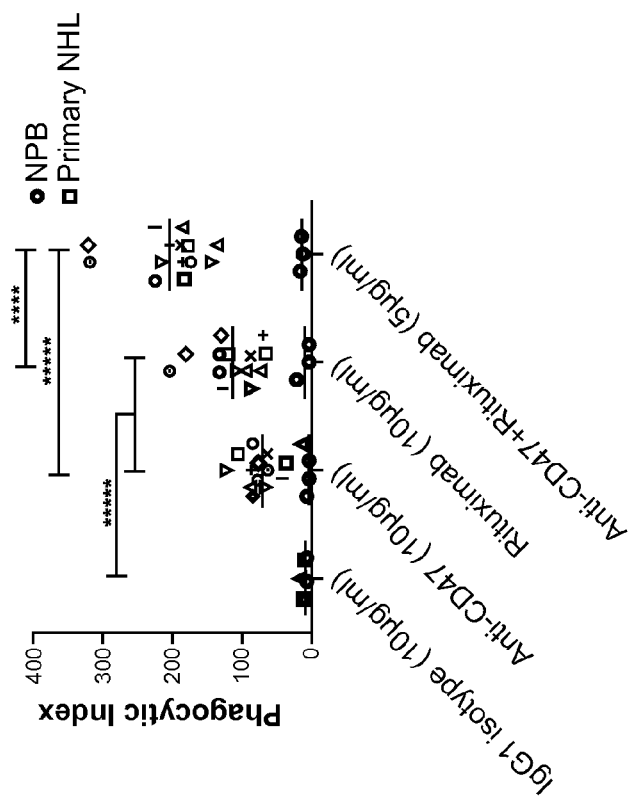
Figure 13D:
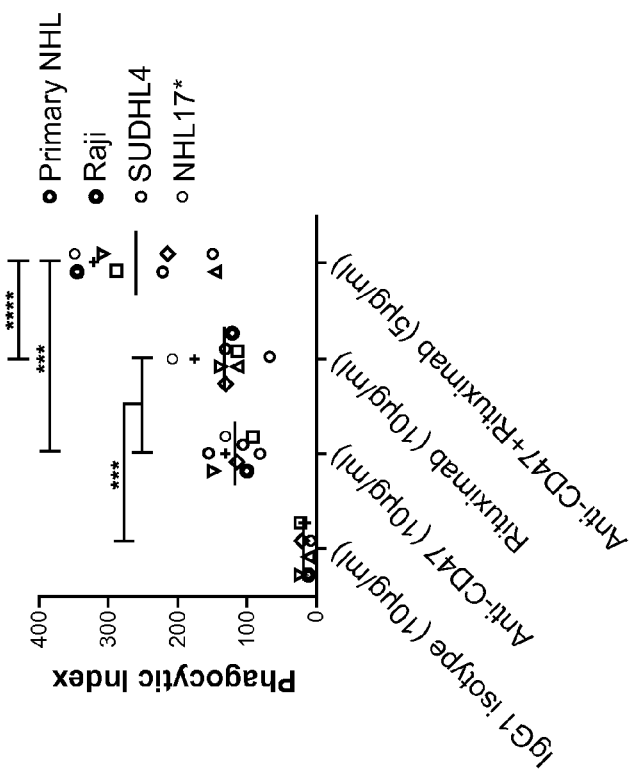

Next, we tested the ability of a blocking anti-CD47 mAb to synergize with rituximab in the phagocytosis of NHL cells. We examined CD20 expression on NHL cells and found no difference between normal B cells and NHL cells. Incubation of NHL cells with rituximab in the presence of mouse or human macrophages resulted in significant phagocytosis (FIG. 13D). We then tested the synergy hypothesis by isobologram analysis. Using Raji, SUDHL4, and NHL17 cells, which express varying levels of both CD47 and CD20, anti-CD47 antibody synergized with rituximab or anti-human CD20 (mouse IgG2a) antibody, as indicated by combination indices less than 1 (FIG. 13C). In a second approach, in vitro phagocytosis assays were conducted with primary NHL cells incubated with either anti-CD47 antibody or rituximab alone, or both in combination at half of the single agent dose. NHL cells exhibited a significant increase in phagocytosis when incubated with the combination compared to either antibody alone when using mouse (FIG. 13D) or human (FIG. 13E) macrophage effectors. No phagocytosis of NPB cells was observed with either antibody alone or in combination with human macrophages (FIG. 13E).

Ex Vivo Coating of NHL Cells with an Anti-CD47 Antibody Inhibits Tumor Engraftment.

Figure 14A:
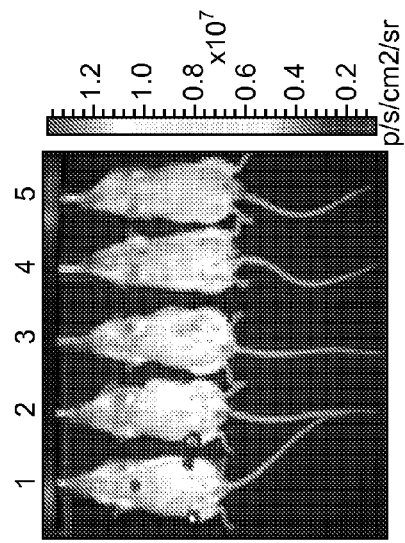
FIG. 14. Ex Vivo Coating of NHL Cells with an Anti-CD47 Antibody Inhibits Tumor Engraftment (A-F) Luciferase-expressing Raji (A) and SUDHL4 (C) cells were assessed for ex vivo antibody coating by flow cytometry. SCID mice transplanted with Raji (B) and SUDHL4 (D) were subject to bioluminescent imaging (1-IgG1 isotype control, 2-anti-CD45, 3 and 4-anti-CD47, 5-luciferase negative control). Bioluminescence for Raji (E) and SUDHL4 (F) engrafted mice was quantified (n=3 per antibody condition). No tumor engraftment was observed in mice transplanted with anti-CD47-coated cells compared to IgG-coated cells (p<0.05) for both Raji and SUDHL4, as assessed by bioluminescent imaging. Data are represented as mean±standard deviation (SD). (G) Bulk lymphoma cells from a human NHL patient were assessed for ex vivo antibody coating by flow cytometry. (H) Compared to IgG1 isotype control, anti-CD47 antibody pretreatment inhibited engraftment of NHL cells (p<0.0001) whereas anti-CD45-coated cells engrafted similarly to controls (p=0.54). All p values were determined using Fisher's exact test. Error bars represent SD (E and F).
Figure 14B:
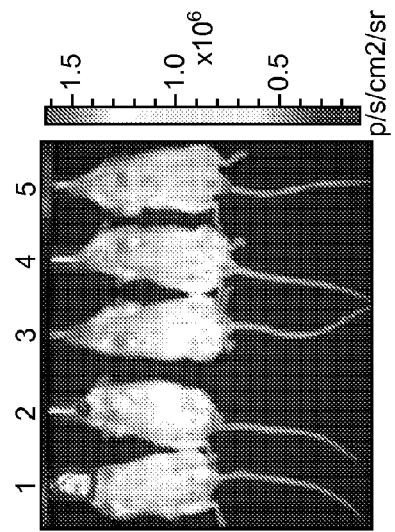
Figure 14C:
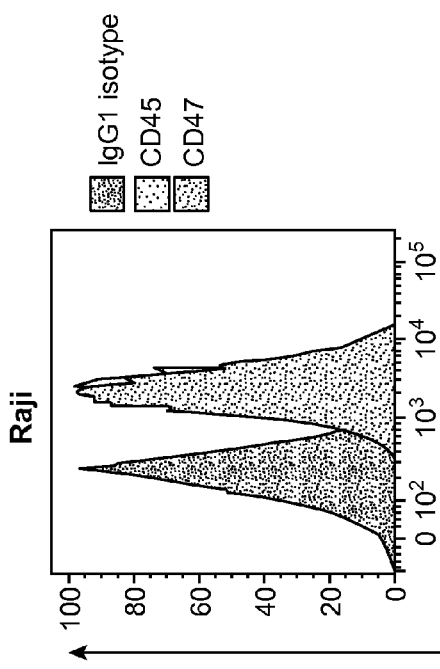
Figure 14D:
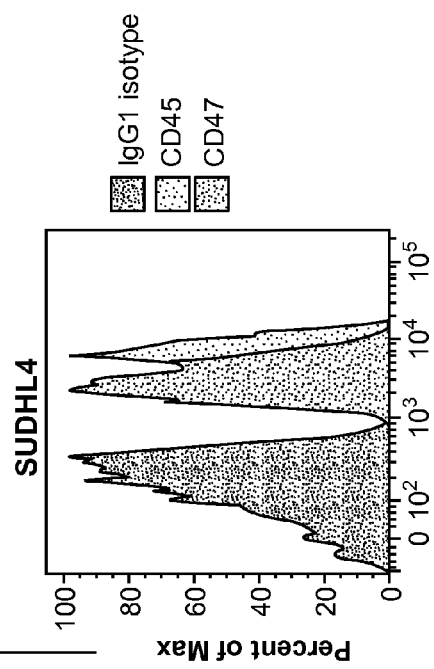

Next, the ability of blocking anti-CD47 antibody to eliminate NHL in vivo either alone or in combination with rituximab was explored by two separate treatment strategies. First, the effect of ex vivo anti-CD47 antibody coating on the engraftment of human NHL cells was tested. Luciferase-expressing Raji and SUDHL4 cell lines were precoated ex vivo with anti-CD47, IgG1 isotype control, or anti-CD45 antibody and transplanted intravenously into SCID mice. Coating with anti-CD47 antibody prevented engraftment of both cell lines (FIGS. 14A-14F). Coating of Raji cells with rituximab also inhibited engraftment when transplanted into SCID mice. In addition to these cell lines, we identified a primary NHL patient specimen that engrafted in NSG mice in the bone marrow upon intravenous transplantation. As with the cell lines, ex vivo coating of these primary cells with anti-CD47 antibody, but not controls (FIG. 14G), resulted in complete inhibition of bone marrow engraftment (FIG. 14H).

Combination Therapy with Anti-CD47 Antibody and Rituximab Eliminates Lymphoma in Both Disseminated and Localized Human NHL Xenotransplant Models.

Figure 15B:
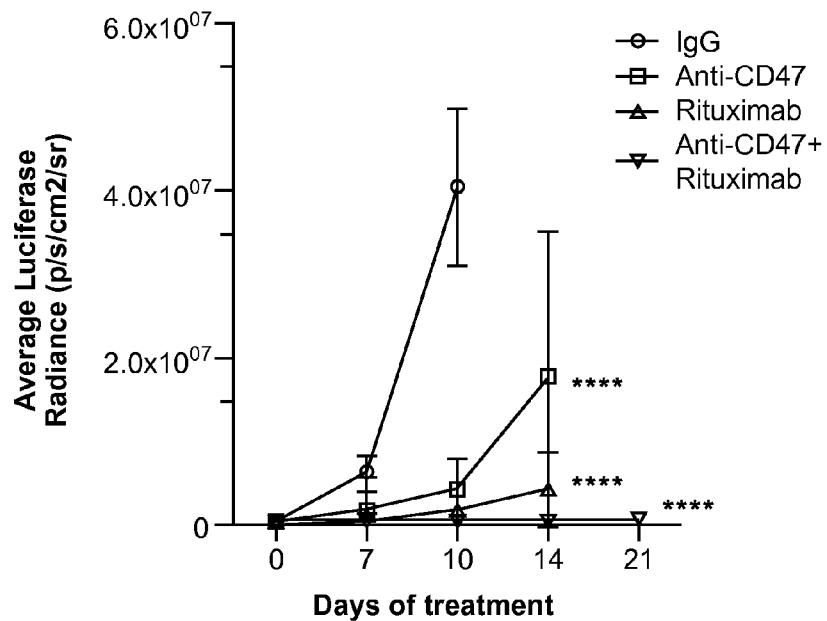
FIG. 15. Combination Therapy with Anti-CD47 Antibody and Rituximab Eliminates Lymphoma in Both Disseminated and Localized Human NHL Xenotransplant Mouse Models (A) NSG mice transplanted intravenously with luciferase-expressing Raji cells were treated with the indicated antibodies (n=8 per treatment group). Luciferase imaging of representative mice from pre- and 10 days post-treatment are shown (A) and averaged for all mice in each treatment group (B). (C) Kaplan-Meier survival analysis was performed. p values compare IgG control to combination antibody treatment or anti-CD47 antibody/rituximab single antibody to combination. Arrows indicate start (day 14) and stop (day 35) of treatment. (D) Luciferase-expressing Raji cells were transplanted subcutaneously in the flank of NSG mice. When palpable tumors (~0.1 cm$^3$) formed, treatment began with the indicated antibodies. Luciferase imaging of representative mice from each treatment group is shown before (day 0) and during (day 14) treatment. (E) Quantified bioluminescence was determined and averaged for all mice in each treatment group (n=7). (F) Tumor volume was measured with average volume shown. p values were derived from a two-way ANOVA and compared to IgG treatment. *p<0.05, *p<0.001, **p<0.0001. Complete remission was defined as the number of mice with no evidence of tumor at the indicated date. Relapse was defined as the number of mice achieving a complete remission that later developed recurrence of tumor growth. For (E), one mouse that achieved a complete remission died of non-tumor-related causes. Data presented in (B), (E), and (F) are mean values±SD.
Figure 15C:
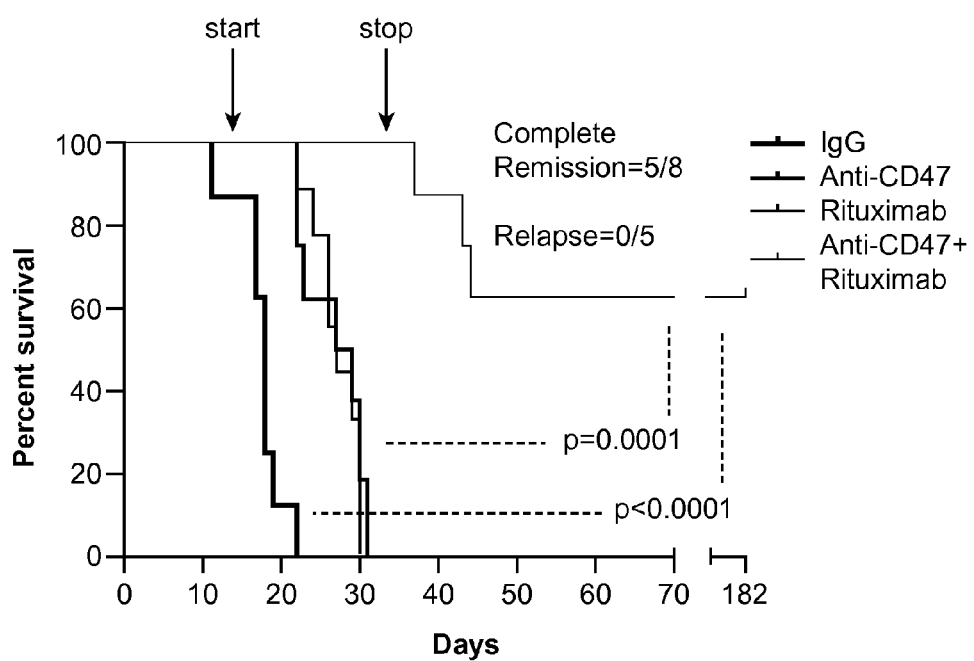

In the second treatment strategy, mice were first engrafted with NHL and then administered single or combination antibody therapy. To best model NHL, we established disseminated and localized xenotransplantation models in NSG mice that are deficient in T, B, and NK cells but retain phagocyte effector cells. In the disseminated model, luciferase expressing Raji cells were transplanted intravenously into adult NSG mice. Two weeks later, these mice were administered daily injections of either control mouse IgG, anti-CD47 antibody, rituximab, or anti-CD47 antibody and rituximab. Anti-CD47 antibody treatment decreased the lymphoma burden in these mice (FIGS. 15A and 15B) and significantly prolonged survival compared to control IgG, although all mice eventually died (FIG. 15C). Similar results were seen with rituximab and were not statistically different compared to anti-CD47 antibody (FIGS. 15A-15C). In contrast, combination therapy with anti-CD47 antibody and rituximab eliminated lymphoma in 60% of mice as indicated by long-term survival (FIG. 15C) and the absence of luciferase-positive lymphoma more than 4 months after the end of treatment. In humans, rituximab efficacy is thought to be primarily mediated by both macrophages and NK cells. Given that NSG mice lack NK cells, we conducted a similar experiment in NK cell-containing SCID mice and observed similar therapeutic responses as in NSG mice.

Figure 15D:
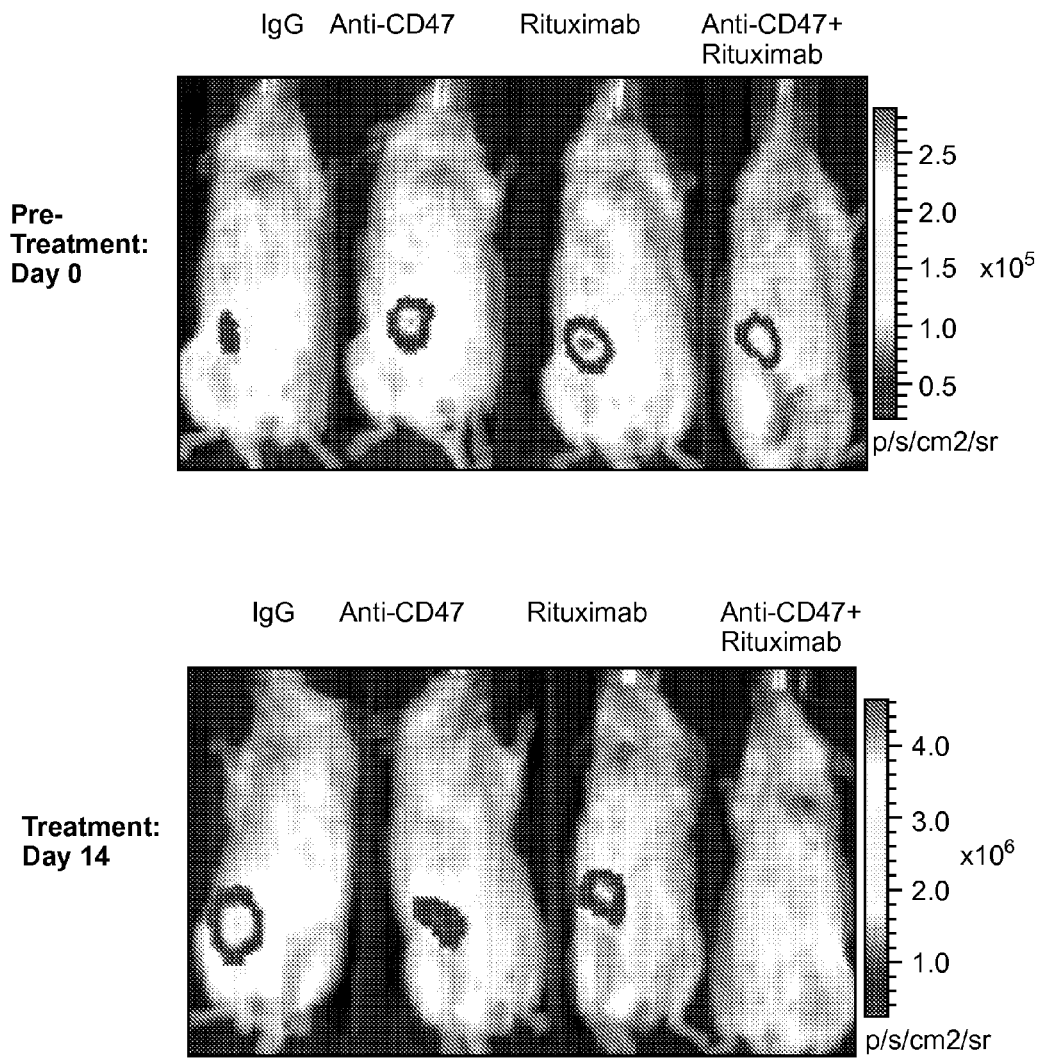
Figure 15E:
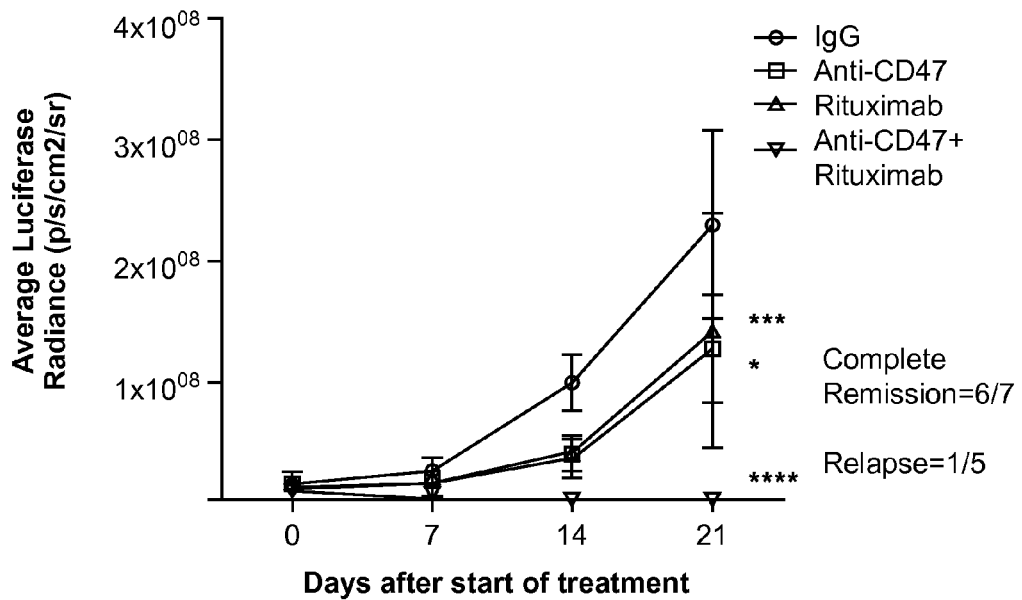
Figure 15F:
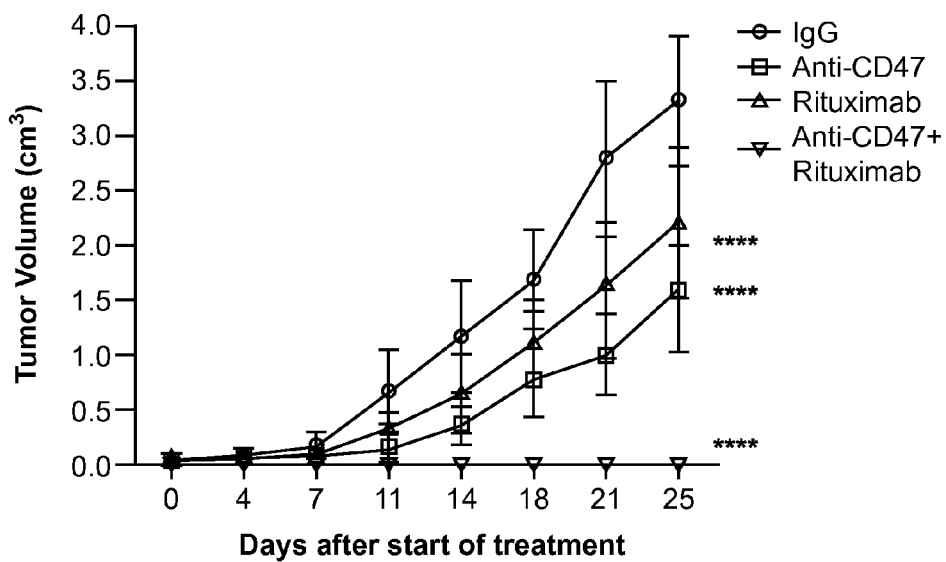

In the localized NHL model, luciferase-expressing Raji cells were transplanted subcutaneously in the right flank of NSG mice. Once tumors were palpable (approximately 2 weeks), mice were treated with antibody therapy. Mice treated with anti-CD47 antibody or rituximab demonstrated a decreased rate of lymphoma growth compared to control IgG-treated mice as measured by both luciferase signal and tumor volume (FIGS. 15D-15F) but, like controls, eventually had to be sacrificed due to enlarged tumor growth. In contrast, mice treated with the combination of anti-CD47 antibody and rituximab demonstrated complete elimination of lymphoma, with 86% of treated mice having no measurable mass or luciferase-positive lymphoma 4 weeks after the end of therapy (FIGS. 15D-15F). Moreover, all showed no evidence of tumor growth, remained relapse free, and were alive at over 197 days after tumor engraftment. Out of six mice achieving a complete remission, five remained relapse free whereas one mouse died of nontumor-related causes (FIG. 15E). For both disseminated and localized xenograft models, expression of CD47 and CD20 in transplanted Raji cells did not differ from Raji cells in culture.

Combination Therapy with Anti-CD47 Antibody and Rituximab Eliminates Lymphoma in Primary Human NHL Xenotransplant Mouse Models.

Figure 16A:
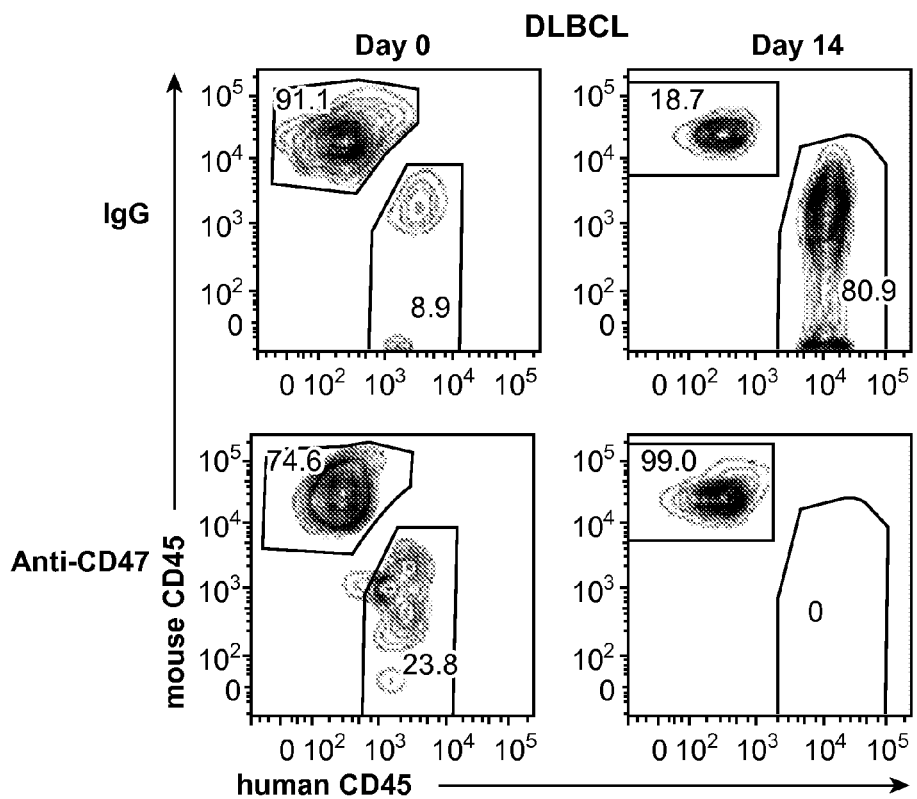
FIG. 16. Combination Therapy with Anti-CD47 Antibody and Rituximab Eliminates Lymphoma in Primary Human NHL Xenotransplant Mouse Models (A and B) Sublethally irradiated NSG mice were transplanted intravenously with cells from a primary DLBCL patient (NHL7) and treated with the indicated antibodies. Flow cytometry of human lymphoma engraftment in the bone marrow of two representative mice is shown pre- and 14 days post-antibody treatment in (A). Data from all mice are included in (B). $**p<0.01$, comparing pre- and post-treatment values for each respective antibody treatment. (C) Kaplan-Meier survival analysis of DLBCL-engrafted mice from each antibody treatment cohort is shown ($n \geq 10$ per antibody group), with p values calculated comparing control IgG to combination antibody treatment or anti-CD47 antibody/rituximab single antibody to combination treatment. Arrows indicate start (day 14) and stop (day 28) of treatment. (D and E) Mice engrafted intravenously with a primary FL patient sample (NHL31) were treated with a single dose of the indicated antibodies. Compared to IgG control and rituximab, anti-CD47 antibody alone or in combination with rituximab eliminated tumor burden in the peripheral blood ($p=0.04$, two-way ANOVA) and bone marrow ($p<0.001$, t test). (E) Lyphoma engraftment in the bone marrow was determined 14 days post-treatment. Each antibody treatment group consisted of three mice. For mice reported in (D) and (E), human lymphoma chimerism was between 5% and 25% in the peripheral blood and bone marrow. Error bars represent SD (D and E).
Figure 16B:
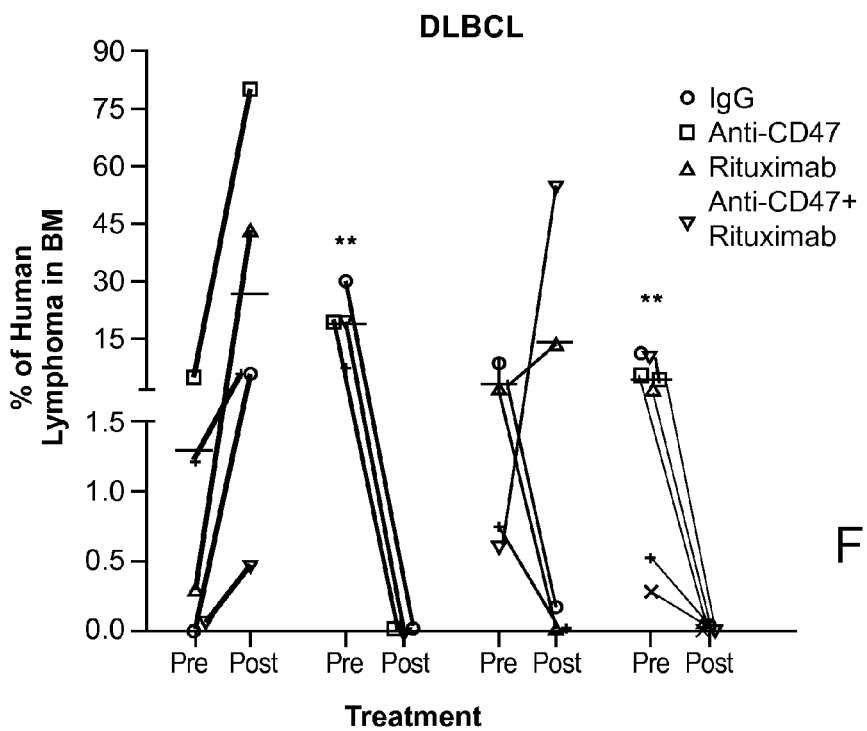
Figure 16C:
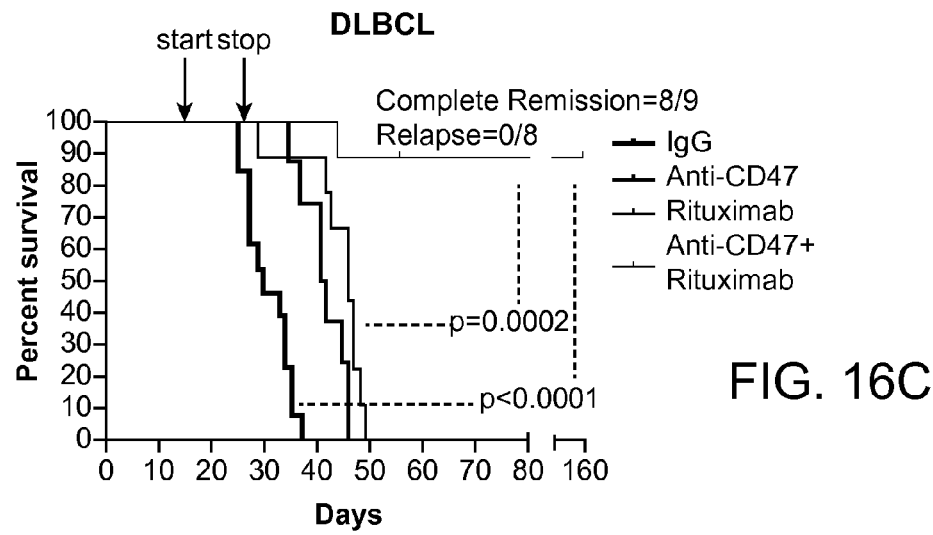
Figure 16D:
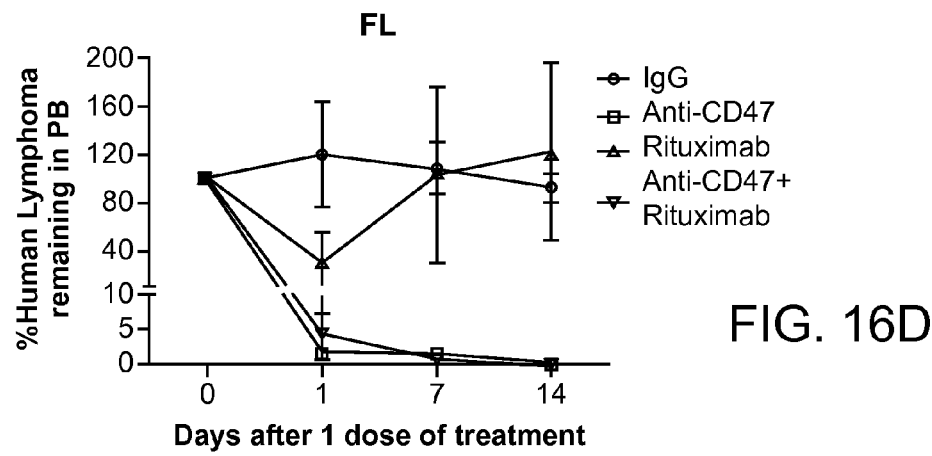
Figure 16E:
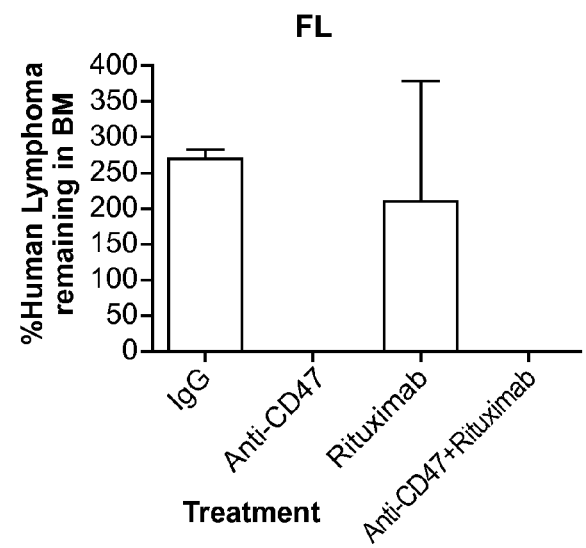

NHL cell lines have been valuable for the evaluation of therapeutics, but they may not accurately recapitulate the heterogeneity of the primary disease. We report here two new mouse xenograft models for NHL in which intravenous transplantation of cells from a DLBCL patient (NHL7/SUNHL7) and a FL patient (NHL31/SUNHL31) give rise to robust lymphoma engraftment in the bone marrow and/or peripheral blood. Primary DLBCL cells were transplanted into mice, which 2 weeks later were treated with daily injections of antibodies for 14 days. Treatment with anti-CD47 antibody either alone or in combination with rituximab eliminated human lymphoma in the bone marrow, whereas treatment with rituximab resulted in a reduction of disease in 60% of mice (FIGS. 16A and 16B). Mouse hematopoietic cells were unaffected by antibody therapy. Treatment was then discontinued, and all mice were monitored for survival. Mice treated with either anti-CD47 antibody or rituximab alone had a significantly longer survival compared to mice treated with control IgG, but all eventually died secondary to disease due to widespread organ dissemination on autopsy (FIG. 15C). Most significantly, 8 out of 9 mice (89%) administered combination antibody treatment were cured of lymphoma, as indicated by long-term disease-free survival more than 4 months after the end of treatment (FIG. 16C) with no detectable lymphoma in the bone marrow. In a second primary model, FL cells were transplanted intravenously in a similar manner. $CD20^+CD10^+$ lymphoma engraftment in the peripheral blood and bone marrow was detected after 8 weeks. At this time, mice were treated with a single intraperitoneal injection of either control IgG, anti-CD47 antibody, rituximab, or the combination and then followed for disease progression. A single dose of anti-CD47 antibody alone or in combination with rituximab eliminated lymphoma both in the peripheral blood (FIG. 16D) and in bone marrow (FIG. 16E). In contrast, a single dose of rituximab enabled a partial reduction in tumor burden that rebounded back to baseline levels in the peripheral blood with no tumor reduction observed in the bone marrow. The difference in anti-CD47 antibody clearance of lymphoma as a single dose in FL-engrafted mice (FIGS. 16D and 16E) compared to multiple dose therapy in mice engrafted with DLBCL (FIG. 16B) or Raji (FIG. 15) may be due to cell-intrinsic differences in antibody sensitivity between different NHL subtypes or due to different anti-CD47 antibody potencies in distinct tissue compartments (peripheral blood versus bone marrow (BM) versus soft tissue compartments). To assess the ability of these two primary NHL xenotransplant models to model the disease, we compared histological sections of the primary NHL specimen and the transplanted tumor. Similar DLBCL and FL morphology was observed for NHL7 and NHL31, respectively. We next determined whether the percentages of macrophages infiltrating the tumor differed between the primary patient and the xenografted tumor. For NHL31, the percentage of infiltrating human macrophages ($CD68^+$) in the primary lymph node was similar to the percentage of infiltrating mouse macrophages ($F4/80^+$) in bone marrow of transplanted mice. Analyzing infiltrating macrophage frequency by flow cytometry, no difference was observed between the primary specimen and xenograft for either NHL7 or NHL31.

Synergy Between Anti-CD47 Antibody and Rituximab does not Occur Through NK Cells or Complement.

Figure 17A:
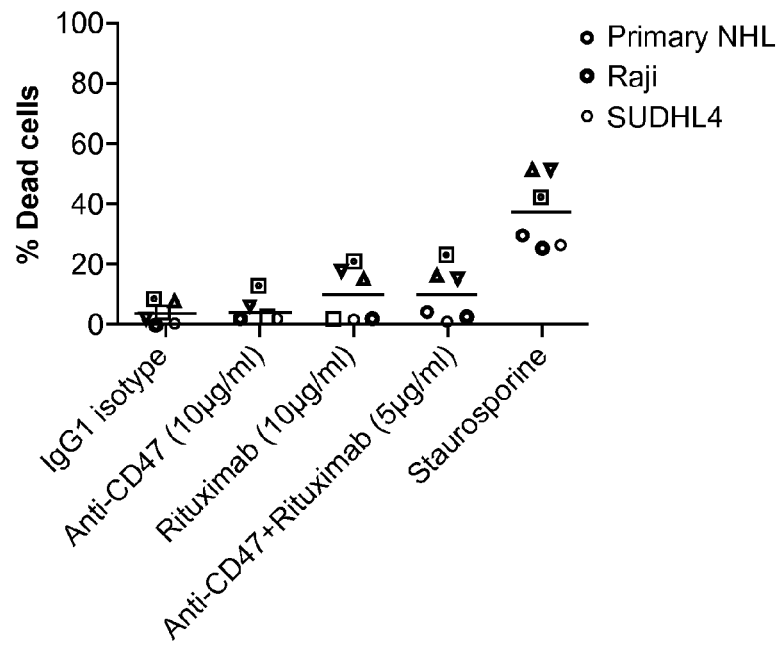
FIG. 17. Synergy between Anti-CD47 Antibody and Rituximab Does Not Occur through NK Cells or Complement (A) NHL cells were incubated with the indicated soluble antibodies for 2 hr and the percentage of dead cells was calculated (% annexin V$^+$ and/or 7-AAD$^+$). No statistically significant difference in % dead cells was observed with the combination of anti-CD47 antibody and rituximab compared to either anti-CD47 antibody alone ($p=0.24$) or rituximab alone ($p=0.95$). (B) SIRPα expression is shown for both human and mouse NK cells as determined by flow cytometry. (C and D) Chromium release assays measuring ADCC were performed in triplicate with human (C) and mouse (D) at an effector:target ratio of 17.5:1, and percent specific lysis is reported. Antibodies were incubated at 10 µg/ml except anti-CD47 full-length or F(ab')$_2$ antibody+rituximab (5 µg/ml). (E) CDC assay with human complement was performed in duplicate. Compared to IgG1 isotype control, anti-CD47 antibody did not enable CDC ($p>0.2$), whereas rituximab did ($p<0.001$) by two-way ANOVA for both SUDHL4 and NHL17*. Combination treatment with anti-CD47 antibody and rituximab did not enable greater levels of CDC compared to rituximab ($p=0.78$). (F) CDC assay with mouse complement was performed in duplicate. Compared to IgG1 isotype control, anti-CD47 antibody did not enable CDC ($p>0.25$) whereas rituximab did ($p=0.03$, $p=0.08$, respectively) for both SUDHL4 and NHL17*. No difference in CDC between CD47 antibody+rituximab and rituximab alone was observed ($p>0.13$) for both SUDHL4 and NHL17*. $*p<0.05$, $p<0.01$, $*p<0.001$, $****p<0.0001$. Error bars represent SD (C-F). NHL17*=primary NHL17 cells expanded in culture.

Rituximab can eliminate malignant cells via apoptosis, NK cellmediated ADCC, and CDC. However, it is not known whether anti-CD47 antibody also enables ADCC or CDC in addition to phagocytosis. Therefore, we investigated whether anti-CD47 antibody alone could induce antitumor effects by macrophage-independent mechanisms, and whether synergy with rituximab could occur through these modalities. First, to investigate possible synergy in direct apoptosis, NHL cells were incubated with either anti-CD47 antibody/rituximab alone or in combination without macrophages, and cell death was measured. No synergistic apoptosis was observed when NHL cells were incubated with soluble (FIG. 17A) or immobilized antibodies. Furthermore, crosslinking of soluble anti-CD47 antibody alone or in combination with rituximab by macrophages did not induce increased apoptosis of nonphagocytosed NHL cells compared to IgG1 isotype control, whereas rituximab induced a slight increase in apoptosis. No synergistic apoptosis was observed in this context. The small increase in apoptosis upon antibody treatment was not FcR dependent given that results were similar with macrophages lacking the Fcg subunit.

Figure 17B:
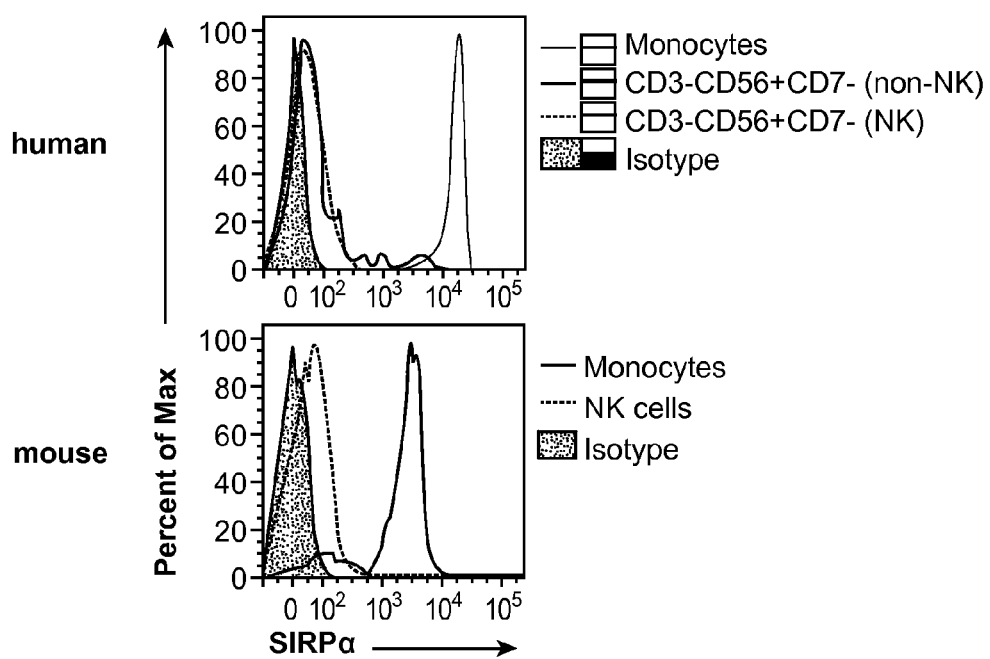
Figure 17C:
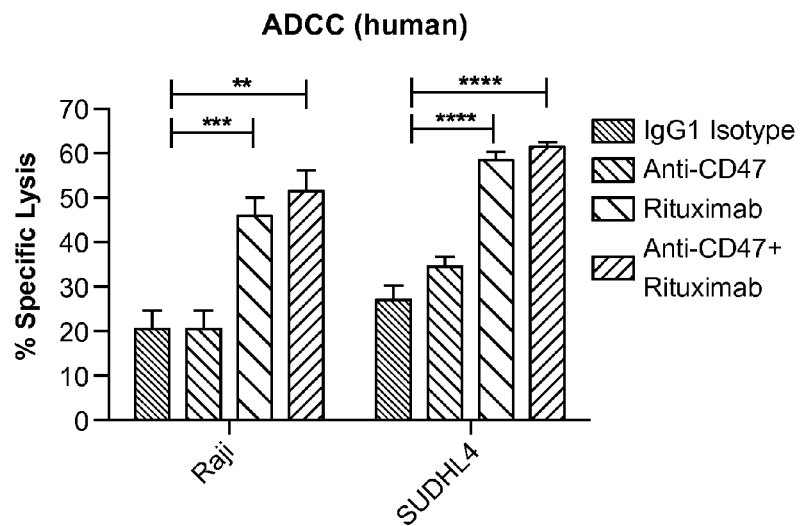
Figure 17D:
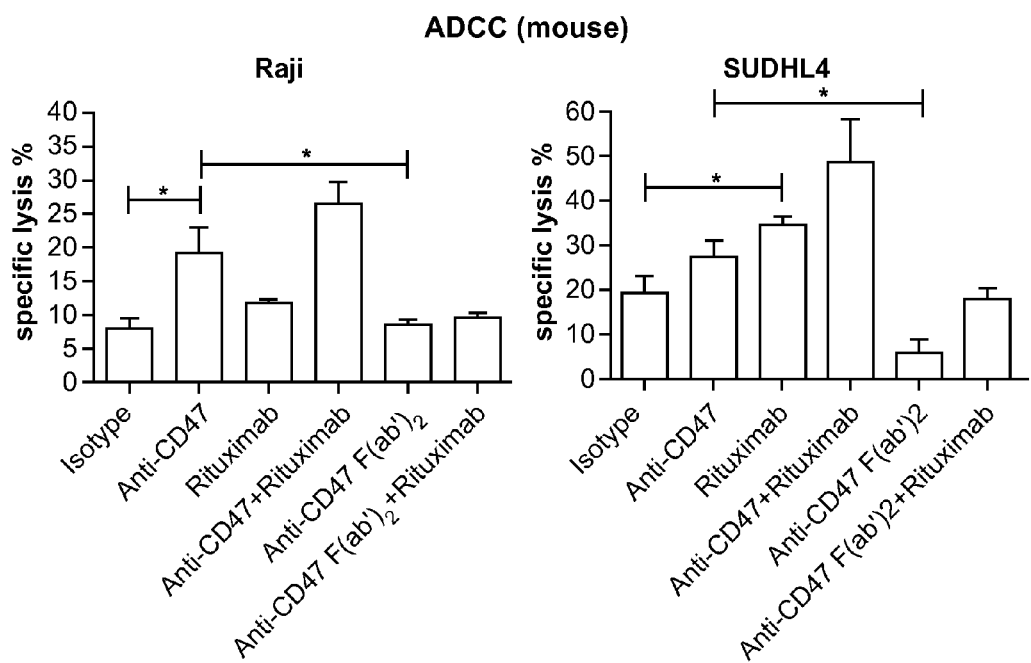

Second, we investigated whether NK cells could mediate tumor elimination by anti-CD47 antibody alone or in synergy with rituximab. We first determined whether human or mouse NK cells expressed SIRPα and found that both human NK cells, $CD3^-CD56^+CD7^+$, as well as mouse NK cells, $CD3^-DX5^+$, expressed minimal to no SIRPα (FIG. 17B). Next, the ability of anti-CD47 antibody to induce NK cell-mediated ADCC through FcRs or by CD47-SIRPα blockade was investigated. Utilizing human NK cells as effectors, anti-CD47 antibody did not induce increased ADCC of Raji or SUDHL4 cells compared to IgG1 isotype control (FIG. 17C). Although rituximab did enable ADCC of these two NHL cell lines, no synergistic effect between anti-CD47 antibody and rituximab was observed (p=0.77, FIG. 17C). As anti-CD47 antibody (B6H12.2) is a mouse IgG1 isotype, we repeated these assays with mouse NK cells. Anti-CD47 antibody caused increased ADCC of these two NHL cell lines compared to isotype control, whereas rituximab induced ADCC to a lesser degree (FIG. 17D). To test whether anti-CD47 antibody-mediated ADCC was Fc dependent, we generated a $F(ab')_2$ fragment of the anti-CD47 antibody. The $F(ab')_2$ fragment did not enable ADCC, indicating that the increased ADCC was likely mediated through FcRs (FIG. 17D). The combination of anti-CD47 antibody or $F(ab')_2$ fragment with rituximab did not induce a statistically significant increase in ADCC compared to single agent therapy, indicating no synergistic effect.

Figure 17E:
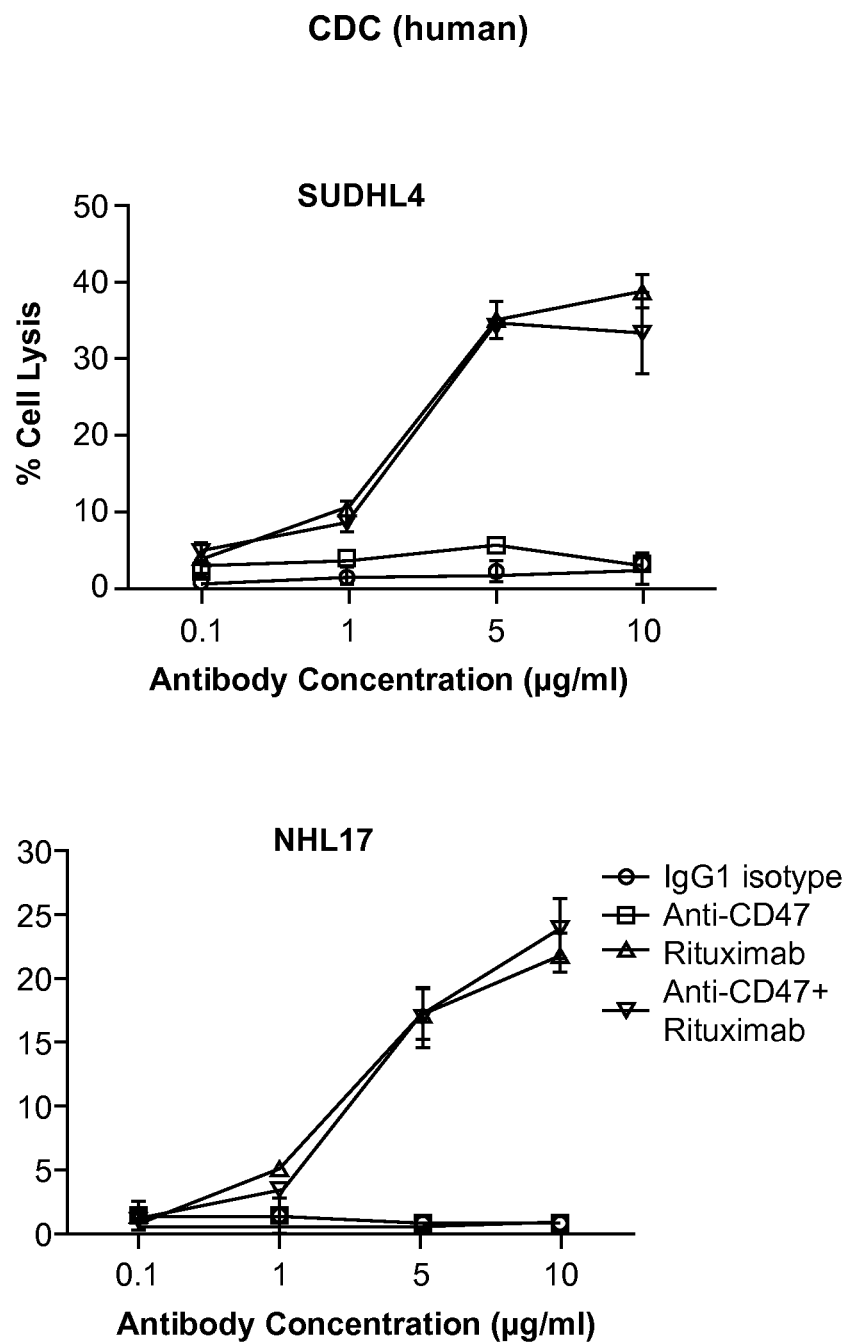

Third, we investigated the role of complement in anti-CD47 antibody mediated cytotoxicity. Using either human (FIG. 17E) or mouse (FIG. 17F) complement, anti-CD47 antibody did not induce CDC of either an NHL cell line or a primary NHL sample, whereas rituximab did induce significant CDC against both of these samples. Moreover, the combination of anti-CD47 antibody and rituximab did not induce increased CDC compared to rituximab alone.

Fourth, we investigated the relative contribution of major components of macrophages, NK cells, and complement in mediating the therapeutic effects of anti-CD47 antibody and rituximab in vivo. Luciferase-labeled Raji cells were engrafted intravenously into SCID mice, which have functional macrophages, NK cells, and complement. Mice were then separated into cohorts receiving selective depletion of either macrophages by clodronate, NK cells by anti-asialoGM1 antibody, complement by cobra venom factor, or a vehicle control. These cohorts were then treated with combination anti-CD47 antibody and rituximab therapy for 3 days, and tumor burden was measured by bioluminescent imaging pre- and post-treatment. Compared to vehicle control, NK cell and complement depletion had no effect on tumor elimination by combination antibody therapy. In contrast, macrophage depletion significantly abrogated the therapeutic effect, indicating that macrophages, and not NK cells or complement, are required for combination anti-CD47 antibody and rituximab-mediated elimination of NHL in vivo.

Anti-CD47 Antibody Synergizes with Rituximab through FcR-Independent and FcR-Dependent Mechanisms.

Figure 18B:
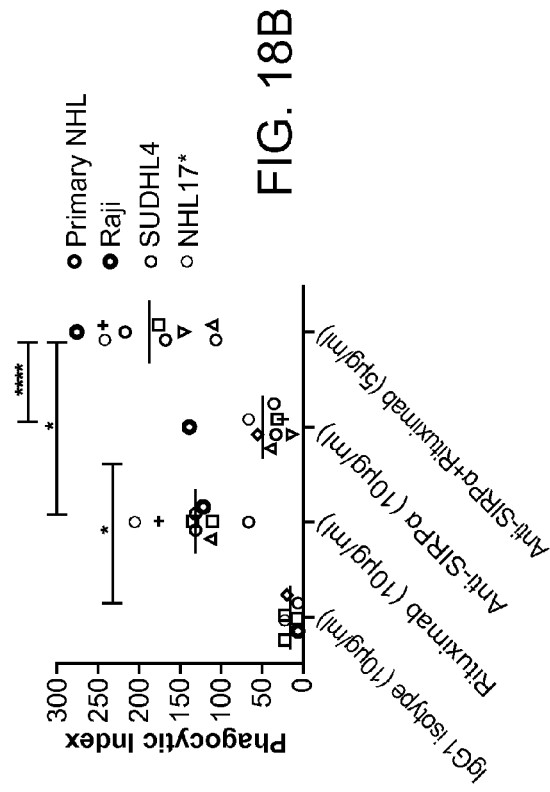
FIG. 18. Anti-CD47 Antibody Synergizes with Rituximab through FcR-Independent and FcR-Dependent Mechanisms (A) Isobologram analysis of phagocytosis induced by anti-SIRPa antibody and rituximab is shown for Raji cells and mouse macrophages. (B and C) NHL cells were incubated in vitro with the indicated antibodies in the presence of wild-type (B) or Fcγr$^{-/-}$ (C) mouse macrophages, and the phagocytic index was determined. (D) Isobologram analysis of phagocytosis induced by anti-CD47 F(ab')$_2$ antibody and rituximab is shown for Raji cells and mouse macrophages. (E) NHL cells were incubated with wild-type mouse macrophages in the presence of the indicated full-length or F(ab')$_2$ antibodies (single antibodies at 10 µg/ml, combination antibodies at 5 µg/ml each) and the phagocytic index was determined. (F) The level of in vivo phagocytosis measured as the percentage of mouse macrophages containing phagocytosed GFP+ Raji cells (hCD45$^-$GFP$^+$F4/80$^+$) was determined by flow cytometry of livers from mice engrafted with GFP+ Raji cells and then treated with the indicated antibodies (see Experimental Procedures), with each treatment group performed in duplicate. Compared to IgG control, anti-CD47 antibody and rituximab enabled increased levels of phagocytosis. Compared to anti-CD47 antibody alone, combination anti-CD47 antibody and rituximab enabled higher levels of phagocytosis. $*p<0.05$, $p<0.01$, $**p<0.0001$. Error bars represent SD (E and F).
Figure 18D:
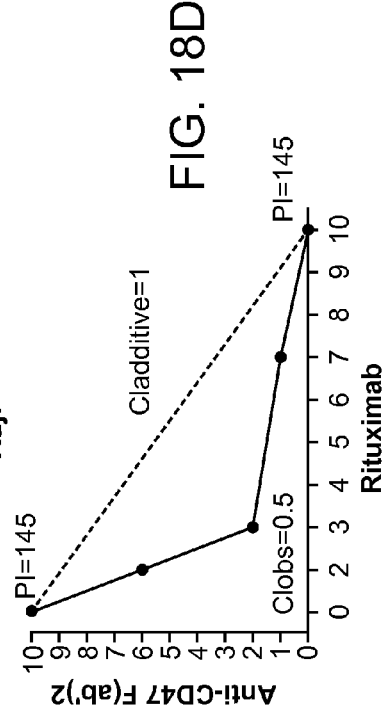
Figure 18A:
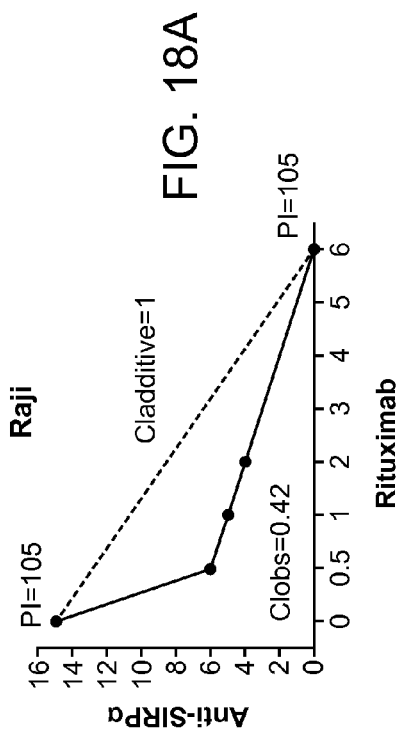
Figure 18C:
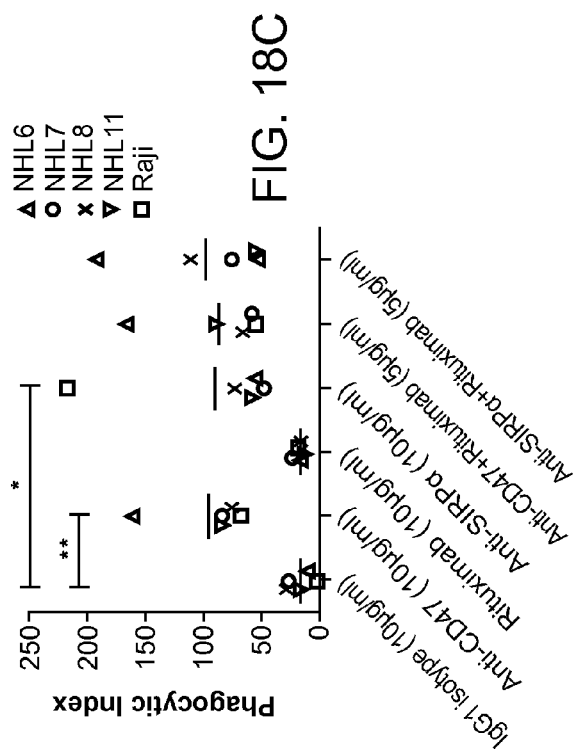

We hypothesize that the observed synergy between an anti-CD47 antibody and rituximab occurs through the combination of two separate mechanisms for stimulating phagocytosis: (1) FcR-independent through blockade of an inhibitory phagocytic signal by anti-CD47 antibody, and (2) FcR-dependent through delivery of a positive phagocytic signal by rituximab. We utilized four independent methods to investigate this hypothesis. First, synergistic phagocytosis was observed with the combination of anti-SIRPa antibody and rituximab by isobologram analysis (FIG. 18A), and with a large panel of primary NHL samples (FIG. 18B). Second, mouse macrophages lacking the Fcγ receptor, thereby incapable of enabling FcR-dependent phagocytosis, but still expressing SIRPα, were utilized as effector cells for phagocytosis of NHL cells incubated with either anti-CD47 antibody, anti-SIRPα antibody, rituximab, or anti-CD47/anti-SIRPα antibody in combination with rituximab. As predicted, anti-CD47 antibody and anti-SIRPα antibody, but not rituximab, enabled phagocytosis of NHL cells, without evidence of synergistic phagocytosis (FIG. 18C).

Figure 18F:
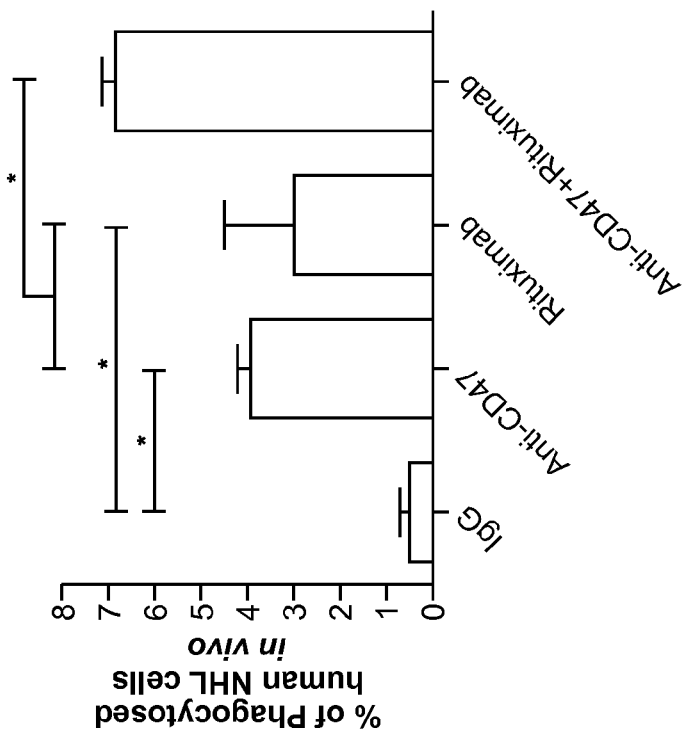
Figure 18E:
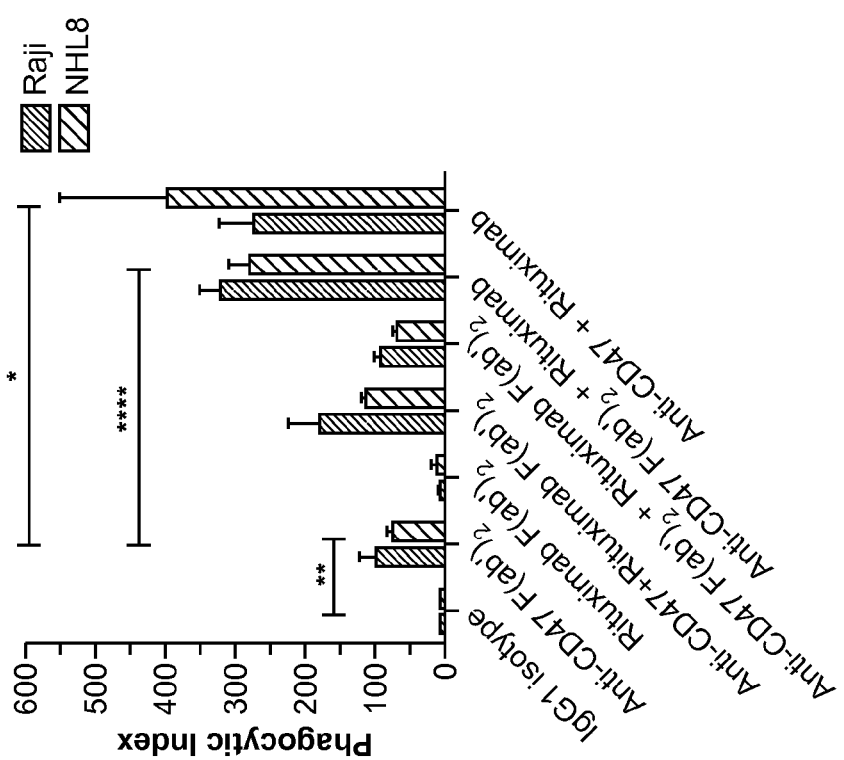

Third, $F(ab')_2$ fragments of both anti-CD47 antibody and rituximab were generated and utilized in phagocytosis assays with NHL cells and wild-type macrophages. Anti-CD47 $F(ab')_2$ antibody synergized with rituximab as demonstrated by isobologram analysis (FIG. 18D). Additionally, anti-CD47 $F(ab')_2$, but not rituximab $F(ab')_2$, enabled phagocytosis of NHL cells (FIG. 18E). Consistent with the proposed mechanism, synergistic phagocytosis was observed with the combination of either full-length anti-CD47 or anti-CD47 $F(ab')_2$ with full-length rituximab, but not with any combination involving rituximab $F(ab')_2$ (FIG. 18E).

Fourth, synergistic phagocytosis was investigated in vivo using GFP+ Raji cells engrafted in NSG mice. As single agents, anti-CD47 antibody and rituximab enabled phagocytosis of Raji cells engrafted in the liver as evidenced by an increased percentage of mouse macrophages containing phagocytosed GFP+ Raji cells (FIG. 18F). Most significantly, combination anti-CD47 antibody and rituximab treatment enabled significantly increased phagocytosis compared to either single agent demonstrating that synergistic phagocytosis occurred in vivo (FIG. 18F).

In this report, we identify a distinct mechanism of synergy between mAbs in cancer therapy leading to cures in the absence of chemotherapy. Specifically, we utilized a blocking anti-CD47 antibody in combination with the anti-CD20 antibody rituximab to eradicate human NHL through a mechanism of synergy involving FcR-independent enabling of phagocytosis by anti-CD47 antibody and FcR-dependent stimulation of phagocytosis by rituximab. In addition, the identification of CD47 expression as a prognostic factor can be incorporated into standard clinical prognostic considerations across multiple subtypes of NHL and is useful in risk-adapted therapy decision-making. Although it is thought that many therapeutic mAbs for human malignancies, including rituximab, function primarily through NK cell-mediated ADCC, several lines of evidence indicate that the therapeutic effect of anti-CD47 antibody alone or in combination with rituximab is mediated primarily through macrophage phagocytosis. First, synergistic macrophage phagocytosis was observed with combination anti-CD47 antibody and rituximab in vitro, whereas no synergy was observed for direct apoptosis, ADCC, or CDC. Second, phagocytosis of NHL cells in vivo was observed with either anti-CD47 antibody or rituximab alone and, most importantly, significantly increased with combination therapy. Third, the therapeutic effect of combination antibody treatment was similar in an NHL xenotransplant model using complement and NK cell-deficient NSG mice as in complement and NK cell-competent SCID mice, suggesting that macrophages alone are sufficient to mediate the therapeutic effect. Fourth, depletion of macrophages, but not complement or NK cells, abrogated the synergistic effect of anti-CD47 antibody in combination with rituximab. These studies highlight the importance of macrophages as effectors of anti-CD47 antibody therapy in human NHL.

This study describes a mechanism of antibody synergy in the elimination of NHL in the absence of chemotherapy. Combination antibody therapies for NHL have previously been investigated, mostly in combination with rituximab, with some progressing to clinical trials. These include a humanized antibody targeting the B cell antigen CD22 (epratuzumab) and galiximab, a chimeric antibody targeting the costimulatory ligand CD80. Phase I/II studies with either epratuzumab or galiximab in combination with rituximab demonstrate relative safety and clinical responses equal to or greater than single agent therapy alone. Based on these results, phase III trials are underway. Antibody combinations involving anti-CD20 antibodies and antibodies to proapoptotic receptors are also being explored preclinically. These studies highlight the clinical potential of combination antibody approaches in NHL patients. Combination therapy with two or more mAbs possesses several advantages compared to monotherapies in NHL or other malignancies. First, therapy solely with monoclonal antibodies targeting cancer-specific antigens could result in decreased off-target toxicity compared to current therapeutic regimens that utilize chemotherapy. Second, synergy between two distinct antibody effector mechanisms, FcR-independent and FcRdependent as shown here, would result in increased therapeutic efficacy. Third, antibody targeting of two distinct cell-surface antigens would be more likely to eliminate cancer cells with pre-existing epitope variants or epitope loss, such as those reported in rituximab-refractory/resistant NHL patients. Fourth, a bispecific FcR-engaging antibody with one arm binding and blocking CD47 and the other binding to a validated cancer antibody target (CD20) could reduce potential antibody toxicity, while retaining the synergy effect, especially as CD47 is expressed in multiple normal tissue types.

In addition to its application in NHL, the reported mechanism of antibody synergy provides proof-of-principle that a blocking mAb directed against CD47 can synergize with an FcR-activating antibody to provide superior therapeutic efficacy. This finding raises the possibility of synergy between an anti-CD47 antibody and other clinically approved therapeutic antibodies that activate FcRs on immune effector cells for the treatment of diverse human malignancies, including trastuzumab (Herceptin) for HER2-positive breast carcinomas, cetuximab (Erbitux) for colorectal carcinomas and head and neck squamous cell carcinomas, alemtuzumab (Campath) for CLL and T cell lymphoma, and others in development.

Experimental Procedures

Cell Lines.

A Burkitt's lymphoma cell line (Raji) and a DLBCL cell line (SUDHL4) were obtained from the American Type Culture Collection or generated in the lab. The NHL17* cell line was generated from a patient with DLBCL by culturing bulk cells in vitro with IMDM supplemented with 10% human AB serum for 1.5 months.

Human Samples.

Normal human peripheral blood and human NHL samples were obtained from the Stanford University Medical Center (Stanford, Calif., USA) with informed consent, according to an IRB-approved protocol or with informed consent from the Norwegian Radium Hospital (Oslo, Norway) according to a Regional Ethic Committee (REK)-approved protocol. Normal tonsils for germinal center B cell analysis were obtained from discarded tonsillectomy specimens from consented pediatric patients at Stanford University Medical Center according to an IRB-approved protocol.

Flow Cytometry Analysis.

For analysis of normal peripheral blood cells, germinal center B cells, and primary NHL cells, the following antibodies were used: CD19, CD20, CD3, CD10, CD45, CD5, CD38 (Invitrogen, Carlsbad, Calif., USA and BD Biosciences, San Jose, Calif., USA). Analysis of CD47 expression was performed with an antihuman CD47 FITC antibody (clone B6H12.2, BD Biosciences). Cell staining and flow cytometry analysis was performed as previously described.

Evaluation of Prognostic Value of CD47 in NHL.

Gene expression and clinical data were analyzed for eight previously described cohorts of adult NHL patients, including four studies of patients with DLBCL, three with B-CLL, and one with MCL. The clinical end points analyzed included overall (OS), progression free (PFS), and event-free survival (EFS), with events defined as the interval between study enrollment and need for therapy or death from any cause, with data censored for patients who did not have an event at the last follow-up visit.

Therapeutic Antibodies.

Rituximab (anti-CD20, human IgG1) was obtained from the Stanford University Medical Center, mouse anti-human CD20, IgG2a from Beckman Coulter (Miami, Fla., USA), and anti-CD47 antibody BRIC126, IgG2b from AbD Serotec (Raleigh, N.C., USA). Other anti-CD47 antibodies were used as in Majeti et al. (2009). All in vivo antibody experiments were performed using the anti-CD47 B6H12.2 antibody.

In Vitro Isobologram Studies.

In vitro phagocytosis assays were conducted with NHL cells incubated with anti-CD47 antibody (B6H12.2), anti-CD20 IgG2a, or rituximab either alone or in combination at concentrations from 1 μg/ml to 10 μg/ml. The concentration of each antibody required to produce a defined single-agent effect (phagocytic index) was determined for each cell type. Concentrations of the two antibodies combined to achieve this same phagocytic index were then plotted on an isobologram and the combination index (CI) determined. The CI was calculated from the formula $CI=(d1/D1)+(d2/D2)$, whereby d1=dose of drug 1 in combination to achieve the phagocytic index, d2=dose of drug 2 in combination to achieve the phagocytic index, D1=dose of drug 1 alone to achieve the phagocytic index, D2=dose of drug 2 alone to achieve the phagocytic index. A CI of less than, equal to, and greater than 1 indicates synergy, additivity, and antagonism, respectively.

In Vivo Precoating Engraftment Assay.

Assay were performed as previously described (Majeti et al., 2009). Precoated cells were transplanted intravenously into SCID mice or sublethally irradiated (200 rads) NOD.Cg-PrkdcscidIl2rgtm1Wjl/SzJ (NSG). All experiments involving mice were performed according to Stanford University institutional animal guidelines.

In Vivo Antibody Treatment in a Disseminated Lymphoma Xenograft Model.

$1.5 \times 10^6$ luciferase-labeled Raji cells were injected intravenously into the retro-orbital sinus of 6- to 10-week-old SCID or NSG mice. Those mice with luciferase-positive lymphoma were given daily intraperitoneal injections of 200 μg mouse IgG control, anti-CD47 antibody, rituximab, or 200 μg anti-CD47 antibody+200 μg rituximab for 3 weeks. Antibody treatment was then stopped and mice were followed for survival analysis. A complete remission (CR) was defined as no evidence of lymphoma by bioluminescence at the end of treatment. A relapse was defined as evidence of lymphoma by bioluminescence after the end of treatment in a mouse with a prior CR.

In Vivo Antibody Treatment in a Localized Lymphoma Xenograft Model.

$3 \times 10^6$ luciferase-labeled Raji cells were injected subcutaneously into the right flank of 6- to 10-week-old NSG mice. Those mice with luciferase-positive lymphoma were given daily intraperitoneal injections of 400 μg mouse IgG control, 400 μg anti-CD47, 200 μg rituximab, or 400 μg anti-CD47+ 200 μg rituximab for 4 weeks. Tumor volume was measured every 3-4 days using the formula (length*width)/2. Antibody treatment was then stopped and mice were followed for survival analysis.

In Vivo Antibody Treatment of Primary NHL-Engrafted Mice.

$2 \times 10^6$ NHL cells were transplanted intravenously via retro-orbital plexus into sublethally irradiated NSG mice. Two to ten weeks later, bone marrow was aspirated from these mice and those mice with evidence of human lymphoma engraftment ($hCD45^+CD19/CD10^+$ bone marrow cells) were then treated with the same antibody regimen as in the disseminated lymphoma model. After 14 days, bone marrow cells from these mice were aspirated and antibody treatment was stopped and mice followed for survival analysis. A CR was defined as no evidence of lymphoma in the BM at end of treatment. A relapse was defined as evidence of lymphoma in the BM after end of treatment in a mouse with a prior CR.

In Vivo Phagocytosis In vivo phagocytosis was performed as previously described (Majeti et al., 2009) analyzing mice transplanted with $GFP^+$ Raji cells into adult NSG mice. Mice were given a single dose of antibody and analyzed 4 hr later for in vivo phagocytosis.

What is claimed is:

1. A method for depleting hematologic cancer cells in a subject, the method comprising:
administering to the subject, at a dose that achieves depletion of hematologic cancer cells, a synergistic combination of antibodies comprising a first soluble antibody that binds to CD47 and prevents the binding of CD47 with SIRPα, and a second antibody that selectively binds CD20.

2. The method of claim 1, wherein one or both of said antibodies is conjugated to a cytotoxic agent.

3. The method of claim 2, wherein said cytotoxic agent is selected from the group consisting of a radioactive isotope, a chemotherapeutic agent and a toxin.

4. The method of claim 1, wherein the hematologic cancer cells are non-Hodgkin's lymphoma (NHL) cells.

5. The method of claim 4, wherein the NHL cells are diffuse large B cell lymphoma cells.

6. A method for depleting hematologic cancer cells in a subject, the method comprising:
administering to the subject, at a dose that achieves depletion of hematologic cancer cells, a soluble bispecific antibody selective for CD47 and CD20 that binds to CD47 and prevents the binding of CD47 with SIRPα, and that selectively binds CD20.

7. A method for depleting diffuse large B cell lymphoma cells in a subject, the method comprising:
   administering to the subject a synergistic combination of soluble antibodies comprising a first antibody that binds to CD47 and prevents the binding of CD47 with SIRPα, and a second antibody that selectively binds CD20;
   wherein diffuse large B cell lymphoma cells are depleted or eliminated from the subject.

8. The method of claim 6, wherein the hematologic cancer cells are diffuse large B cell lymphoma cells.

* * * * *